(12) United States Patent
Miranda et al.

(10) Patent No.: US 12,427,111 B2
(45) Date of Patent: Sep. 30, 2025

(54) LIPID NANOPARTICLES

(71) Applicant: CodeBridgeBio Inc., Woburn, MA (US)

(72) Inventors: Oscar R. Miranda, Revere, MA (US); Haitao Zhao, Beijing (CN); Xiaofeng Sun, Sharon, MA (US)

(73) Assignee: CodeBridgeBio Inc., Woburn, MA (US)

( * ) Notice: Subject to any disclaimer, the term of this patent is extended or adjusted under 35 U.S.C. 154(b) by 0 days.

(21) Appl. No.: 18/912,716

(22) Filed: Oct. 11, 2024

(65) Prior Publication Data
US 2025/0120914 A1 Apr. 17, 2025

Related U.S. Application Data

(60) Provisional application No. 63/589,693, filed on Oct. 12, 2023, provisional application No. 63/589,691, filed on Oct. 12, 2023.

(51) Int. Cl.
| | | |
|---|---|---|
| *A61K 9/1271* | (2025.01) | |
| *A61K 9/51* | (2006.01) | |
| *A61K 31/7105* | (2006.01) | |
| *A61K 31/711* | (2006.01) | |
| *C12N 15/113* | (2010.01) | |

(52) U.S. Cl.
CPC .......... *A61K 9/1271* (2013.01); *A61K 9/5123* (2013.01); *A61K 31/7105* (2013.01); *A61K 31/711* (2013.01); *C12N 15/113* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 2015/0374842 A1* | 12/2015 | Brown | ............ | A61K 9/1271 536/24.5 |
| 2024/0166593 A1* | 5/2024 | Ramishetti | ............ | C07C 239/18 |
| 2024/0252617 A1* | 8/2024 | Saunders | ............ | C07K 14/005 |

FOREIGN PATENT DOCUMENTS

| | | | | |
|---|---|---|---|---|
| WO | WO 2021/148511 A1 | | 7/2021 | |
| WO | WO-2023043933 A1 * | | 3/2023 | ............ A61K 9/0021 |

OTHER PUBLICATIONS

Center for Drug Evaluation and Research, Product Quality Review(s), https://www.accessdata.fda.gov/drugsatfda_docs/nda/2018/210922Orig1s000ChemR.pdf.
Daniel et al., "Quality by Design for enabling RNA platform production processes", *Trends in Biotechnology* 40(10):1213-1228 (2022).
Felgner et al., "Lipofection: a highly efficient, lipid-mediated DNA-transfection procedure", *PNAS USA* 84(21):7413-7174 (1987).
Felgner et al., "Enhanced Gene Delivery and Mechanism Studies with a Novel Series of Cationic Lipid Formulations", *Journal of Biological Chemistry* 269(4):2550-2561 (1994).
Heyes et al., "Cationic lipid saturation influences intracellular delivery of encapsulated nucleic acids", *Journal of Controlled Release* 107(2):276-287 (2005).
Hou et al., "Lipid nanoparticles for mRNA delivery", *Nature Reviews Materials* 6:1078-1094 (2021).
Huang et al., "The landscape of mRNA nanomedicine", *Nature Medicine* 28:2273-2287 (2022).
Jayaraman et al., "Maximizing the Potency of siRNA Lipid Nanoparticles for Hepatic Gene Silencing In Vivo", *Angewandte Chemie International Edition* 51:8529-8533 (2012).
Kim, "Rna therapy: rich history, various applications and unlimited future prospects", *Experimental & Molecular Medicine* 54:455-465 (2022).
Morille et al., "Progress in Developing Cationic Vectors for Non-Viral Systemic Gene Therapy against Cancer", *Biomaterials* 29(24-25):3477-3496 (2008).
Sahin et al., "mRNA-based therapeutics—developing a new class of drugs", *Nature Reviews Drug Discovery* 13:759-780 (2014).
Xu et al., "Mechanism of DNA Release from Cationic Liposome/DNA Complexes Used in Cell Transfection", *Biochemistry* 35(18):5616-5623 (1996).
Yuba et al., "Effect of Unsaturated Alkyl Chains on Transfection Activity of Poly(Amidoamine) Dendron-Bearing Lipids", *Journal of Controlled Release* 160(3):552-560 (2012).
Cheng et al., "The role of helper lipids in lipid nanoparticles (LNPs) designed for oligonucleotide delivery", *Advanced Drug Delivery Reviews* 99:129-137 (2016).
International Search Report and Written Opinion for International Application No. PCT/US2024/050921 mailed Feb. 26, 2025, 10 pages.
Zaborova et al., "Solid Lipid Nanoparticles for the Nucleic Acid Encapsulation", *Reviews and Advances in Chemistry* 11:178-188 (2021).

* cited by examiner

*Primary Examiner* — Celeste A Roney
(74) *Attorney, Agent, or Firm* — LATHROP GPM LLP; Brian C. Trinque; Nicole Sassu

(57) ABSTRACT

The present disclosure relates to lipid nanoparticles and methods of delivering active agents to target organs, tissues, or cells by utilizing the lipid nanoparticles.

13 Claims, 39 Drawing Sheets

Figure 1

An Exemplary Composition of the LNP-1 Lipid Nanoparticle Platform: Structural Lipid Components

| Lipid Components (LNP1) | Lipid Component & Formula | Mw (g/mol) | Exact Mass (g/mol) |
|---|---|---|---|
| DODMA (18:1) | $C_{42}H_{80}NO_2$ | 620.10 | 620.63 |
| L1A (18:1) | $C_{15}H_{29}NO_{10}P$ | ~2839.57 (Average) | ~2837.79 (Average) |
| DSPC (18:0) | $C_{44}H_{88}NO_8P$ | 790.16 | 789.62 |
| Cholesterol | $C_{27}H_{46}O$ | 386.66 | 386.35 |

Drug Product Formulation Buffer Solution pH 7.4 ± 0.2, -18.7 ± 0.8 mV at 25°C (Exemplary):
- Sodium Phosphate Dibasic: 10.14 mM
- Potassium Phosphate Monobasic: 1.76 mM
- Potassium Chloride: 2.7 mM
- Sodium Chloride: 137 mM
- Nuclease-Free Water, not DEPC-Treated

Figure 2

Lipid Composition of the LNP-1 Platform (Exemplary)

| Sample | Lipid Name | Calculated Concentration (mg/ml) | LNP Total Mass (mg/ml) | MW | mmol in 1ml | Total Count (mmol) | Assay mmol% | Assay m/m% |
|---|---|---|---|---|---|---|---|---|
| eGFP mRNA/LNP-1 (Freshly-formulated) | DODMA | 3.254 | 6.448 | 620.10 | 0.0005830 | 0.001256 | 46.41 | 50.46 |
| | DSPC | 1.024 | | 790.15 | 0.0001440 | | 11.46 | 15.88 |
| | Cholesterol | 1.802 | | 386.65 | 0.0005191 | | 41.33 | 27.94 |
| | L3A | 0.245 | | 2841.00 | 0.0000096 | | 0.76 | 3.80 |

Identity of LNP-1 Formulations: Four Lipid Components
Separation of Four Lipid Components of LNP-1 Formulations Obtained by UPLC-ELSD Method

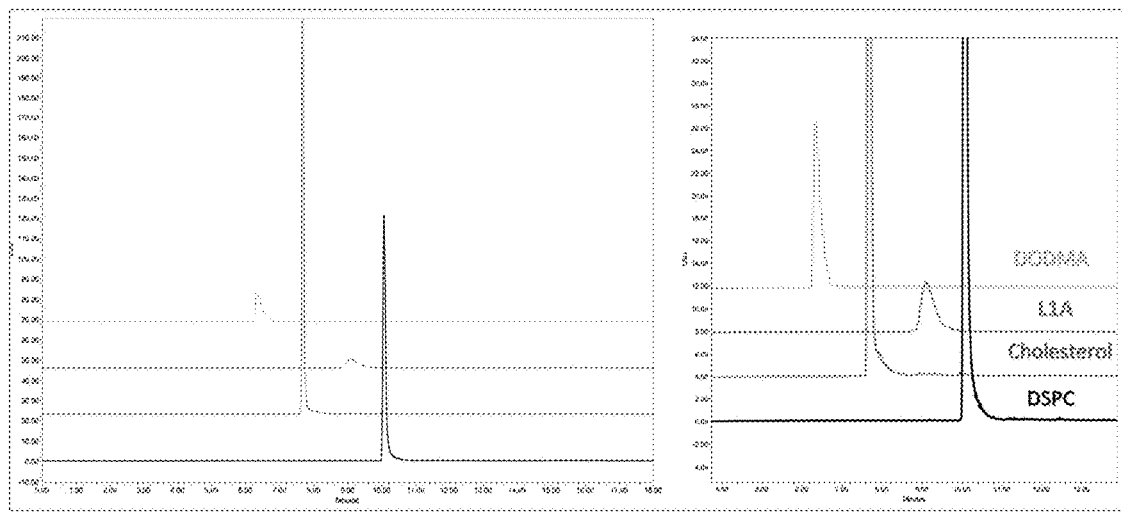

Figure 3 (Cont.)
Confirmation of PEGylated L1A Synthesis
Thin-Layer Chromatography (TLC) Plate
UV wavelength = 254 nm
After working the Rxn MIX out
3 solvents mixture for Mobile phase were used to run TLC Plate
(CHCl3:CH3OH:H2O, 100:10:2)
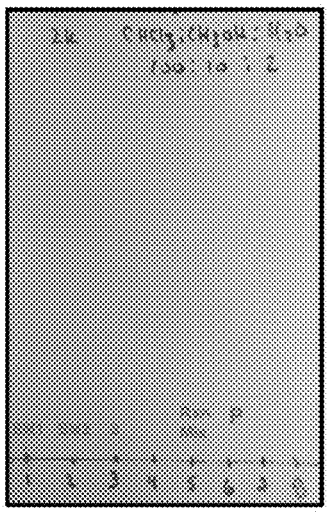  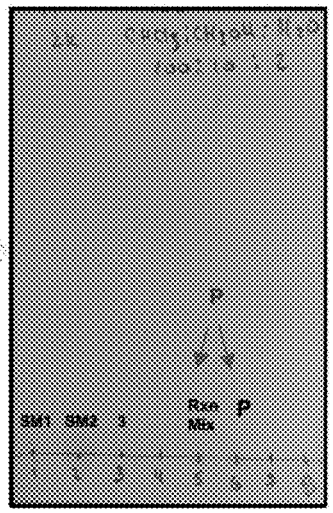  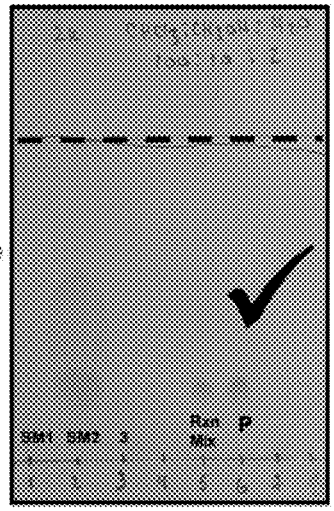
Rxn Mix: SM1 + SM2 + 3 + P
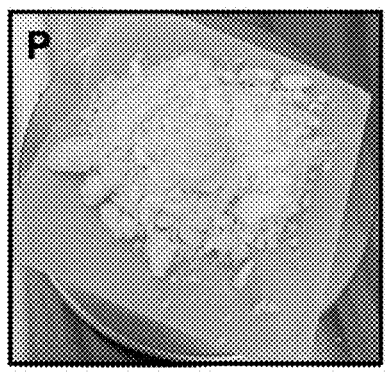
PEGylated L1A (Lyophilized Powder at -80°C)

Identity, Purity and Integrity Confirmation of PEGylated L1A
PEGylated L1A Successfully Identified, Integrity Confirmed with No Impurity
Identity of PEGylated L1A: Proton $^1$H NMR

High Compatibility of PEG-conjugated Phospholipid of LNP-1 (Exemplary)
LNP-1's Flexibility with Structural Ionizable Lipid Component (Exemplary)

Figure 4 (Cont.)
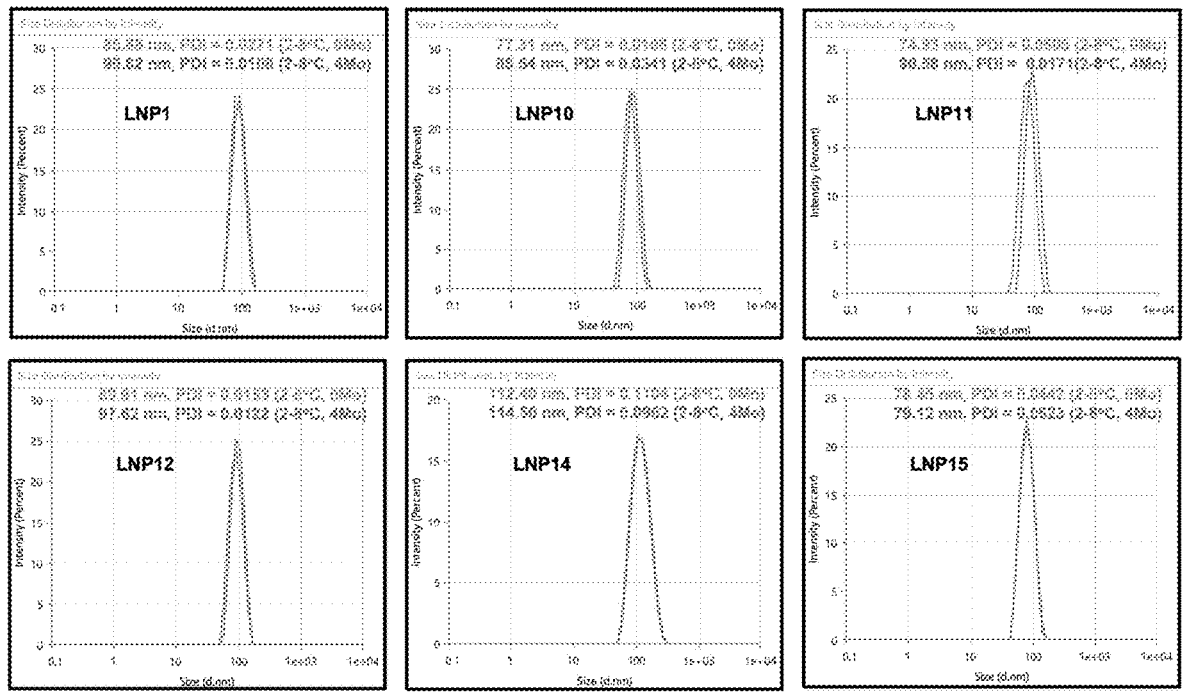
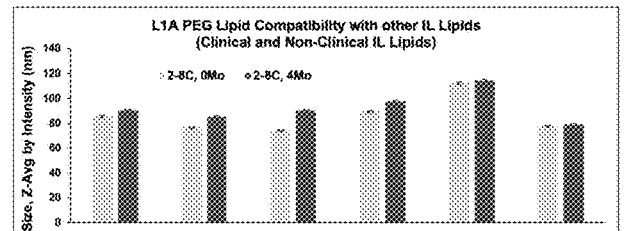
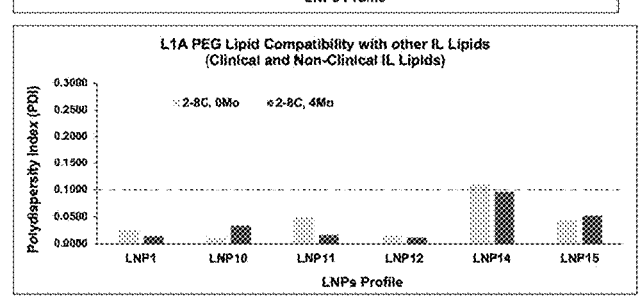

Flexibility with Four Lipid Component Molar Ratios of LNP-1 (Exemplary)

| LNP ID | DODMA | DSPC | Cholesterol | PEGylated L1A |
|---|---|---|---|---|
| LNP-V1 | 59.25 | 10 | 30 | 0.75 |
| LNP-V2 | 50 | 10 | 38 | 2 |
| LNP-V3 | 50 | 10 | 35 | 5 |
| LNP1 | 50 | 10 | 39.25 | 0.75 |
| LNP-V5 | 55 | 5 | 39.25 | 0.75 |
| LNP-V6 | 10 | 50 | 39.25 | 0.75 |
| LNP-V7 | 5 | 55 | 39.25 | 0.75 |
| LNP-V8 | 30 | 10 | 59.25 | 0.75 |

Figure 5 (Cont.)
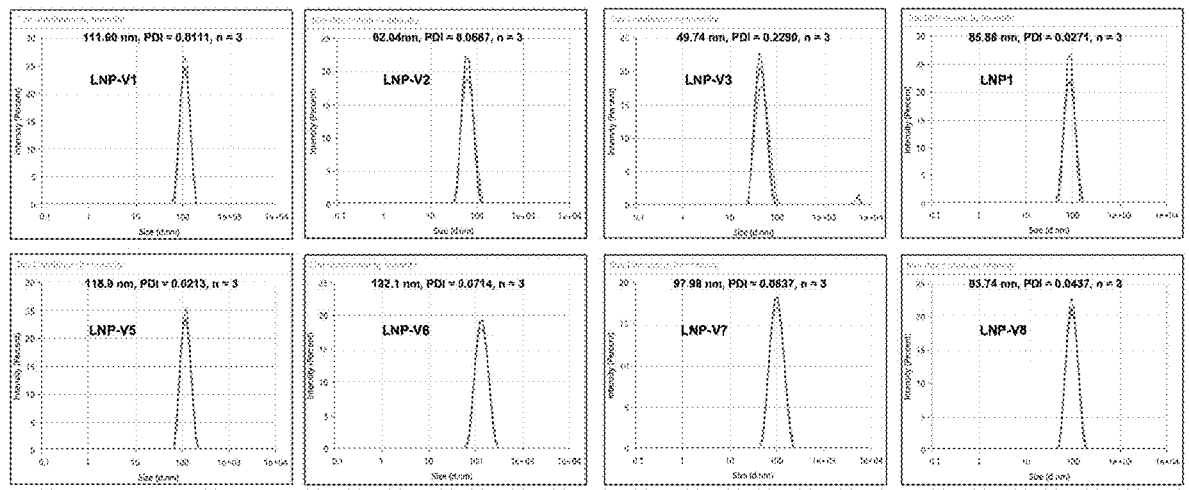
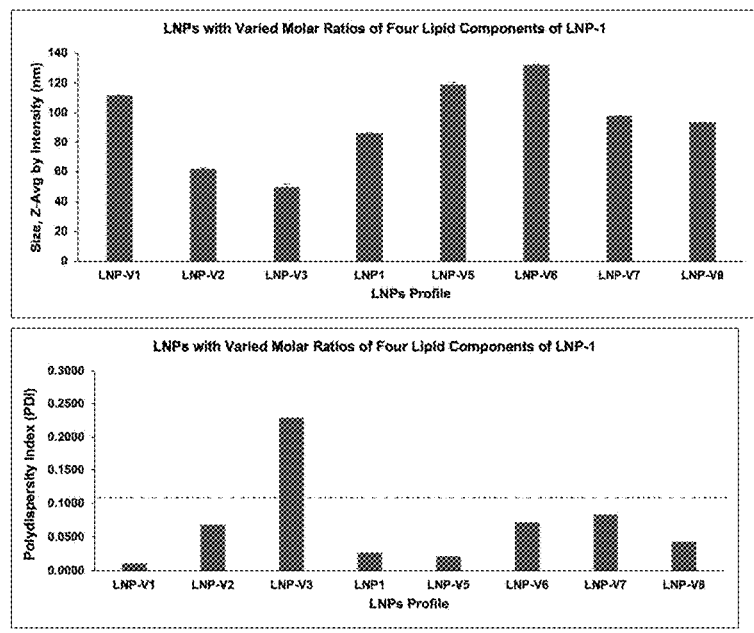

Figure 7
RNA Payload Assay for LNP-1 LNPs Formulations
Fluorescent Quant-iT RNA RiboGreen Quantification Method (Exemplary)
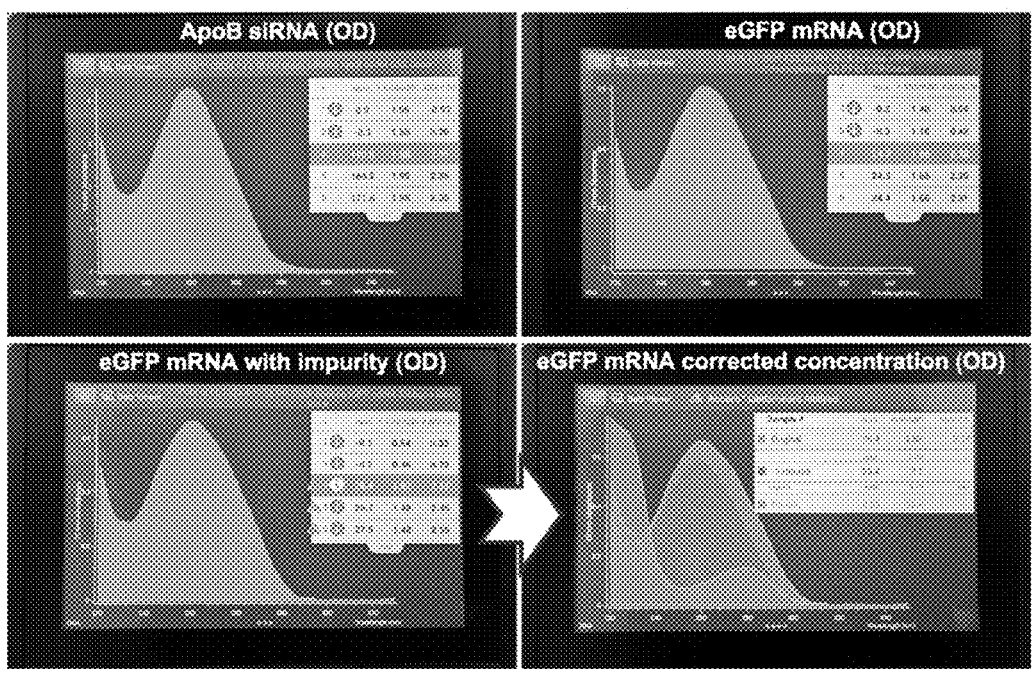
OD measurements by NanoDrop One from Thermo Fisher Scientific (Exemplary)
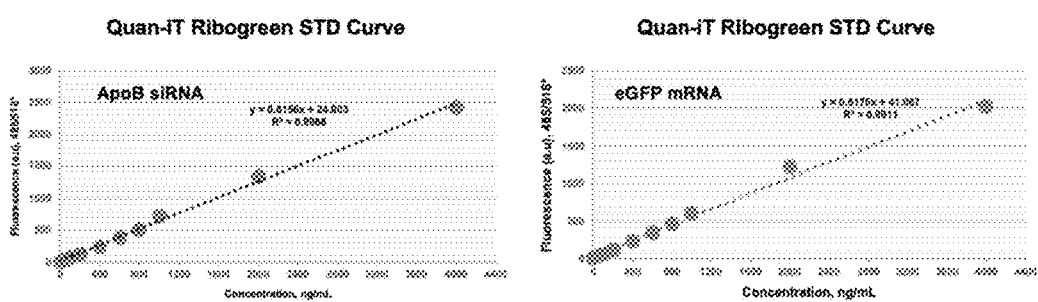
Fluorescent Quant-iT RNA RiboGreen Quantification Method STD Curve (Exemplary)

Figure 7 (Cont.)

1. Quantify a stock solution (e.g. 20-1000ng/uL) by OD (Optical Density) at $A_{260}$, $A_{280}$, $A_{260}/A_{280}$ and $A_{260}/A_{230}$, see NanoDrop One exemplary spectra data images. Note: Apply a corrected RNA concentration if any impurity is present in the RNA samples, specifically for mRNAs, as shown on spectra data image.
2. Prepare in a fluorescent microplate assay (96-well plate) a series of diluted concentrations from the above RNA stock solution for building a Standard Curve (e.g. 0-2000+ng/mL). Add as well LNPs-RNAs stock solution as control, disassembled LNP-RNA samples from stock solution and/or other control samples in the black clear bottom microplate. Note: Disassembled LNP-RNA samples are incubated at 5% (v/v) TX-100 in TE Buffer (1x) at 50°C for 2h, then diluted at a final 0.1% (v/v) TX-100 concentration in TE Buffer (1x).
3. Ultrasensitive Fluorescent Quan-iT RNA Ribogreen Quantification Method is performed to all RNAs samples e.g. Standard Curve (STD as shown on plots images) vs LNPs-RNAs control vs disassembled LNP-RNA samples vs other control samples according to vendor protocol. Note: Take into consideration any effect of common contaminants for this ultrasensitive fluorescent assay, see link:
https://assets.thermofisher.com/TFS-Assets/LSG/manuals/mp11490.pdf

Structural & Functional Stable L1A PEG-lipid is Compatible with Other Ionizable Lipids Having Smaller Sizes

| CODE ID | Size (nm) | | SD | | PDI | | SD | |
|---|---|---|---|---|---|---|---|---|
| | 0Mo | 4Mo | 0Mo | 4Mo | 0Mo | 4Mo | 0Mo | 4Mo |
| #1 | 85.88 | 90.24 | 0.7063 | 0.4313 | 0.0271 | 0.0302 | 0.0216 | 0.0057 |
| #2 | 112.80 | 119.30 | 0.7798 | 1.3360 | 0.0180 | 0.0070 | 0.0162 | 0.0040 |
| #3 | 89.91 | 97.62 | 0.3958 | 0.9909 | 0.0153 | 0.0122 | 0.0177 | 0.0089 |
| #4 | 132.60 | 133.20 | 1.3930 | 1.9950 | 0.0234 | 0.0144 | 0.0130 | 0.0045 |

1: (LNP-1 LNP): DODMA + L1A PEG
2: DODMA + PEG(2K)-DMG
3: DLin-MC3-DMA + L1A PEG
4: (Alnylam/Onpattro LNP): DLin-MC3-DMA + PEG(2K)-DMG + DSPC + Cholesterol

Figure 10

**Long-term Structural Lipids Stability and Quantification
– Stable Lipid Composition of Aged eGFP mRNA/LNP-1**

| Sample | Lipid Name | Calculated Concentration (mg/ml) | LNP Total Mass (mg/ml) | MW | mmol in 1ml | Total Count (mmol) | Assay mmol% | Assay m/m% |
|---|---|---|---|---|---|---|---|---|
| eGFP mRNA/LNP-1 (Freshly-formulated) | DODMA | 3.254 | 6.448 | 620.10 | 0.0005830 | 0.001256 | 46.41 | 50.46 |
| | DSPC | 1.024 | | 790.15 | 0.0001440 | | 11.46 | 15.88 |
| | Cholesterol | 1.802 | | 385.65 | 0.0005191 | | 41.33 | 27.94 |
| | L1A | 0.245 | | 2841.00 | 0.0000096 | | 0.76 | 3.80 |

| Sample | Lipid Name | Calculated Concentration (mg/ml) | LNP Total Mass (mg/ml) | MW | mmol in 1ml | Total Count (mmol) | Assay mmol% | Assay m/m% |
|---|---|---|---|---|---|---|---|---|
| eGFP mRNA/LNP-1 (2-8°C, 9 Months Storage) | DODMA | 2.720 | 5.547 | 620.10 | 0.00048745 | 0.001135 | 42.94 | 49.04 |
| | DSPC | 0.687 | | 790.15 | 0.00009665 | | 8.51 | 12.39 |
| | Cholesterol | 1.891 | | 385.65 | 0.00054876 | | 47.98 | 34.09 |
| | L1A | 0.157 | | 2841.00 | 0.00000615 | | 0.54 | 2.84 |

Long-term Physicochemical Stability of Aged LNP-1 with Different RNA Payloads

Physical Characterization of Critical Quality Attributes Summary (25°C) (ApoB siRNA/LNP-1)

| Days | Size Zavg ± SD (nm) | PDI ± SD | Average Charge Zeta Potential ± SD (mV) | Average Conductivity |
|---|---|---|---|---|
| 0 | 91.34 ± 0.2126 | 0.0160 ± 0.0012 | | |
| 7 | 90.73 ± 0.8719 | 0.0363 ± 0.0132 | | |
| 28 | 90.65 ± 0.5808 | 0.0121 ± 0.0114 | | |
| 56 | 93.45 ± 0.1841 | 0.0313 ± 0.0140 | | |
| 84 | 96.65 ± 1.218 | 0.0589 ± 0.0107 | -26.9097 ± 7.1642 | 0.3802 ± 0.1530 |
| 112 | 98.65 ± 0.2878 | 0.0716 ± 0.0183 | | |
| 140 | 102.9 ± 0.9965 | 0.0793 ± 0.0440 | | |
| 168 | 101.5 ± 0.6061 | 0.0699 ± 0.0096 | | |
| 189 | 103.2 ± 0.6065 | 0.0836 ± 0.0111 | | |

Figure 14
Long-term Stability of ApoB siRNA/LNP-1 at 40°C
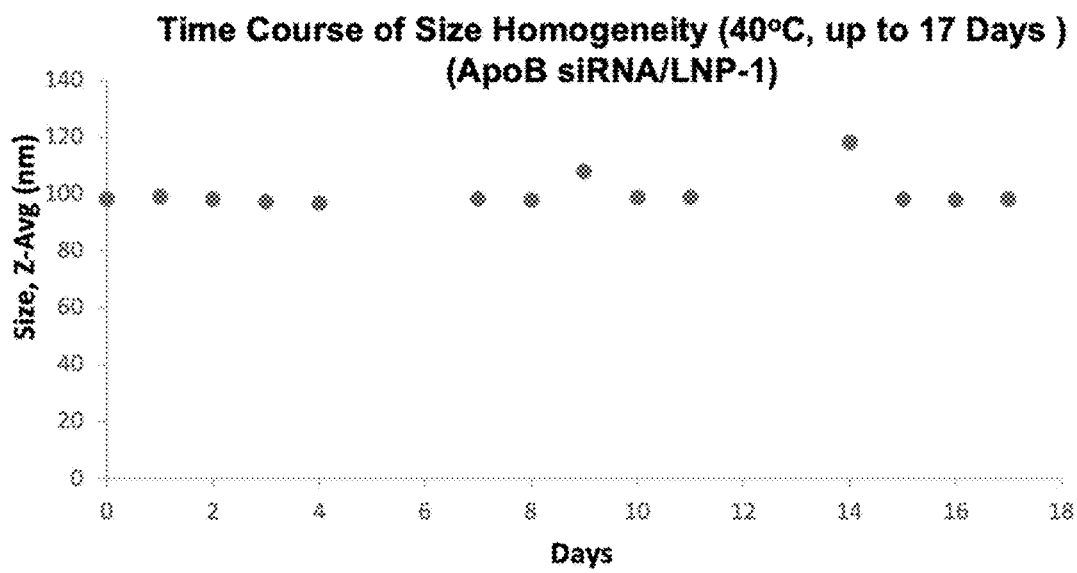
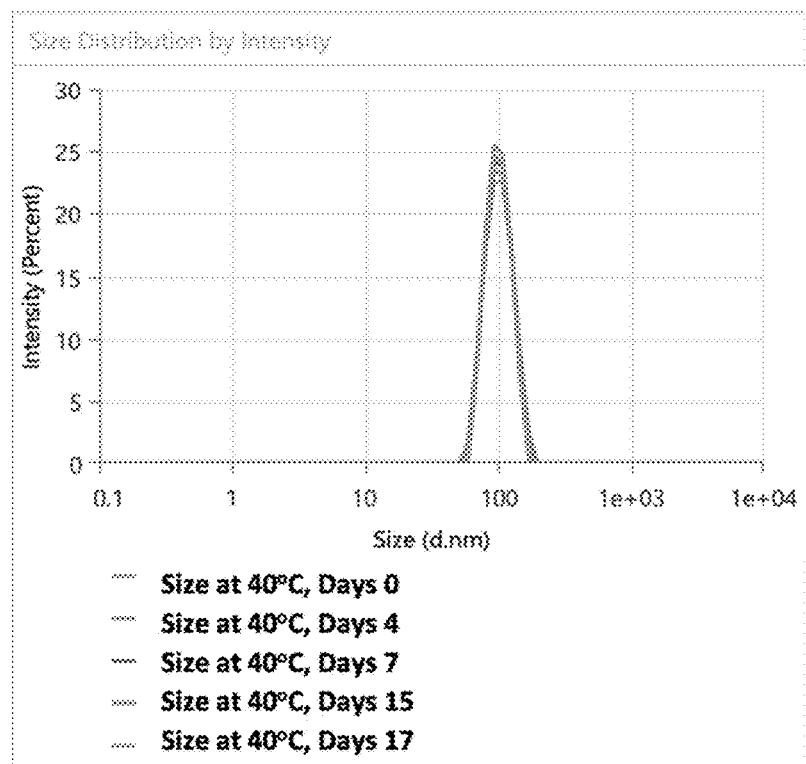

Long-term Morphology and Topology Stability of Aged LNP-1 with Different RNA Payloads

Figure 16

LNP-1 Platform Characterization Summary:
Payloads Versatility and Long-term Stability

| Payload Type | Payload Size (nt) | Encapsulation Efficiency | RNA/LNP-1 Size (nm) | Long-term Stability (2-8°C) | | |
|---|---|---|---|---|---|---|
| ApoB siRNA | 21 (ds) | >94% | 90 ± 10 | 12Months | PDI | 0.0515 |
| | | | | | Zeta Potential (mV) | 35.02 ± 0.6746 |
| eGFP mRNA | 980 (ss) | >87% | 117 ± 10 | 9Months | PDI | 0.0366 |
| | | | | | Zeta Potential (mV) | 32.66 ± 1.234 |
| PAH mRNA | 1619 (ss) | >69% | 129 ± 10 | 7Months | PDI | 0.0411 |
| | | | | | Zeta Potential (mV) | 32.89 ± 1.743 |
| F9 mRNA | 1646 (ss) | >65% | 125 ± 10 | 7Months | PDI | 0.0734 |
| | | | | | Zeta Potential (mV) | 34.75 ± 1.065 |
| Cas9 mRNA/sgRNA | 4471/100 (ss/ss) | >80%/>90% | 125 ± 10 | 3Months | PDI | 0.0359 |
| | | | | | Zeta Potential (mV) | 36.32 ± 0.5806 | ds: Double-Stranded
ss: Single-Stranded

Long-term Function Stability – Stable CAR-T Generation Potency of Aged eGFP mRNA/LNP-1

Long-term Function Stability – Stable Gene Delivery Potency of Aged eGFP mRNA/LNP-1

Long-term Function Stability – Stable CRISPR Knockout Potency of Aged Cas9 mRNA + TRAC sgRNA/LNP-1

Long-term Function Stability – Stable Gene Silencing Potency of Aged ApoB siRNA/LNP-1

Figure 21
LNP-1's Versatile Therapeutic Applications – Gene Silencing
In Vivo Knockdown Potency of ApoB siRNA/LNP-1 in Mouse Livers
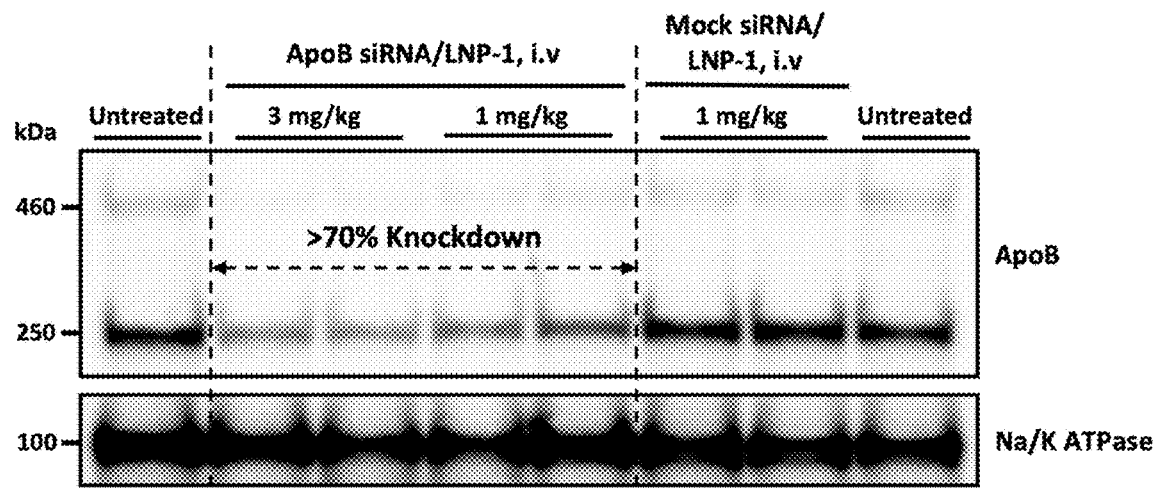
ApoB siRNA/LNP-1 In Vivo Potency at Different Dosages
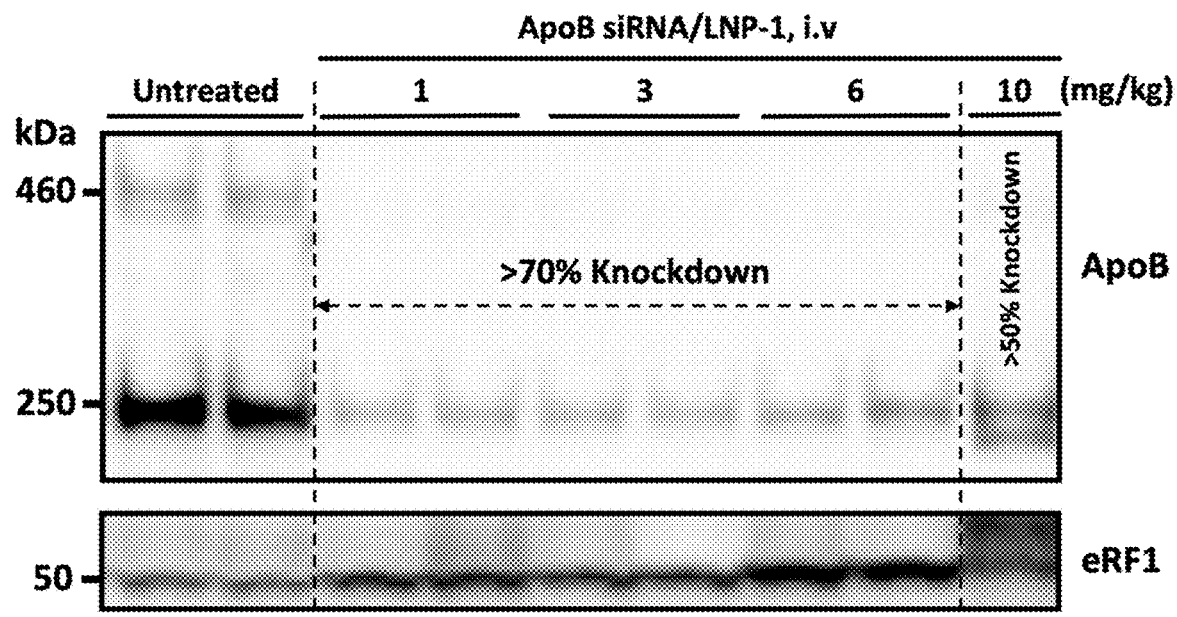
Note: No abnormality in biochemistry profiles was detected in 1-3 mg/kg treated mice.

Batch Consistency of Stable ApoB siRNA/LNP-1:
Western Blotting of Liver Tissues from Mice Received 1 mg/kg (i.v) ApoB siRNA/LNP-1

LNP-1's Versatile Therapeutic Applications – Chimeric Antigen Receptor (CAR) Expression

Ex Vivo Gene Delivery Potency of LNP-1 (Exemplary)

LNP-1's Versatile Therapeutic Applications – Ex Vivo CAR-T Cell Engineering

Ex Vivo CAR-T Generation Potency of LNP-1 (Exemplary)

LNP-1's Versatile Therapeutic Applications – In Vivo CAR-T Cell Engineering

In Vivo CAR-T Generation Potency of LNP-1 (Exemplary)

LNP-1's Versatile Therapeutic Applications – Stem Cell Engineering

Gene Delivery Potency of LNP-1 to Hematopoietic Stem Cells (Exemplary)

Figure 29
LNP-1's Versatile Therapeutic Applications – Gene Therapy for Malignant Cells
Gene Delivery Potency of LNP-1 to Human Leukemia Cells (Exemplary)
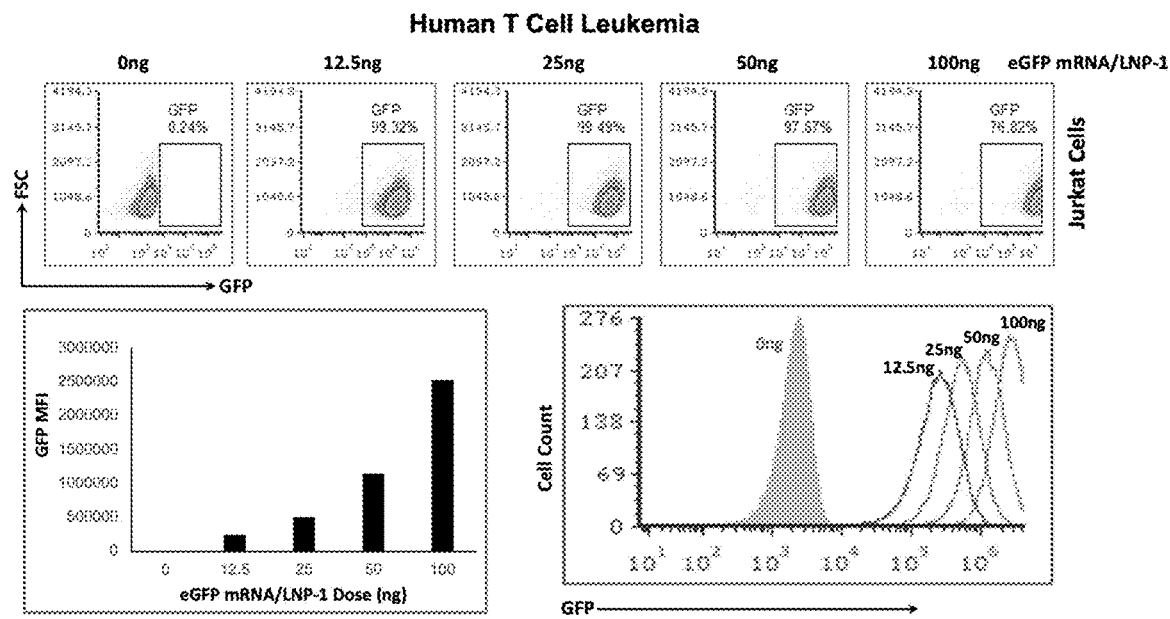
Persistent GFP Signal by LNP-1 Delivery
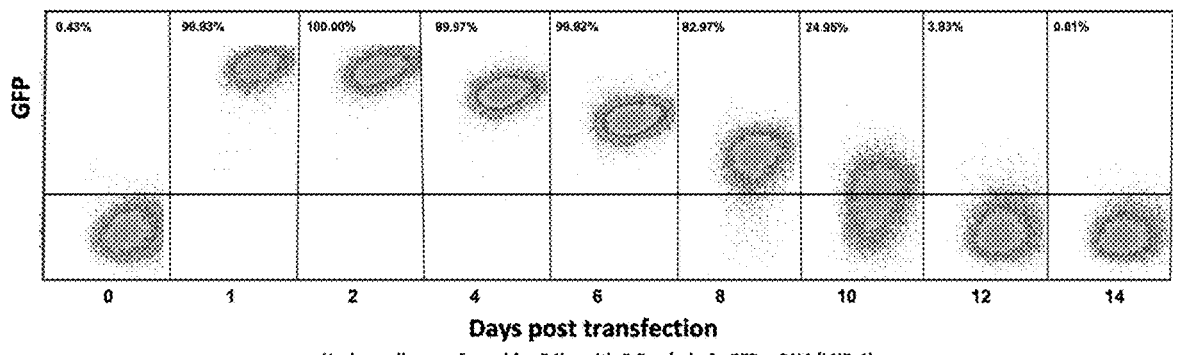
(Jurkat cells transfected for 24hr with 0.5ug/ml of eGFP mRNA/LNP-1)
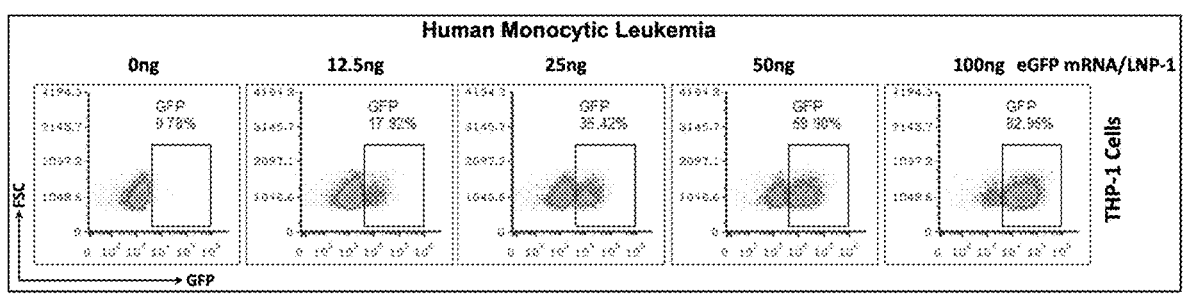

Figure 30

LNP-1's Versatile Therapeutic Applications – Gene Therapy for Malignant Cells

Gene Delivery Potency of LNP-1 to Human Lymphoma Cells (Exemplary)

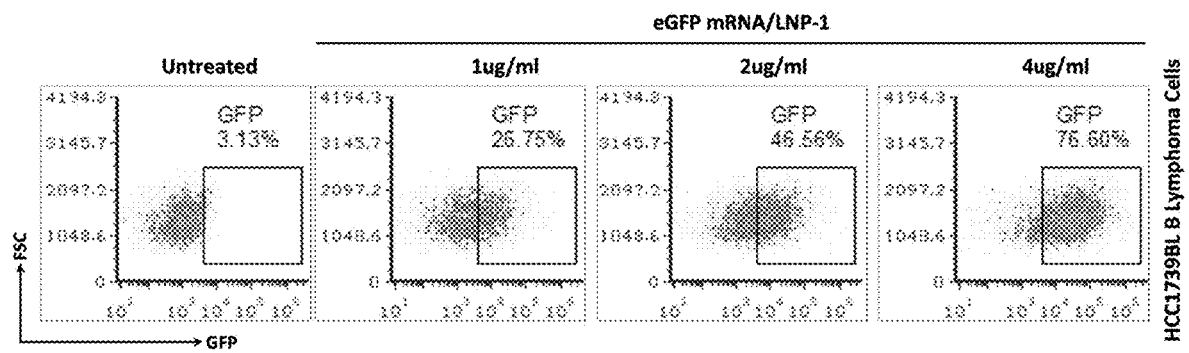

Figure 31

LNP-1's Versatile Therapeutic Applications – Gene Therapy for Cancer Cells

Gene Delivery Potency of LNP-1 to Human Cancer Cells (Exemplary)

Human Liver Cancer Cells

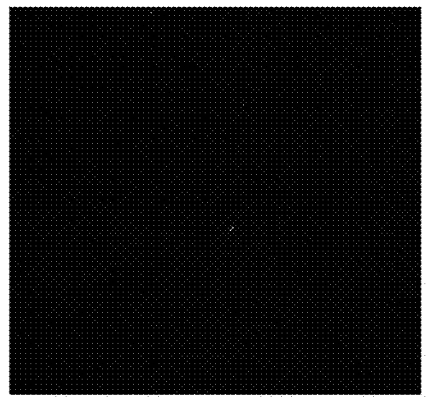 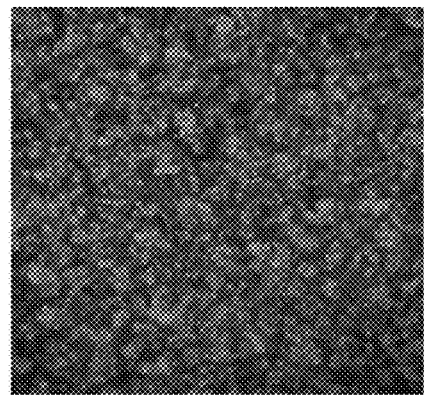

Note: GFP signal is persistent up to the study termination (day 7).

Figure 32
LNP-1's Versatile Therapeutic Applications – Vaccines
LNP-1's Potency as COVID-19 mRNA Vaccines (Exemplary)
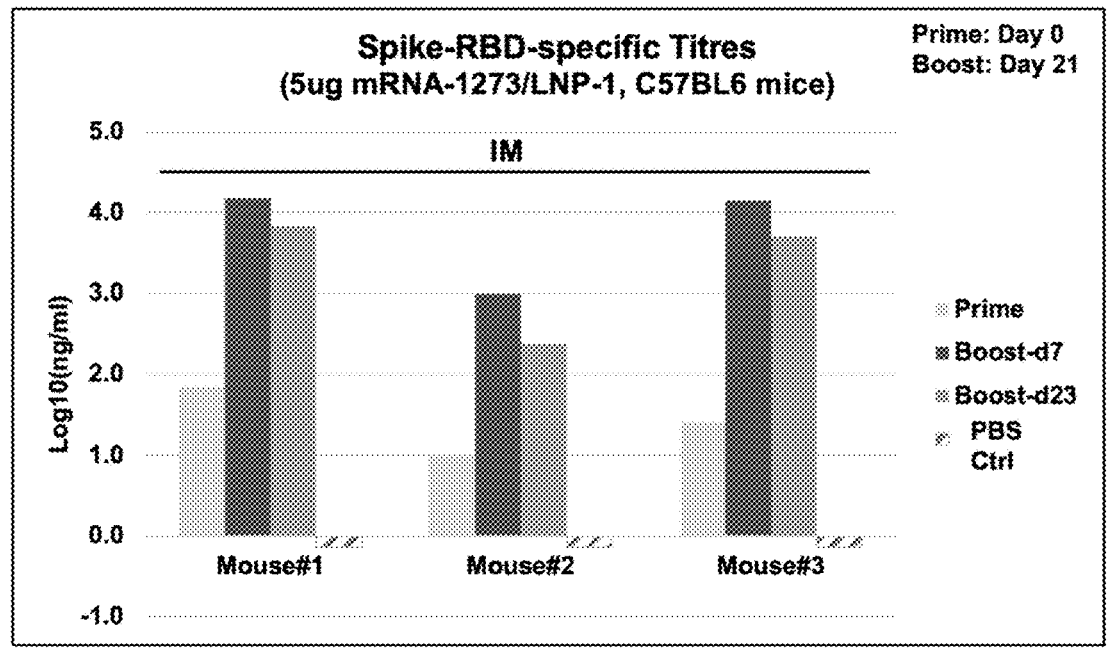
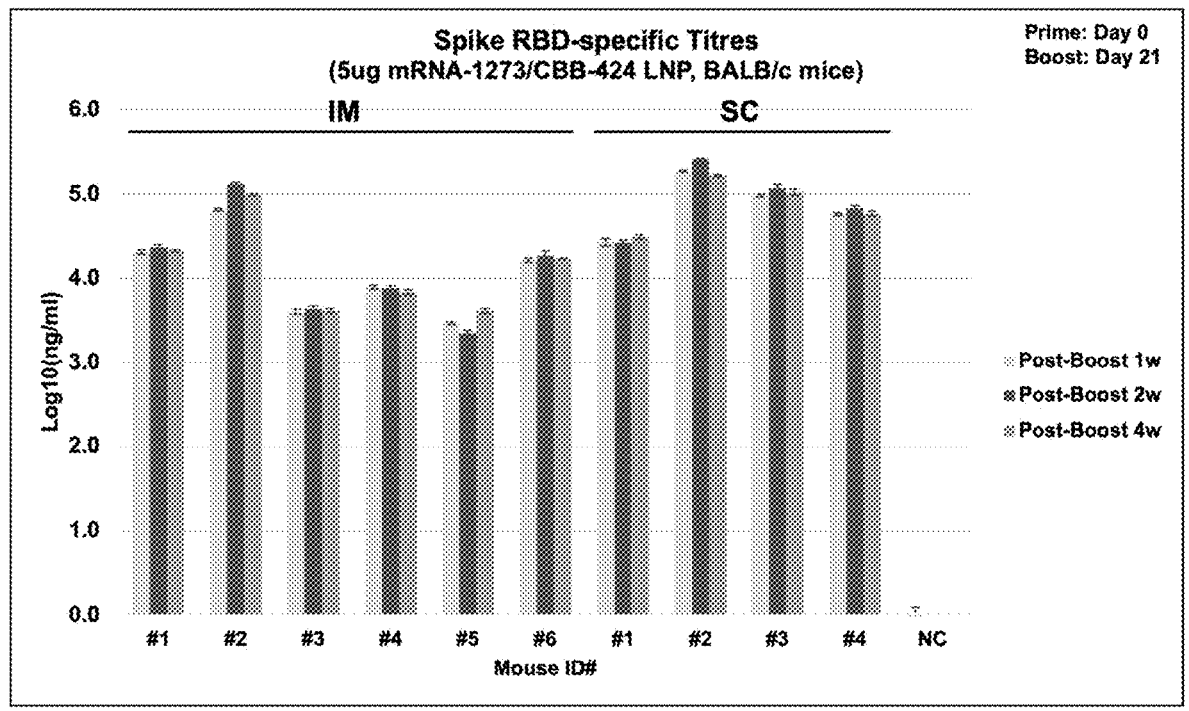

Figure 33
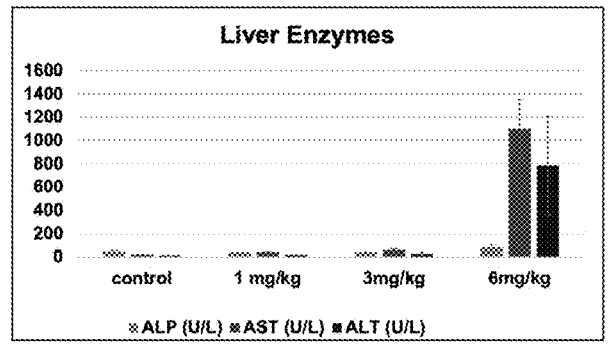
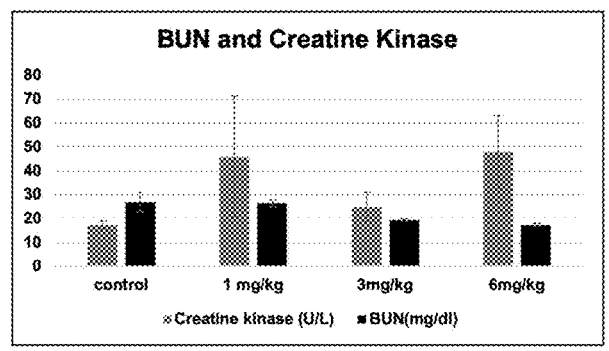
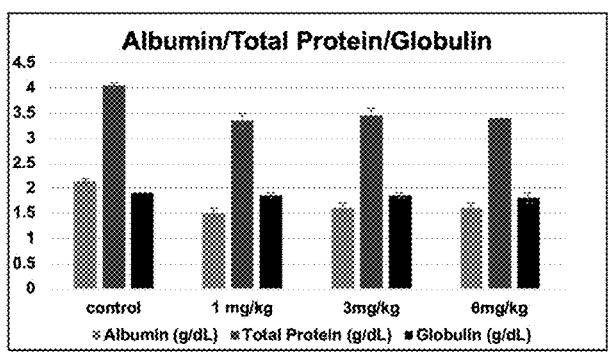
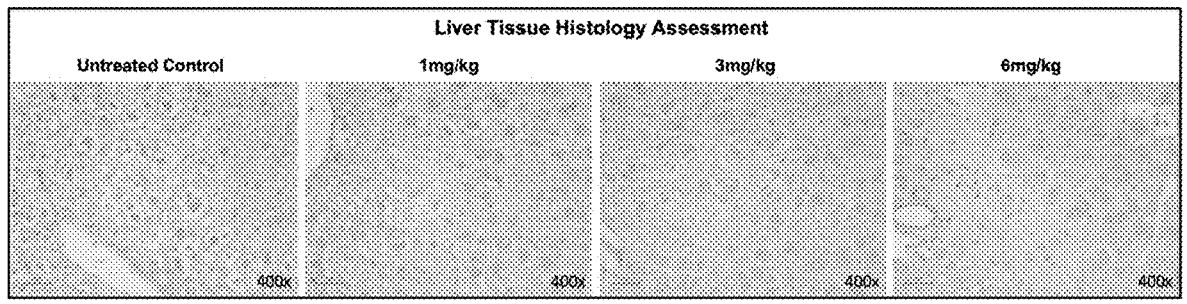

LIPID NANOPARTICLES

RELATED APPLICATIONS

This application claims priority to U.S. Provisional Application No. 63/589,691, filed Oct. 12, 2023, and U.S. Provisional Application No. 63/589,693, filed Oct. 12, 2023, the content of both is incorporated by reference in its entirety.

BACKGROUND

Conventional therapies using small molecules or antibodies transiently target disease-related proteins. Such treatments may mitigate the symptoms of illness, but often leave the underlying cause to perpetuate. In their wake, nucleic acids have arisen as a popular form of therapeutics and prophylactics. As they can regulate gene expression and target specific codes, nucleic acid-based drugs can treat diseases such as viral infections, genetic disorders, and cancer by attacking them at the root. Such treatment promises to provide thorough and potentially permanent relief.

At the core of dozens of drugs, particularly nucleic acid-based drugs, are molecules that contain ionic residues and are highly hydrophilic, which precludes them from entering cells, their obligate therapeutic environment. If left in the blood, naked therapeutics are cleared via the kidneys and the liver. Thus, one of the most important issues facing nucleic acid drugs is delivery and targeting.

To achieve the appropriate chemistry to prevent sequestration, opsonization, immunoresponse and clearance, as well as promote payload carrying, delivery capacities, and entry into the cell, lipid nanoparticles can be employed to encapsulate therapeutic agents. Lipid nanoparticles are a type of drug carrier and delivery system mimicking biological spherical vesicles comprised of a mixture of functional lipids. By incorporating other molecules to create a heterogeneous composition, lipid nanoparticles can be designed to direct therapeutic agents to the proper target organ, tissue, and/or cell. Once at the location of interest, the amphipathic nature of lipid nanoparticles shields the hydrophilicity of the therapeutic payload thus allowing it to enter and be delivered to the cell type of interest.

Lipid nanoparticles also protect the payload from degradation. As molecules pass through the cell membrane, they are enveloped in a layer of membrane creating endosomes, that can be directed to the lysosome for degradation. To prevent the digestion of the therapeutic agent, the lipid nanoparticle can induce the destruction of the endosome prior to its integration with the lysosome, thus safely releasing the payload into the cytosol. By protecting the payload from destruction, lower doses of drugs can be administered with similar or even better therapeutic results than naked therapeutic agents.

Though the development of lipid nanoparticles has come a long way, there remains a need for structures that carry, protect, target, and release new and improving therapeutic agents.

SUMMARY

Provided herein is a lipid nanoparticle comprising:
(i) a PEG-conjugated phospholipid (PEG-phospholipid) having two or more $C_{12}$-$C_{30}$ aliphatic chains, at least one of which includes from 1-5 sites of unsaturation;
(ii) an ionizable lipid having at least two $C_{11}$-$C_{30}$ aliphatic chains and a head group that protonates to a cationic moiety having a pKa of 5-7;
(iii) a non-cationic phospholipid having at least two $C_{11}$-$C_{30}$ aliphatic chains and a head group that remains a zwitterion or anion across a pH range of 6 to 8; and
(iv) a sterol, fat-soluble steroid, or vitamin.
In an embodiment, (iv) is cholesterol.
In an embodiment, the lipid nanoparticle comprises

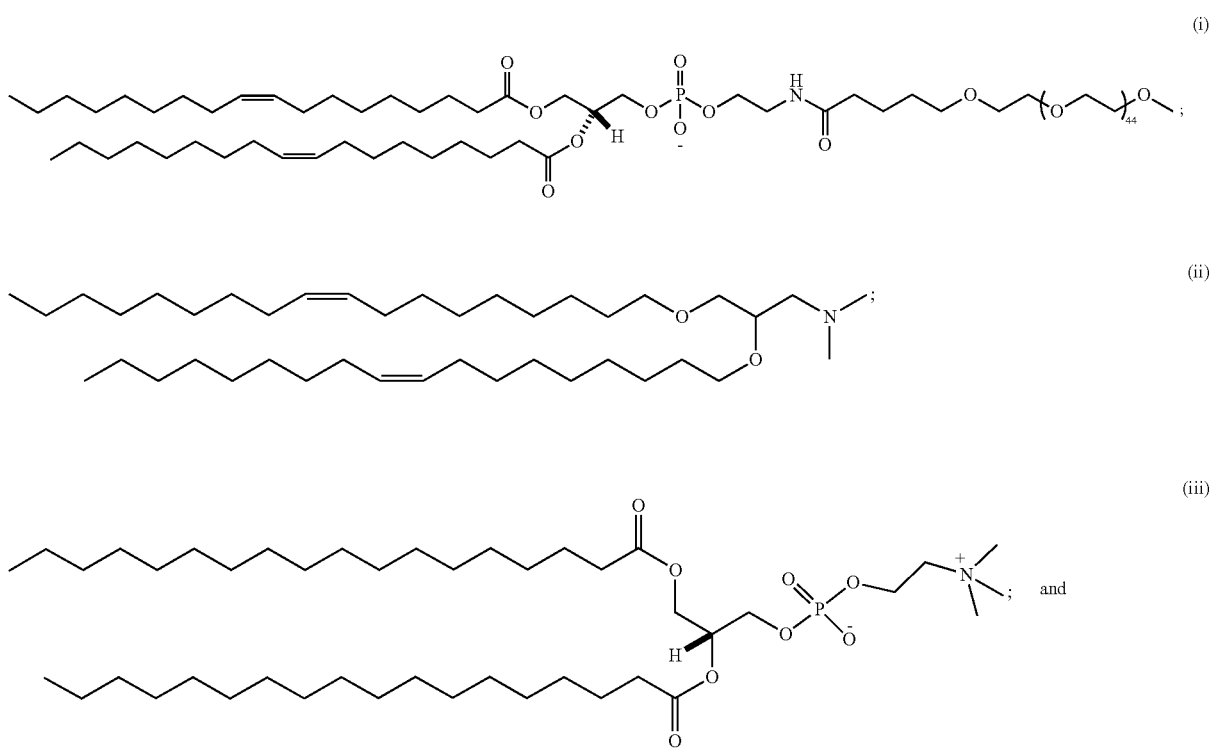

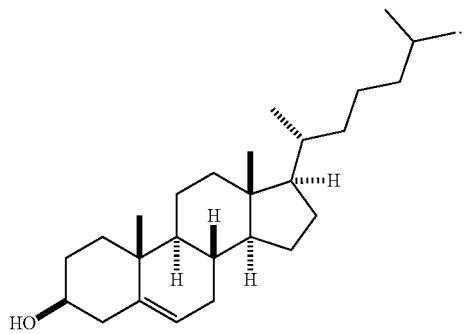

(iv)

This lipid nanoparticle is also referred to herein as "LNP-1."

The lipid nanoparticles of the present disclosure are useful in transporting active agents across lipid membranes to deliver the active agent to the target tissue, organ, or cell.

BRIEF DESCRIPTION OF FIGURES

FIG. 1 shows an embodiment of the LNP-1 platform technology.

FIG. 2 shows the lipid composition of LNP-1 formulations as confirmed at the expected values and for four lipid components' identity.

FIG. 7 shows RNA payload quantification method for LNP-1 LNPs formulations.

FIG. 10 shows that eGFP mRNA/LNP-1s are stable for long-term storage at 2-8° C.—the structural lipid composition and total LNP content of 9 months old formulations are comparable to that of freshly-formulated.

FIG. 14 shows that ApoB siRNA/LNP-1s are stable for long-term storage at 40° C.

FIG. 16 summarizes the payloads versatility and long-term stability of LNP-1 technology platform, which can encapsulate varied types and sizes of nucleic acids and remain stable for long-term storage at 2-8° C.

FIG. 21 shows LNP-1's potency using siRNA targeting mouse ApoB as the payload.

FIG. 29 shows LNP-1's potency delivering eGFP mRNA to human leukemia cells with persistent protein expression.

FIG. 30 shows LNP-1's potency delivering eGFP mRNA to human lymphoma cells.

FIG. 31 shows LNP-1's potency delivering eGFP mRNA to human cancer cells with persistent protein expression.

FIG. 32 shows LNP-1's potency as vaccines, e.g., COVID-19 mRNA vaccines via intramuscular (IM) or subcutaneous (SC) delivery of Spike mRNA.

FIG. 33 shows that, within the therapeutic window (e.g., 0.1-3 mg/kg), no in vivo toxicity is noted with LNP-1 formulations via i.v administration.

DETAILED DESCRIPTION

Figure 3:
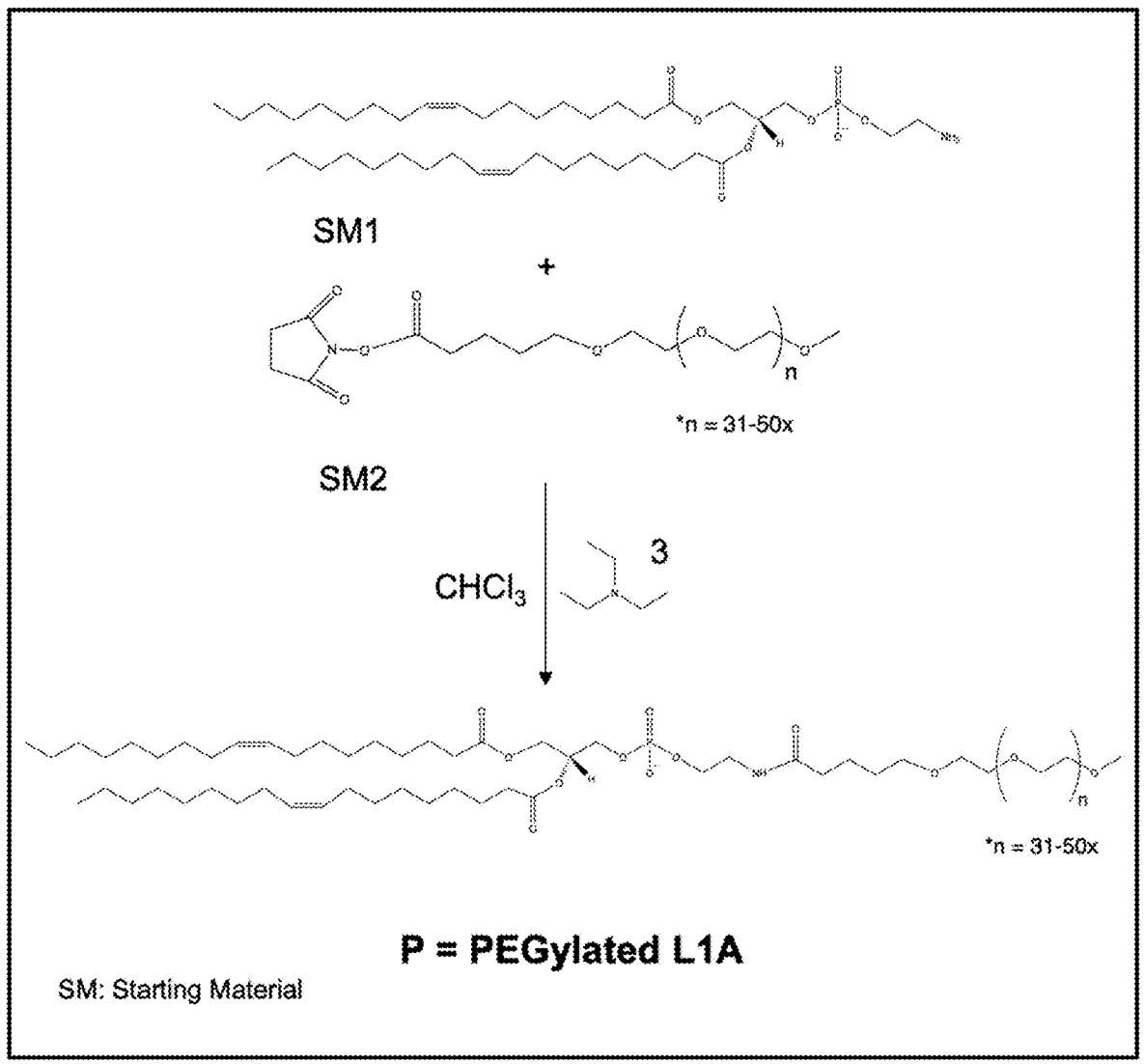
FIG. 3 shows confirmation of PEGylated L1A's synthesis, identity, purity, and integrity.
Figure 3:
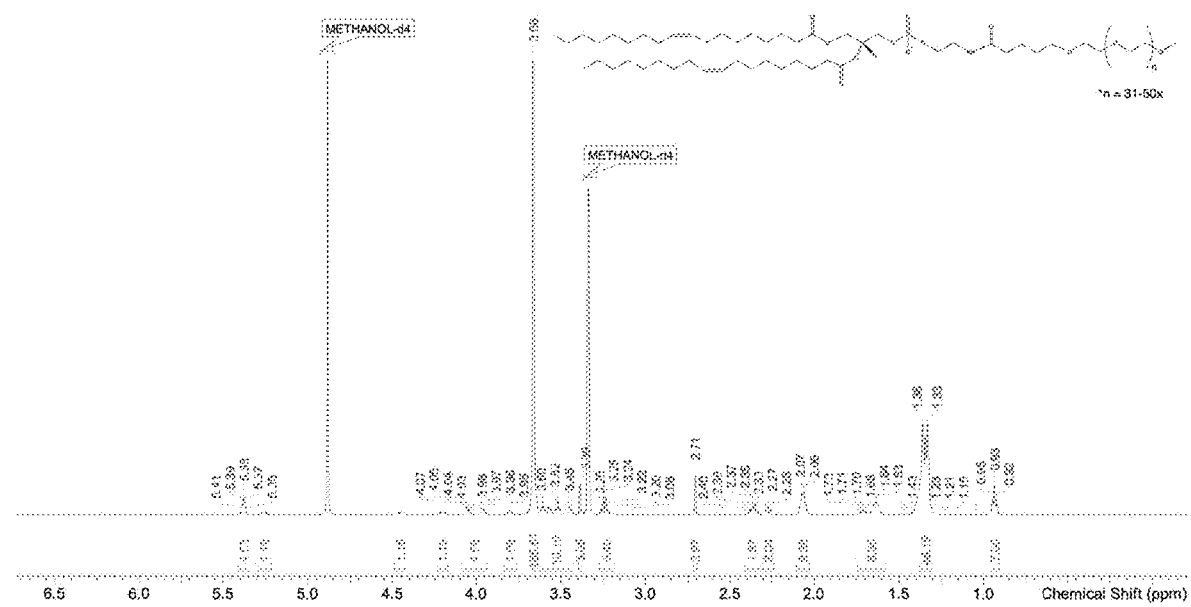
Figure 3:
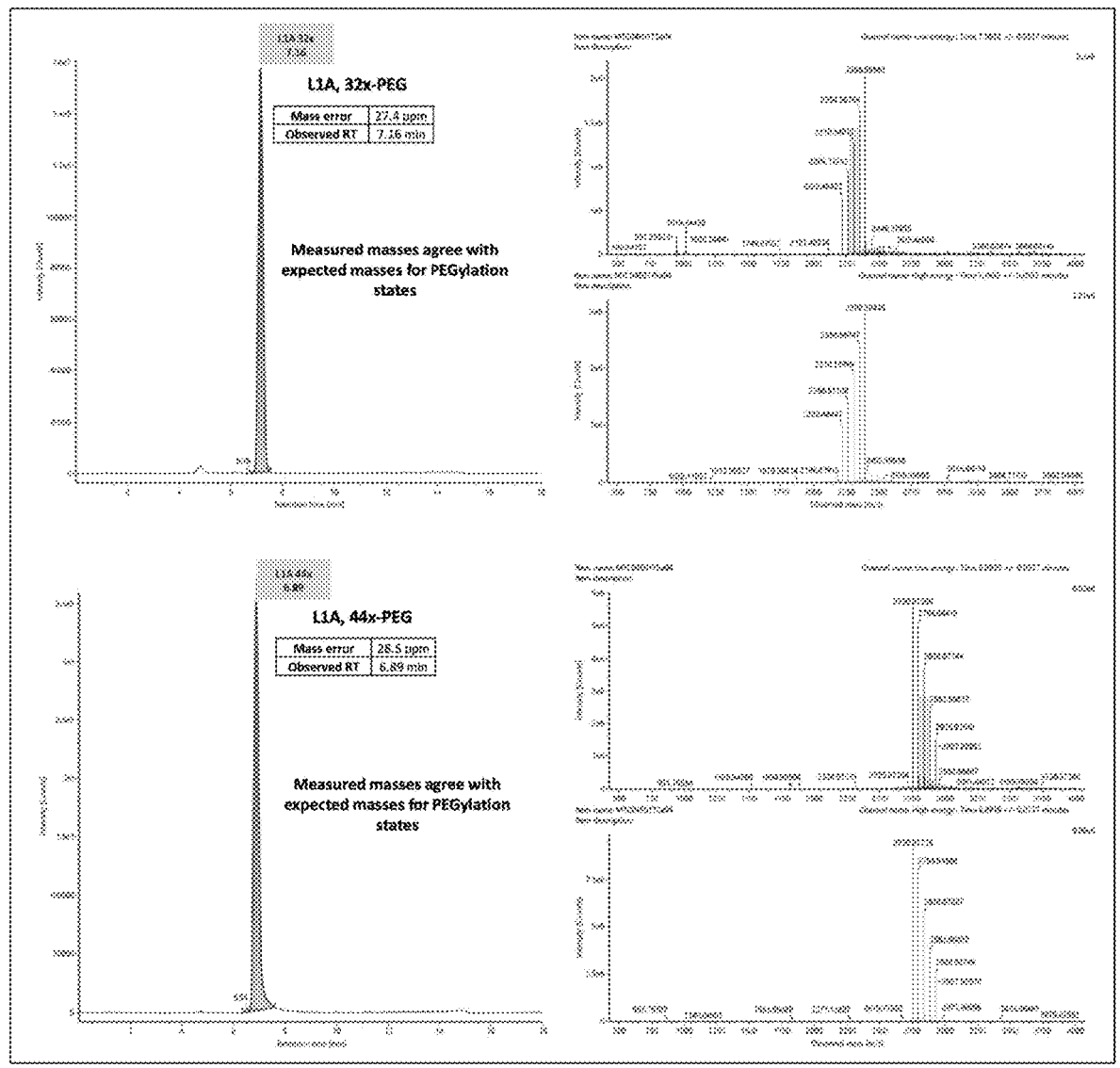
Figure 3:
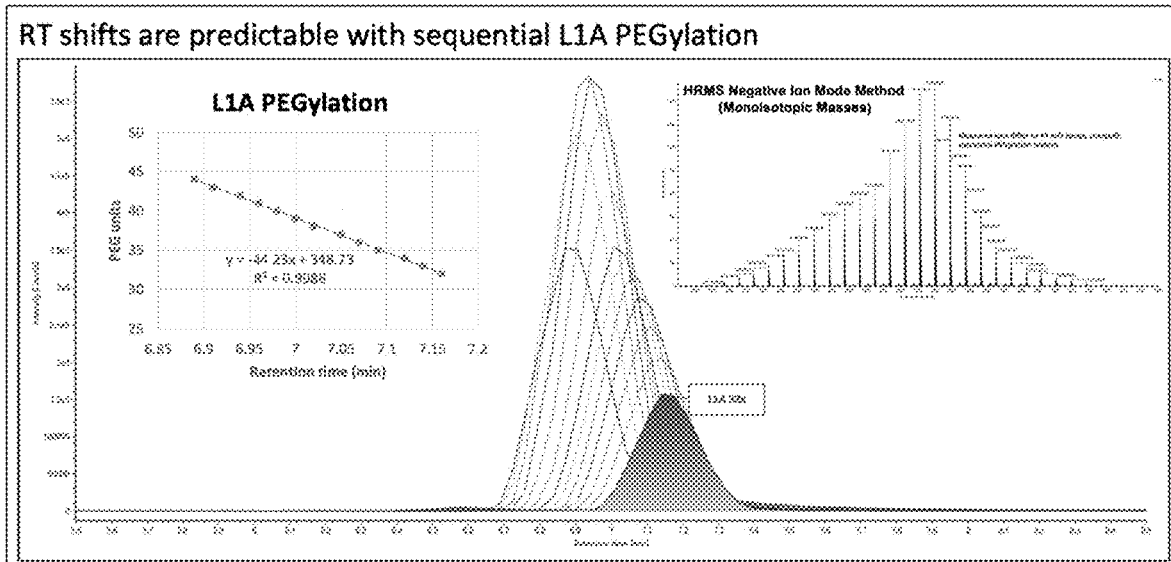

Provided herein is a lipid nanoparticle comprising a PEG-conjugated phospholipid (PEG-phospholipid) having two or more $C_{12}$-$C_{30}$ aliphatic chains, at least one of which includes from 1-5 sites of unsaturation, an ionizable lipid having at least two $C_{11}$-$C_{30}$ aliphatic chains and a head group that protonates to a cationic moiety having a pKa of 5-7, a non-cationic phospholipid having at least two $C_{11}$-$C_{30}$ aliphatic chains and a head group that remains a zwitterion or anion across a pH range of 6 to 8; and a sterol, fat-soluble steroid, or vitamin. These lipid nanoparticles are useful for the delivery of a variety of therapeutic agents, including but not limited to nucleic acid agents and small molecule drugs.

Definitions

Unless defined otherwise, all technical and scientific terms used herein have the same meaning as commonly understood to one of ordinary skill in the art to which this disclosure pertains. Otherwise, certain terms used herein have the meanings as set forth in the specification.

"A," "an," or "a (n)", is an indefinite article when used in reference to a group of substituents or "substituent group" herein, mean at least one.

"About" when referring to a value includes the stated value+/−10% of the stated value. For example, about 50% includes a range of from 45% to 55%, while about 20 molar equivalents includes a range of from 18 to 22 molar equivalents. Accordingly, when referring to a range, "about" refers to each of the stated values+/−10% of the stated value of each end of the range. For instance, a ratio of from about 1 to about 3 (weight/weight) includes a range of from 0.9 to 3.3.

"Composition" as used herein is intended to encompass a product that includes the specified lipid nanoparticle, optionally an active agent, and pharmaceutically acceptable excipients, carriers or diluents as described herein, which results from combination of specific components.

As used herein, "polydispersity" refers a measure of broadness of molecular weight distribution. The larger the polydispersity index (PDI), the broader the molecular weight. PDI of a polymer is calculated as the ratio of weight average by number average molecular weight.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In certain embodiments, a pharmaceutically acceptable formulation of a lipid nanoparticle of the present invention will be substantially pyrogen-free. For example, in certain preferred embodiments, the endotoxin concentration of the subject preparation, as assayed by the via the gel-clot method (as a limits test with comparison to the maximum allowed FDA limit, as stated in appendix E of the Endotoxin Guidance), is less than 10 EU/mL or EU/single dosage formulation, and even more preferably less than 5, 1, or even 0.1 EU/mL or EU/single dosage formulation.

The phrase "pharmaceutically acceptable excipient," as used herein, refers to any ingredient other than the compounds described herein (for example, a vehicle capable of suspending, complexing, or dissolving the active compound) and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C, xylitol, and other species disclosed herein.

As used herein, the term "polypeptide" or "polypeptide of interest" refers to a polymer of amino acid residues typically joined by peptide bonds that can be produced naturally (e.g., isolated or purified) or synthetically.

The term "alkyl" or "aliphatic" employed alone or in combination with other terms, refers to a hydrocarbon group that may be straight-chained or branched. The term "$C_{n-m}$ alkyl" or "$C_{n-m}$ aliphatic" refers to an alkyl group having n to m carbon atoms. An alkyl group formally corresponds to an alkane with one C—H bond replaced by the point of attachment of the alkyl group to the remainder of the compound. The alkyl and aliphatic groups herein may be unsaturated or saturated when specified. An alkyl or aliphatic group that is unsaturated has at least one double bond (sp$^2$ carbon atoms).

As used herein, the term "phospholipid" refers to a class of lipids whose molecule has a hydrophilic "head" containing a phosphate group (—OPO$_3$) and two hydrophobic "tails" derived from fatty acids, joined by an alcohol residue (usually a glycerol molecule). As used herein, the term "steroid" refers to a biologically active organic compound with four fused rings arranged in a specific molecular configuration. The steroid nucleus (core structure) is called gonane (cyclopentanoperhydrophenanthrene). It is typically composed of seventeen carbon atoms, bonded in four fused rings: three six-member cyclohexane rings (rings A, B and C) and one five-member cyclopentane ring (the D ring).

As used herein, the term "sterol" refers to a subgroup of steroids with a hydroxyl group at the 3-position of the A-ring.

As used herein, the term "vitamin" refers to a class of organic molecules (or a set of closely related molecules called vitamers) that are essential to an organism in small quantities for proper metabolic function.

As used herein, the terms "nucleic acid" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the nucleic acid. More particularly, the term "nucleic acid" includes polydeoxyribonucleotides (containing 2-deoxy-D-ribose), polyribonucleotides (containing D-ribose), including mRNA, shRNA and siRNA, whether spliced or unspliced, any other type of nucleic acid which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA.

As used herein, the term "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, untranslated regions (UTRs), a chain terminating nucleoside, a stem loop, a polyA sequence, and/or a polyadenylation signal. An RNA may have a nucleotide sequence encoding a polypeptide of interest. For example, an RNA may be a messenger RNA (mRNA). Translation of an mRNA encoding a particular polypeptide, for example, in vivo translation of an mRNA inside a mammalian cell, may produce the encoded polypeptide. RNAs may be selected from the non-liming group consisting of small interfering RNA (siRNA), asymmetrical interfering RNA (aiRNA), microRNA (miRNA), Dicer-substrate RNA (dsRNA), small hairpin RNA (shRNA), mRNA, circular RNA (circRNA), self-amplifying RNA (saRNA), long non-coding RNA (lncRNA), antisense RNA (asRNA), and mixtures thereof. In some aspects, the mRNA is a synthetic mRNA and comprises at least one unnatural nucleobase. In some aspects, all nucleobases of a certain class have been replaced with unnatural nucleobases (e.g., all uridines in a nucleic acid disclosed herein can be replaced with an unnatural nucleobase, e.g., 5-methoxyuridine). In some aspects, the nucleic acid (e.g., a synthetic RNA or a synthetic DNA) comprises only natural nucleobases, i.e., A, C, T and U in the case of a synthetic DNA, or A, C, T, and U in the case of a synthetic RNA.

As used herein, the term "DNA" refers to a deoxyribonucleic acid that may be naturally or non-naturally occurring. For example, DNA may include modified and/or non-naturally occurring components such as one or more nucleobases, nucleosides, or nucleotides. DNA includes cDNA, catalytic DNA, genomic DNA, and synthetic DNA. DNA can be double-stranded or single-stranded and, if single stranded, can be the coding strand or non-coding (anti-sense) strand. DNA can be used as an active drug agent in the lipid nanoparticles of the present disclosure.

As used herein, the term "gene therapy" refers to the introduction of genetic material into a recipient organism for healing purposes. Gene therapy can be used to obtain the desired therapeutic effect through different strategies, depending on the target disease. Gene therapy can be used to provide an absent gene in the receptor, or to complement or replace the defect in the function of a defective gene by inserting a normal copy of it into the cells. It is also possible to use gene therapy to obtain the opposite effect, that is, to inhibit or block the functioning of genes whose intervention contributes to the development of the disease. Alternatively, gene therapy can be used not to replace or inactivate the function of a gene, but to enter information that allows the cell to synthesize a protein with the desired therapeutic effect.

As used herein, the term "CRISPR" refers to a DNA modification technology. CRISPR utilizes short RNA sequences known as guide RNAs or gRNAs to direct a gene modification system to a specific sequence of DNA. Once bound to the target DNA, the enzyme(s) in the system modify the target DNA sequence. Multiple enzymes have been engineered to work with CRISPR technology such that DNA chains can be cut, nicked, extended, replaced, and/or otherwise edited to produce a sequence of interest. For example, CRISPR technology can be used for gene knock-out, gene knock-in, CRISPR interference (CRISPRi), CRISPR activation (CRISPRa), base editing, prime editing, CRISPR screens, or gene visualization. Alternatively, CRISPR technology can be used to modify epigenomics—the genome-wide set of chemical groups that adorn DNA and its associated histone packaging proteins, e.g., acetylating histone proteins at precise locations.

As used herein, the term "cell therapy" refers to therapy in which viable cells are injected, grafted or implanted into a patient in order to effectuate a medicinal effect. Cell therapy can be tissue transplantation therapy. Cell therapy can be allogeneic (the recipient will receive cells orginated from another person), autologous (the recipient will receive cells orginated from the patient's own tissues), or xenogeneic (the recipient will receive cells from another species). The types of cells used for cell therapy can be pluripotent stem cells (e.g., embryonic stem cells, neural stem cells, mesenchymal stem cells, and hematopoietic stem cells). Cell therapy can also use differentiated or mature cells (e.g., cardiomyocytes, islet cells, and chondrocytes). The cells cells used for cell therapy can be unmodified or modified/reprogrammed (e.g., CAR-engineered, such as CAR-T cells, CAR-NK cells, CAR-dendritic cells, CAR-macrophages, CAR-monocytes, and CAR-mesenchymal stem cells).

As used herein, the term "CAR" refers to a cell engineering technology. By engineering chimeric antigen receptor (CAR) proteins to give immune cells such as T cells, NK cells, dendritic cells, macrophages, monocytes, and mesenchymal stem cells the new ability to target a specific antigen. The receptors are chimeric in that they combine both antigen-binding and cell activating functions into a single receptor.

"Patient" or "subject" refers to a living organism, which includes, but is not limited to a human subject suffering from or prone to a disease or condition that can be treated by administration of a pharmaceutical composition as provided herein. Further non-limiting examples may include, but are not limited to, humans or other mammals. In some embodiments, the subject or patient is a human.

As used herein, the term "treating" or "treatment" refers to inhibiting a disease; for example, inhibiting a disease, condition, or disorder in an individual who is experiencing or displaying the pathology or symptomology of the disease, condition, or disorder (i.e., arresting further development of the pathology and/or symptomology) or ameliorating the disease; for example, ameliorating a disease, condition, or disorder in an individual who is experiencing or displaying the pathology or symptomology of the disease, condition, or disorder (i.e., reversing the pathology and/or symptomology) such as decreasing the severity of the disease.

The term "prevent," "preventing," or "prevention" as used herein, comprises the prevention of at least one symptom associated with or caused by the state, disease or disorder being prevented. The term "pharmaceutical product" refers to a product that contains an active pharmaceutical ingredient that has been shown to be a safe and effective treatment of one or more indications as supported by findings from clinical trials regulated by a governmental authority, e.g., the Food and Drug Administration or the similar authority in other countries.

Lipid Nanoparticles

In an aspect, provided herein is a lipid nanoparticle comprising:
(i) a PEG-conjugated phospholipid (PEG-phospholipid) having two or more $C_{12}$-$C_{30}$ aliphatic chains, at least one of which includes from 1-5 sites of unsaturation;
(ii) an ionizable lipid having at least two $C_{11}$-$C_{30}$ aliphatic chains and a head group that protonates to a cationic moiety having a pKa of 5-7;
(iii) a non-cationic phospholipid having at least two $C_{11}$-$C_{30}$ aliphatic chains and a head group that remains a zwitterion or anion across a pH range of 6 to 8; and
(iv) a sterol, fat-soluble steroid, or vitamin.

In an embodiment, the PEG-phospholipid has a molecular weight in the range of 0.2-6 kDa.

In another aspect, provided herein is a lipid nanoparticle comprising:
(i) a PEG-conjugated phospholipid (PEG-phospholipid) having two or more alkyl chains, at least one of which includes from 1-5 sites of unsaturation, and a head group substituted with a polyethylene glycol (PEG) polymer moiety, wherein the polyethylene glycol (PEG) polymer moiety has 2-50 polyethylene glycol subunits;
(ii) a cationic lipid having a cationic head group and two or more $C_{11}$-$C_{30}$ aliphatic chains, at least one of which includes from 1-5 sites of unsaturation, wherein the aliphatic chains are attached to the headgroup through a biodegradable linker;
(iii) a non-cationic phospholipid that remains a zwitterion or anion across a pH range of 6 to 8, having two or more $C_{11}$-$C_{30}$ aliphatic chains; and
(iv) a sterol, fat-soluble steroid, or vitamin.

In an embodiment, the PEG-phospholipid has an average molecular weight in the range of 200 to 7500 amu.

In another aspect, provided herein is a lipid nanoparticle comprising:
(i) a PEG-conjugated phospholipid (PEG-phospholipid) having two or more alkyl chains, at least one of which includes from 1-5 sites of unsaturation, and a head group substituted with a polyethylene glycol (PEG) polymer moiety, wherein the polyethylene glycol (PEG) polymer moiety has 2-50 polyethylene glycol subunits;
(ii) a cationic lipid having a cationic head group and two or more $C_{12}$-$C_{30}$ aliphatic chains, at least one of which includes from 1-5 sites of unsaturation, wherein the aliphatic chains are attached to the headgroup through a biodegradable linker;
(iii) a non-cationic phospholipid that remains a zwitterion or anion across a pH range of 6 to 8, having two or more $C_{12}$-$C_{30}$ aliphatic chains; and
(iv) a sterol, fat-soluble steroid, or vitamin.

In an embodiment, the PEG-phospholipid has an average molecular weight in the range of 200 to 7500 amu.

In an embodiment, (i) is

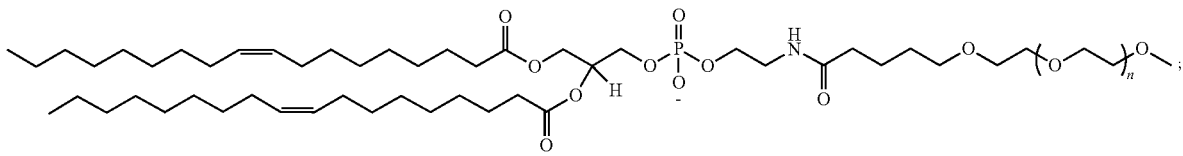

wherein n is an integer from 32 to 50.

In an embodiment n is 35-45. In another embodiment, n is 40, 41, 42, 43, 44, 45, 46, 47, or 48.

In an embodiment, (i) is

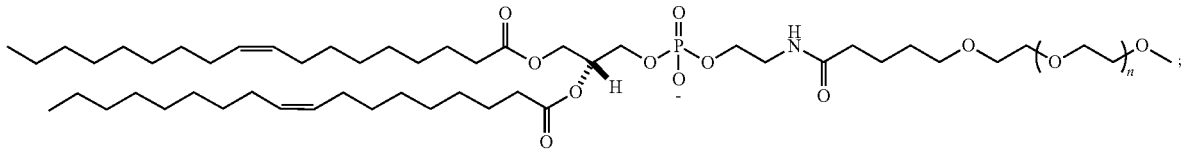

wherein n is an integer from 32 to 50.

In an embodiment, n is 43. In an embodiment, n is 44.
In an embodiment, the lipid nanoparticles comprise:
(i) a PEG-conjugated phospholipid having the structure

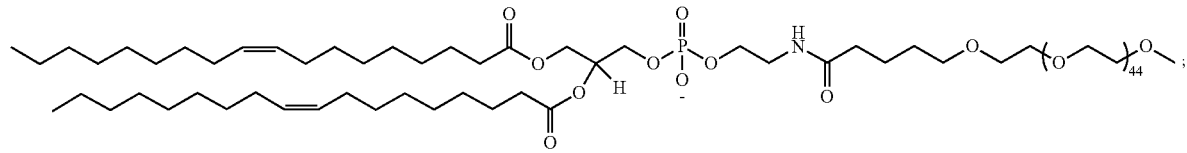

(ii) an ionizable lipid having the structure

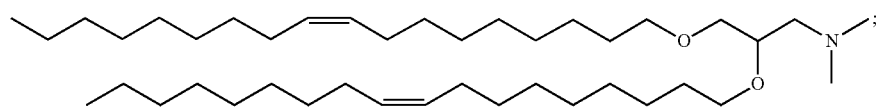

(iii) a non-cationic phospholipid having the structure

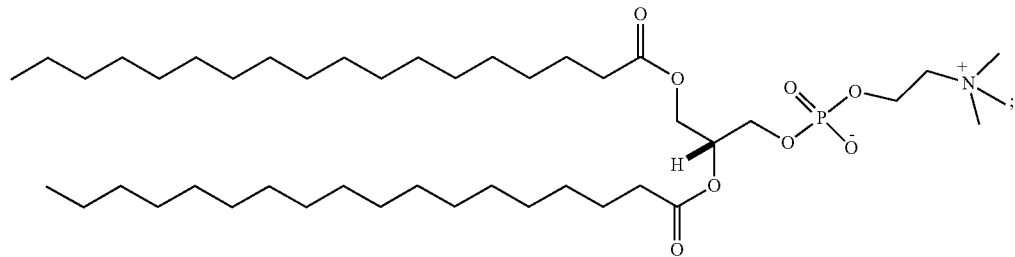

and
(iv) cholesterol.
In another embodiment, the lipid nanoparticles comprise:
(i) a PEG-conjugated phospholipid having the structure

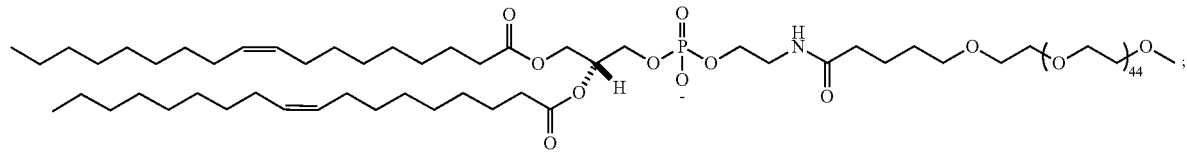

(ii) an ionizable lipid having the structure

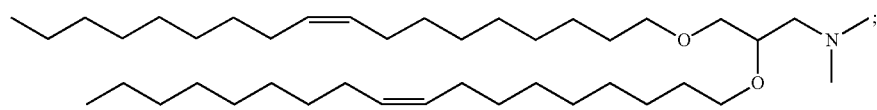

(iii) a non-cationic phospholipid having the structure (iv)

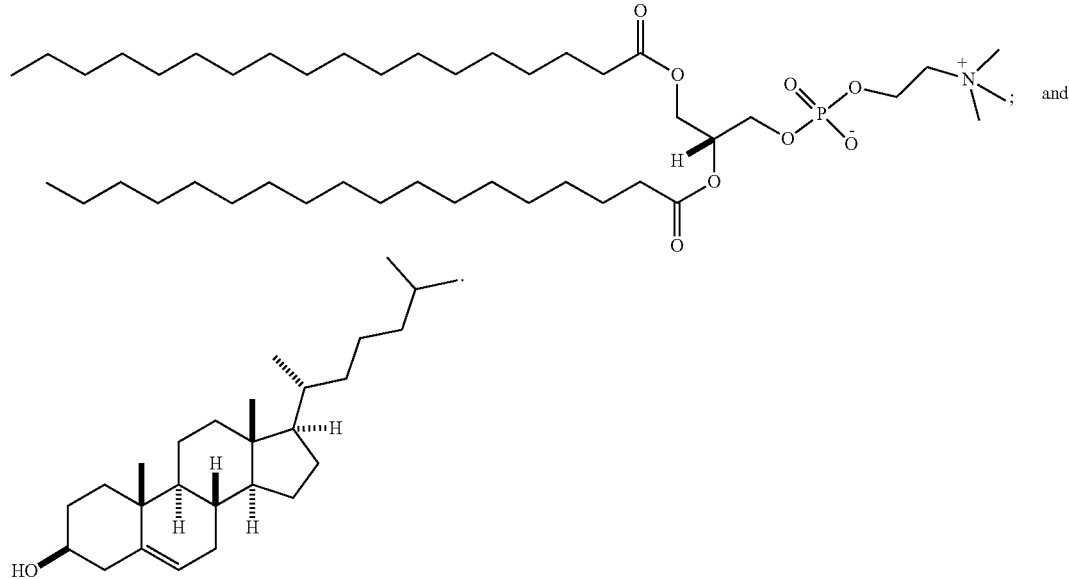

This lipid nanoparticle is also referred to herein as "LNP-1."

In an embodiment, the PEG-conjugated phospholipid is present in the lipid nanoparticle in an average amount of 0.25 to 10 mol % of the four components. In another embodiment, the ionizable lipid is present in the lipid nanoparticle in a relative amount of 5 to 60 mol %, the non-cationic phospholipid is present in the lipid nanoparticle in a relative amount of 5 to 55 mol %, and the cholesterol is present in the lipid nanoparticle in a relative amount of 30 to 60 mol %, with the proviso that the mol % of the four components totals 100 mol %.

In another embodiment, the lipid nanoparticles have a relative ratio of 50:10:39.25:0.75 for the ionizable lipid, the non-cationic phospholipid, cholesterol and the PEG-conjugated phospholipid.

In another embodiment, the lipid nanoparticle is stable at 2-8° C. for at least 10, 20, 30, 40, 50, 60, 70, 80, 90, 100, 110, 120, 130, 140, 150, 160, 170, or 180 days. In another embodiment, the lipid nanoparticle is stable at 2-8° C. for at least 180 days. In another embodiment, the lipid nanoparticle is stable at 2-8° C. for at least 270 days. In another embodiment, the lipid nanoparticle is stable at 2-8° C. for at least 360 days. In another embodiment, the lipid nanoparticle is stable at 2-8° C. for at least 540 days. In another embodiment, the lipid nanoparticle is stable at 2-8° C. for at least 720 days. In another embodiment, the lipid nanoparticle is stable at 2-8° C. for at least 900 days. In another embodiment, the lipid nanoparticle is stable at 2-8° C. for at least 1080 days. In another embodiment, the lipid nanoparticle is stable at 2-8° C. for at least 1260 days. In another embodiment, the lipid nanoparticle is stable at 2-8° C. for at least 1440 days.

In an embodiment, after storage for at least 180 days at 2-8° C. the lipid nanoparticles maintain a polydispersity within 10% of polydispersity measured at initial preparation of the formulation. In another embodiment, after storage for at least 180 days at 2-8° C. the lipid nanoparticles maintain a polydispersity within 10% of polydispersity measured at initial preparation of the formulation.

In yet another embodiment, the lipid nanoparticle is stable at about 25° C. for at least 10, 20, 30, 40, 50, 60, 70, 80, 90, 100, 110, or 120 days. In another embodiment, the lipid nanoparticle is stable at about 25° C. for at least 120 days. the lipid nanoparticle is stable at about 25° C. for at least 150 days. In another embodiment, the lipid nanoparticle is stable at about 25° C. for at least 180 days. In another embodiment, the lipid nanoparticle is stable at about 25° C. for at least 270 days. In another embodiment, the lipid nanoparticle is stable at about 25° C. for at least 360 days. In another embodiment, the lipid nanoparticle is stable at 25° C. for at least 540 days. In another embodiment, the lipid nanoparticle is stable at 25° C. for at least 720 days. In another embodiment, the lipid nanoparticle is stable at 25° C. for at least 900 days. In another embodiment, the lipid nanoparticle is stable at 25° C. for at least 1080 days.

In still another embodiment, the lipid nanoparticle is stable at about 40° C. for at least 1, 2, 3, 4, 5, 6, or 7 days. In another embodiment, the lipid nanoparticle is stable at about 40° C. for at least 7 days. In another embodiment, the lipid nanoparticle is stable at about 40° C. for at least 8 days. In another embodiment, the lipid nanoparticle is stable at about 40° C. for at least 10 days. In another embodiment, the lipid nanoparticle is stable at about 40° C. for at least 12 days. In another embodiment, the lipid nanoparticle is stable at about 40° C. for at least 14 days. In another embodiment, the lipid nanoparticle is stable at about 40° C. for at least 16 days. In another embodiment, the lipid nanoparticle is stable at about 40° C. for at least 18 days.

In another embodiment, provided herein is a lipid nanoparticle formulation in which the lipid nanoparticle maintains a polydispersity within 10% of its polydispersity at formulation after at least 180 days at 2-8° C. In an embodiment, the lipid nanoparticle maintains a polydispersity within 10% of its polydispersity at formulation after at least 270 days at 2-8° C. In another embodiment, the lipid nanoparticle maintains a polydispersity within 10% of its polydispersity at formulation after at least 360 days at 2-8° C. In another embodiment, the lipid nanoparticle maintains a polydispersity within 10% of its polydispersity at formulation after at least 540 days at 2-8° C. In another embodiment, the lipid nanoparticle maintains a polydispersity within 10% of its polydispersity at formulation after at least 720 days at 2-8° C. In another embodiment, the lipid nanoparticle maintains a polydispersity within 10% of its polydispersity at formulation after at least 900 days at 2-8° C. In another embodiment, the lipid nanoparticle maintains a polydispersity within 10% of its polydispersity at formulation after at least 1080 days at 2-8° C. In another embodiment, the lipid nanoparticle maintains a polydispersity within 10% of its polydispersity at formulation after at least 1260 days at 2-8° C. In another embodiment, the lipid nanoparticle maintains a polydispersity within 10% of its polydispersity at formulation after at least 1440 days at 2-8° C.

In an embodiment, provided herein is a lipid nanoparticle formulation in which the lipid nanoparticle maintains a polydispersity within 10% of its polydispersity at formulation after at least 60 days at 25° C. In another embodiment, provided herein is a lipid nanoparticle formulation in which the lipid nanoparticle maintains a polydispersity within 10% of its polydispersity at formulation after at least 120 days at 25° C. In an embodiment, the lipid nanoparticle maintains a polydispersity within 10% of its polydispersity at formulation after at least 180 days at 25° C. In another embodiment, the lipid nanoparticle maintains a polydispersity within 10% of its polydispersity at formulation after at least 270 days at 25° C. In another embodiment, the lipid nanoparticle maintains a polydispersity within 10% of its polydispersity at formulation after at least 360 days at 25° C. In another embodiment, the lipid nanoparticle maintains a polydispersity within 10% of its polydispersity at formulation after at least 540 days at 25° C. In another embodiment, the lipid nanoparticle maintains a polydispersity within 10% of its polydispersity at formulation after at least 720 days at 25° C. In another embodiment, the lipid nanoparticle maintains a polydispersity within 10% of its polydispersity at formulation after at least 900 days at 25° C. In another embodiment, the lipid nanoparticle maintains a polydispersity within 10% of its polydispersity at formulation after at least 1080 days at 25° C.

In an embodiment, the PEG-phospholipid has a head group selected from the group consisting of phosphatidylcholine, phosphatidylserine, phosphatidylethanolamine, phosphatidylinositol, phosphatidic acid, phosphatidylglycerols, ethoxy, and methoxy.

In another embodiment, the PEG-phospholipid has a head group selected from the group consisting of phosphatidylethanolamine and phosphatidylcholine. In an embodiment, the PEG-phospholipid is present at 0.25-10 mol %. In an embodiment, the PEG-phospholipid is present at 0.25-5 mol %. In another embodiment, the PEG-phospholipid is present at 0.5-5 mol %. In yet another embodiment, the PEG-phospholipid is present at 0.75-2.5 mol %. In still another embodiment, the PEG-phospholipid is present at 0.75-1.0 mol %.

In certain preferred embodiments, the PEG-phospholipid has two aliphatic chains.

In yet another embodiment, the two or more $C_{12}$-$C_{30}$ aliphatic chains of the PEG-phospholipid are $C_{14}$-$C_{18}$ aliphatic chains.

In still another embodiment, each of the $C_{14}$-$C_{18}$ aliphatic chains is unsaturated.

In an embodiment, each of the $C_{14}$-$C_{18}$ aliphatic chains is unsaturated at 1-3 positions.

In another embodiment, PEG polymer moiety is a linear polymer and represented in the formula

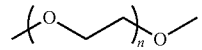

wherein n is an integer from 2-50. In an embodiment, n is an integer from 5-50. In yet another embodiment, n is an integer from 15-40. In still another embodiment, n is an integer from 20-50, or is an integer from 30-50, or is an integer from 40-50. In certain embodiments, n is 42, 43, 44, 45 or 46. In certain embodiments, n is 44. In an embodiment, n is an integer from 20 to 35. In an embodiment, n is an integer from 20 to 35.

In an embodiment, the PEG polymer moiety includes a ligand moiety that binds to a cognate binding partner expressed on the cell surface of cells in the target tissue and which, upon assembly of the lipid nanoparticle, is present on the surface of the nanoparticle.

The ionizable lipids of the present LNPs are lipids having headgroups which are capable of modulating their charge depending on the environmental pH.

In certain embodiments, the ionizable lipid is a cationic lipid having a headgroup which while neutral at serum pH becomes positively charged at the pH of an endosome.

In another embodiment, the cationic head group of the cationic lipid is an ionizable head group having a pKa less than 6.7. In another embodiment, the cationic lipid is present at 5-60 mol %. In another embodiment, the cationic lipid is present at 5-55 mol %. In certain embodiments, the cationic lipid is present at 30-60 mol %. In certain embodiments, the cationic lipid is present at 40-55 mol %. In certain embodiments, the cationic lipid is present at about 50 mol %. In certain embodiments, the cationic lipid is present at 50 mol %.

In yet another embodiment, the ionizable head group includes a tertiary amine which has a pKa less than 6.7.

In still another embodiment, the pKa of the ionizable head group has a pKa in the range of 6.2 to 6.5.

In an embodiment, the cationic head group and its neighboring aliphatic chain are in a 1,2-relationship.

In another embodiment, the unsaturated $C_{11}$-$C_{30}$ aliphatic chains are unsaturated $C_{14}$-$C_{18}$ aliphatic chains. In another embodiment, the unsaturated $C_{12}$-$C_{30}$ aliphatic chains are unsaturated $C_{14}$-$C_{18}$ aliphatic chains.

In yet another embodiment, the two or more aliphatic chains are, independently for each occurrence, selected from α-Linolenic acid, γ-Linolenic acid, Arachidonic acid, Cervonic acid, Dihomo-γ-linolenic acid, Docosatetraenoic acid, Eicosapentaenoic acid, Elaidic acid, Erucic acid, Gondoic acid, Linoleic acid, Linolelaidic acid, Mead acid, Nervonic acid, Oleic acid, Palmitoleic acid, Paullinic acid, Stearidonic acid, and Vaccenic acid.

In still another embodiment, the unsaturated $C_{11}$-$C_{30}$ aliphatic chains are unsaturated $C_{18}$ aliphatic chains. In still another embodiment, the unsaturated $C_{12}$-$C_{30}$ aliphatic chains are unsaturated $C_{18}$ aliphatic chains. In an embodiment, the unsaturated $C_{18}$ aliphatic chains are selected from oleic, linoleic and α-linoleic acids.

In another embodiment, the $C_{18}$ aliphatic chains are covalently linked to the head group through an ether, ester or amide bond, or other bond that can be hydrolyzed (e.g., by enzyme-mediated or by enzyme independent processes) in vivo to release the aliphatic chain.

In an embodiment, the cationic lipid can be one or a combination thereof selected from 1,2-dioleyloxy-3-dimethylaminopropane or (2R)—N,N-dimethyl-2,3-bis [(9Z)-9-octadecen-1-yloxy]-1-propanamine) (DODMA), (N,N-dimethyl-2,3-bis [(9Z, 12Z)-9,12-octadecadien-1-yloxy]-1-propanamine) (DLin-DMA), (4-dimethylamino)-butanoic acid, (10Z, 13Z)-1-(9Z,12Z)-9, 12-octadecadien-1-yl-10,13-nonadecadien-1-yl ester (DLin-MC3-DMA), N, N-dimethyl-2,2-di-(9Z, 12Z)-9, 12-octadecadien-1-yl-1, 3-dioxolane-4-ethanamine (DLin-KC2-DMA), (2-hexyl-decanoic acid, 1,1'-[[(4-hydroxybutyl)imino]di-6, 1-hexanediyl] ester (ALC-0315), 8-[(2-hydroxyethyl) [6-oxo-6-(undecyloxy) hexyl]amino]-octanoic acid, 1-octylnonyl ester (SM-102), 1-1'-((2-(4-(2-((2-(bis(2-hydroxydecyl)amino)ethyl) (2-hydroxydecyl)amino)ethyl) piperazin-1-yl)ethyl) azanediyl) bis(decan-2-ol) ($C_{10}$-200), 9,12-octadecadienoic acid, (9Z, 12Z)-1,1'[2-[[[3-(diethylamino) propoxy]carbonyl]oxy]-1,3-propanediyl] ester (Ionizable Lipid 4, IL4), 5-(dimethylamino)-pentanoic acid, (6Z)-1,2-di-(4Z)-4-decen-1-yl-6-dodecen-1-yl ester (Lipid CL1), 4-methyl-1-piperazinepropanoic acid, 2-[di-(9Z,12Z)-9,12-octadecadien-1-ylamino]ethyl ester (Lipid 10), 9-[4-(dimethylamino) 1-oxobutoxy]-heptadecanedioic acid, 1,17-di-3-decyn-1-yl ester (Lipid A6), Di((Z)-octadec-9-en-1-yl) L-lysyl-L-glutamate, dihydrochloride (Lipid OA2 (hydrochloride)), 1-methyl-4-piperidinecarboxylic acid, 11-[(2-hexyl-1-oxodecyl)oxy]-5-[6-[(2hexyl-1-oxodecyl)oxy]hexyl]-5-hydroxyundecyl ester (CL15F6), Piperazine-1,4-diylbis(ethane-2,1-diyl) (9Z,9'Z, 12Z, 12'Z)-bis(octadeca-9,12-dienoate) (AA3-DLin), 5-(((3dibutylamino) propyl)amino)methyl)-6-hydroxyundecane-1,11-diyl(9Z,9'Z, 12,12'Z)-bis(octadeca-9,12-dienoate) (IR-117-17), 1-methyl-4,4-bis [9Z, 12Z)-912-octadecadien-1-yloxy]-piperidine (YSK05), 9-[4-(dimethylamino)-1-oxobutoxy]-heptadecanoic acid, 1,17-di-(2Z)-2-nonen-1-yl ester (L-319), 3,6-bis [4-[bis [(9Z, 12Z)-2-hydroxy-9, 12-octacadien-1-yl] amino]butyl]-2,5-piperazinedione, (OF-02) 9,12-octadecadienoic acid, (9Z, 12Z)-1,1',1",1"'-[3,6-dioxo-2,5-piperazinediyl)bis(4,1-butanediylnitrilodi-4, 1-butanediyl)] ester (OF—$C_4$-Deg-Lin), 9Z, 12Z-octadecadienoic acid, 1,1',1",1"'-[(3,6-dioxo-2,5-piperazinediyl)bis(4, 1-butanediylnitrilodi-2, 1-ethanediyl)] ester (OF-Deg-Lin), 4,4'-[[[[3-(dimethylamino) propil]thio]carbonyl]imino]bisbutanoic acid, 1, 1'-bis(1-heptyloctyl) ester (ATX-100), 1-[3-(dimethylamino) propyl]-5,5-di-(8Z)-8-heptadecen-1-yl-2,5-dihydro-1H-imidazole-2-carboxylic acid, ethyl ester (A12-Iso5-2DC18).

In yet another embodiment, the non-cationic phospholipid has a head group selected from phosphatidylcholine, phosphatidylserine, phosphatidylethanolamine, phosphatidylinositol, phosphatidic acid and phosphatidylglycerols. In still another embodiment, the non-cationic phospholipid is a phosphatidylethanolamine or phosphatidylcholine.

In an embodiment, the two or more $C_{11}$-$C_{30}$ aliphatic chains of the non-cationic phospholipid are $C_{14}$-$C_{18}$ aliphatic chains that, independently for each chain, are saturated or unsaturated at 1-3 positions.

In another embodiment, the two or more $C_{11}$-$C_{30}$ aliphatic chains of the non-cationic lipid are saturated $C_{14}$-$C_{18}$ aliphatic chains.

In yet another embodiment, the non-cationic phospholipid can be one or a combination thereof selected from 1,2-diundecanoyl-sn-glycero-3-phosphatidylcholine (11:0 PC, DUPC), 1,2-dilauroyl-sn-glycero-3-phosphatidylcholine (12:0 PC), 1,2-ditridecanoyl-sn-glycero-3-phosphatidylcholine (13:0 PC), 1,2-dimyristoyl-sn-glycero-3-phosphatidylcholine (14:0 PC, DMPC), 1,2-dipentadecanoyl-sn-glycero-3-phosphatidylcholine (15:0 PC), 1,2-dipalmitoyl-sn-glycero-3-phosphatidylcholine (16:0 PC, DPPC), 1,2-diphytanoyl-sn-glycero-3-phosphatidylcholine (4ME 16:0 PC), 1,2-diheptadecanoyl-sn-glycero-3-phosphatidylcholine (17:0 PC), 1,2-distearoyl-sn-glycero-3-phosphatidylcholine (18:0 PC, DSPC), 1,2-Distearoyl-sn-glycero-3-Ethylphosphatidylcholine (Ethyl-DSPC)

1,2-dinonadecanoyl-sn-glycero-3-phosphatidylcholine (19:0 PC), 1,2-diarachidoyl-sn-glycero-3-phosphatidylcholine (20:0 PC), 1,2-dihenarachidoyl-sn-glycero-3-phosphatidylcholine (21:0 PC), 1,2-dibehenoyl-sn-glycero-3-phosphatidylcholine (22:0 PC), 1,2-ditricosanoyl-sn-glycero-3-phosphatidylcholine (23:0 PC), 1,2-dilignoceroyl-sn-glycero-3-phosphatidylcholine (24:0 PC), 1,2-dimyristoleoyl-sn-glycero-3-phosphatidylcholine (14:1 (49-Cis) PC), 1,2-dimyristelaidoyl-sn-glycero-3-phosphatidylcholine (14:1 (49-Trans) PC), 1,2-dipalmitoleoyl-sn-glycero-3-phosphatidylcholine (16:1 (49-Cis) PC), 1,2-dipalmitelaidoyl-sn-glycero-3-phosphatidylcholine (16:1 (49-Trans) PC), 1,2-dipetroselenoyl-sn-glycero-3-phosphatidylcholine (18:1 (46-Cis) PC), 1,2-dioleoyl-sn-glycero-3-phosphatidylcholine (18:1 (49-Cis) PC, DOPC), 1,2-dielaidoyl-sn-glycero-3-phosphatidylcholine (18:1 (49-Trans) PC), 1,2-dilinoleoyl-sn-glycero-3-phosphatidylcholine (18:2 (Cis) PC, DLPC), 1,2-dilinolenoyl-sn-glycero-3-phosphatidylcholine (18:3 (Cis) PC, DLnPC), 1,2-dieicosenoyl-sn-glycero-3-phosphatidylcholine (20:1 (Cis) PC), 1,2-diarachidonoyl-sn-glycero-3-phosphatidylcholine (20:4 (Cis) PC, DAPC), 1,2-dierucoyl-sn-glycero-3-phosphatidylcholine (22:1 (Cis) PC), 1,2-didocosahexaenoyl-sn-glycero-3-phosphatidylcholine (22:6 (Cis) PC, DHAPC), 1,2-dinervonoyl-sn-glycero-3-phosphatidylcholine (24:1 (Cis) PC), 1,2-dihexanoyl-sn-glycero-3-phosphatidylethanolamine (06:0 PE), 1,2-dioctanoyl-sn-glycero-3-phosphatidylethanolamine (08:0 PE),
1,2-didecanoyl-sn-glycero-3-phosphatidylethanolamine (10:0 PE),
1,2-dilauroyl-sn-glycero-3-phosphatidylethanolamine (12:0 PE),
1,2-dimyristoyl-sn-glycero-3-phosphatidylethanolamine (14:0 PE),
1,2-dipentadecanoyl-sn-glycero-3-phosphatidylethanolamine (15:0 PE),
1,2-dipalmitoyl-sn-glycero-3-phosphatidylethanolamine (16:0 PE),
1,2-diphytanoyl-sn-glycero-3-phosphatidylethanolamine (4ME 16:0 PE),
1,2-diheptadecanoyl-sn-glycero-3-phosphatidylethanolamine (17:0 PE),
1,2-distearoyl-sn-glycero-3-phosphatidylethanolamine (18:0 PE, DSPE),
1,2-dipalmitoleoyl-sn-glycero-3-phosphatidylethanolamine (16:1 PE),
1,2-dioleoyl-sn-glycero-3-phosphatidylethanolamine (18:1 (49-Cis) PE, DOPE),
1,2-dielaidoyl-sn-glycero-3-phosphatidylethanolamine (18:1 (49-Trans) PE),
1,2-dilinoleoyl-sn-glycero-3-phosphatidylethanolamine (18:2 PE, DLPE),
1,2-dilinolenoyl-sn-glycero-3-phosphatidylethanolamine (18:3 PE, DLnPE),
1,2-diarachidonoyl-sn-glycero-3-phosphatidylethanolamine (20:4 PE, DAPE),
1,2-didocosahexaenoyl-sn-glycero-3-phosphatidylethanolamine (22:6 PE, DHAPE),
1,2-di-O-octadecenyl-sn-glycero-3-phosphatidylcholine (18:0 Diether PC),
1,2-dioleoyl-sn-glycero-3-phospho-rac-(1-glycerol) sodium salt (DOPG),
1-myristoyl-2-palmitoyl-sn-glycero-3-phosphatidylcholine (14:0-16:0 PC, MPPC),
1-myristoyl-2-stearoyl-sn-glycero-3-phosphatidylcholine (14:0-18:0 PC, MSPC),
1-palmitoyl-2-acetyl-sn-glycero-3-phosphatidylcholine (16:0-02:0 PC),
1-palmitoyl-2-myristoyl-sn-glycero-3-phosphatidylcholine (16:0-14:0 PC, PMPC),
1-palmitoyl-2-stearoyl-sn-glycero-3-phosphatidylcholine (16:0-18:0 PC, PSPC),
1-palmitoyl-2-oleoyl-sn-glycero-3-phosphatidylcholine (16:0-18:1 PC, POPC),
1-palmitoyl-2-linoleoyl-sn-glycero-3-phosphatidylcholine (16:0-18:2 PC, PLPC),
1-palmitoyl-2-arachidonoyl-sn-glycero-3-phosphatidylcholine (16:0-20:4 PC),
1-palmitoyl-2-docosahexaenoyl-sn-glycero-3-phosphatidylcholine (14:0-22:6 PC),
1-stearoyl-2-myristoyl-sn-glycero-3-phosphatidylcholine (18:0-14:0 PC, SMPC),
1-stearoyl-2-palmitoyl-sn-glycero-3-phosphatidylcholine (18:0-16:0 PC, SPPC),
1-stearoyl-2-oleoyl-sn-glycero-3-phosphatidylcholine (18:0-18:1 PC, SOPC),
1-stearoyl-2-linoleoyl-sn-glycero-3-phosphatidylcholine (18:0-18:2 PC),
1-stearoyl-2-arachidonoyl-sn-glycero-3-phosphatidylcholine (18:0-20:4 PC),
1-stearoyl-2-docosahexaenoyl-sn-glycero-3-phosphatidylcholine (18:0-22:6 PC),
1-oleoyl-2-myristoyl-sn-glycero-3-phosphatidylcholine (18:1-14:0 PC, OMPC),
1-oleoyl-2-palmitoyl-sn-glycero-3-phosphatidylcholine (18:1-16:0 PC, OPPC),
1-oleoyl-2-stearoyl-sn-glycero-3-phosphatidylcholine (18:1-18:0 PC, OSPC),
1-palmitoyl-2-oleoyl-sn-glycero-3-phosphatidylethanolamine (16:0-18:1 PE, POPE),
1-palmitoyl-2-linoleoyl-sn-glycero-3-phosphatidylethanolamine (16:0-18:2 PE),
1-palmitoyl-2-arachidonoyl-sn-glycero-3-phosphatidylethanolamine (16:0-20:4 PE),
1-palmitoyl-2-docosahexaenoyl-sn-glycero-3-phosphatidylethanolamine (16:0-22:6 PE),
1-stearoyl-2-oleoyl-sn-glycero-3-phosphatidylethanolamine (18:0-18:1 PE),
1-stearoyl-2-linoleoyl-sn-glycero-3-phosphatidylethanolamine (18:0-18:2 PE),
1-stearoyl-2-arachidonoyl-sn-glycero-3-phosphatidylethanolamine (18:0-20:4 PE),
1-stearoyl-2-docosahexaenoyl-sn-glycero-3-phosphatidylethanolamine (18:0-22:6 PE),
1-oleoyl-2-cholesterylhemisuccinoyl-sn-glycero-3-phosphatidylcholine (OchemsPC),
1-stearoyl-2-oleoyl-phosphatidyethanolamine (SOPE),
dipentadecanoyl-phosphatidylcholine (DPDPC),
dilauroylphosphatidylglycerol (DLPG),
diarachidoylphosphatidylglycerol (DAPG),
dimyristoylphosphatidylglycerol (DMPG),
dipalmitoylphosphatidylglycerol (DPPG),
distearoylphosphatidylglycerol (DSPG),
dimyristoyl phosphatidic acid (DMPA),
dipalmitoyl phosphatidic acid (DPPA),
distearoyl phosphatidic acid (DSPA),
diarachidoyl phosphatidic acid (DAPA),
dimyristoylphosphatidylethanolamine (DMPE),
dipalmitoylphosphatidylethanolamine (DPPE),
dimyristoyl phosphatidylserine (DMPS),
diarachidoyl phosphatidylserine (DAPS),
dipalmitoyl phosphatidylserine (DPPS),
distearoylphosphatidylserine (DSPS),
dioleoylphosphatidylserine (DOPS),
dipalmitoyl sphingomyelin (DPSP),
distearoylsphingomyelin (DSSP),
dilauroyl-phosphatidylinositol (DLPI),
diarachidoylphosphatidylinositol (DAPI),
dimyristoylphosphatidylinositol (DMPI),
dipalmitoylphosphatidylinositol (DPPI),
distearoylphosphatidylinositol (DSPI), and
dioleoyl-phosphatidylinositol (DOPI).

In still another embodiment, the non-cationic lipid is selected from DSPC, DOPC, DPPC, DOPG, DPPG, DOPE, POPC, POPE, DPPE, DMPE, DSPE, SOPE, and DLPE, or a combination thereof.

In another embodiment, the non-cationic lipid is present at 5-55 mol %. In another embodiment, the non-cationic lipid is present at 5-15 mol %. In certain embodiments, the non-cationic lipid is present at 5-30 mol %. In certain embodiments, the non-cationic lipid is present at 5-20 mol %. In certain embodiments, the non-cationic lipid is present at about 10 mol %. In certain embodiments, the non-cationic lipid is present at 9-12 mol %.

In an embodiment, (iv) is a sterol. In another embodiment, the sterol is cholesterol or an analog thereof. In yet another embodiment, the sterol is selected from 3-hydroxycholest- 5-ene (Cholesterol), 9,10-secocholesta-5,7,10 (19)-trien-3b-ol (Vitamin D3), ergocalciferol (Vitamin D2), calcipotriol, 24-ethyl-5,22-cholestadien-3b-ol (Stigmasterol), 22,23-Dihydrostigmasterol (β-Sitosterol), 3,28-Dihydroxy-lupeol (Betulin), Lupeol, Ursolic acid, Oleanolic acid, 24a-Methylcholesterol (Campesterol), 24-Ethylcholesta-5,24 (28) E-dien-3b-ol (Fucosterol), 24-Methylcholesta-5,22-dien-3b-ol (Brassicasterol), (22E)-Ergosta-5,7,22-trien-3β-ol (Ergosterol), 9,11-Dehydroergosterol, and Daucosterol, or any of the foregoing sterols modified with one or more amino acids.

In still another embodiment, the sterol is a plant-derived sterol. In an embodiment, the plant-derived sterol is selected from β-sitosterol, β-sitostanol, stigmasterol, stigmastanol, campesterol, campestanol, ergosterol, avenasterol, and brassicasterol, or any combination thereof.

In another embodiment, (iv) is a fat-soluble vitamin. In yet another embodiment, the fat-soluble vitamin is selected from a vitamin A, a secosteroid, a tocopherol, a tocotrienol, and a menaquinone, or an analog or combination thereof. In still another embodiment, the fat-soluble vitamin is selected from retinol, retinal, retinyl esters, vitamin D2 (ergocalciferol), vitamin D3 (cholecalciferol), vitamin E, vitamin K1, and vitamin K2, or an analog or combination thereof.

In another embodiment, the sterol or fat-soluble vitamin is present at 30-60 mol %. In certain embodiments, the sterol or fat-soluble vitamin is present at 35-50 mol %. In certain embodiments, the sterol or fat-soluble vitamin is present at 35-45 mol %. In certain embodiments, the sterol or fat-soluble vitamin is present at 38-41 mol %. In certain embodiments, the sterol or fat-soluble vitamin is present at about 39 mol %.

In an embodiment, the sterol, fat-soluble steroid, or vitamin is PEGylated.

In another embodiment, (i) is

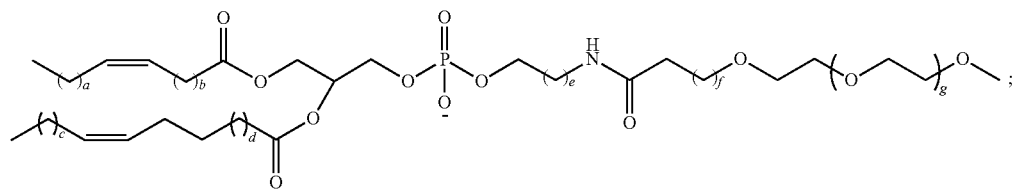

wherein
a is an integer between 1 and 10;
b is an integer between 1 and 10;
c is an integer between 1 and 10;
d is an integer between 1 and 10;
e is an integer between 1 and 5;
f is an integer between 1 and 5; and
g is an integer between 10 and 50.
In yet another embodiment,
a is an integer between 5 and 10;
b is an integer between 5 and 10;
c is an integer between 5 and 10;
d is an integer between 1 and 5;
e is an integer between 1 and 3;
f is an integer between 1 and 5; and
g is an integer between 30 and 50.

In still another embodiment, (ii) is

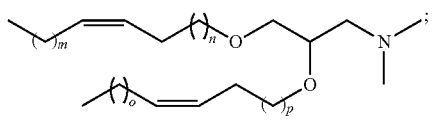

wherein
m is an integer between 1 and 10;
n is an integer between 1 and 10;
is an integer between 1 and 10; and
p is an integer between 1 and 10.
In an embodiment,
m is an integer between 5 and 10;
n is an integer between 5 and 10;
is an integer between 5 and 10; and
p is an integer between 5 and 10

In another embodiment, (iii) is

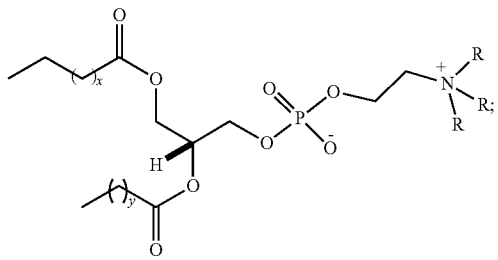

wherein
x is an integer between 10 and 20;
y is an integer between 10 and 20; and
each R is independently $C_{1-6}$ alkyl.
In yet another embodiment,
x is an integer between 15 and 20;
y is an integer between 15 and 20; and
each R is independently $C_{1-3}$ alkyl.

In still another embodiment, the lipid nanoparticle comprises

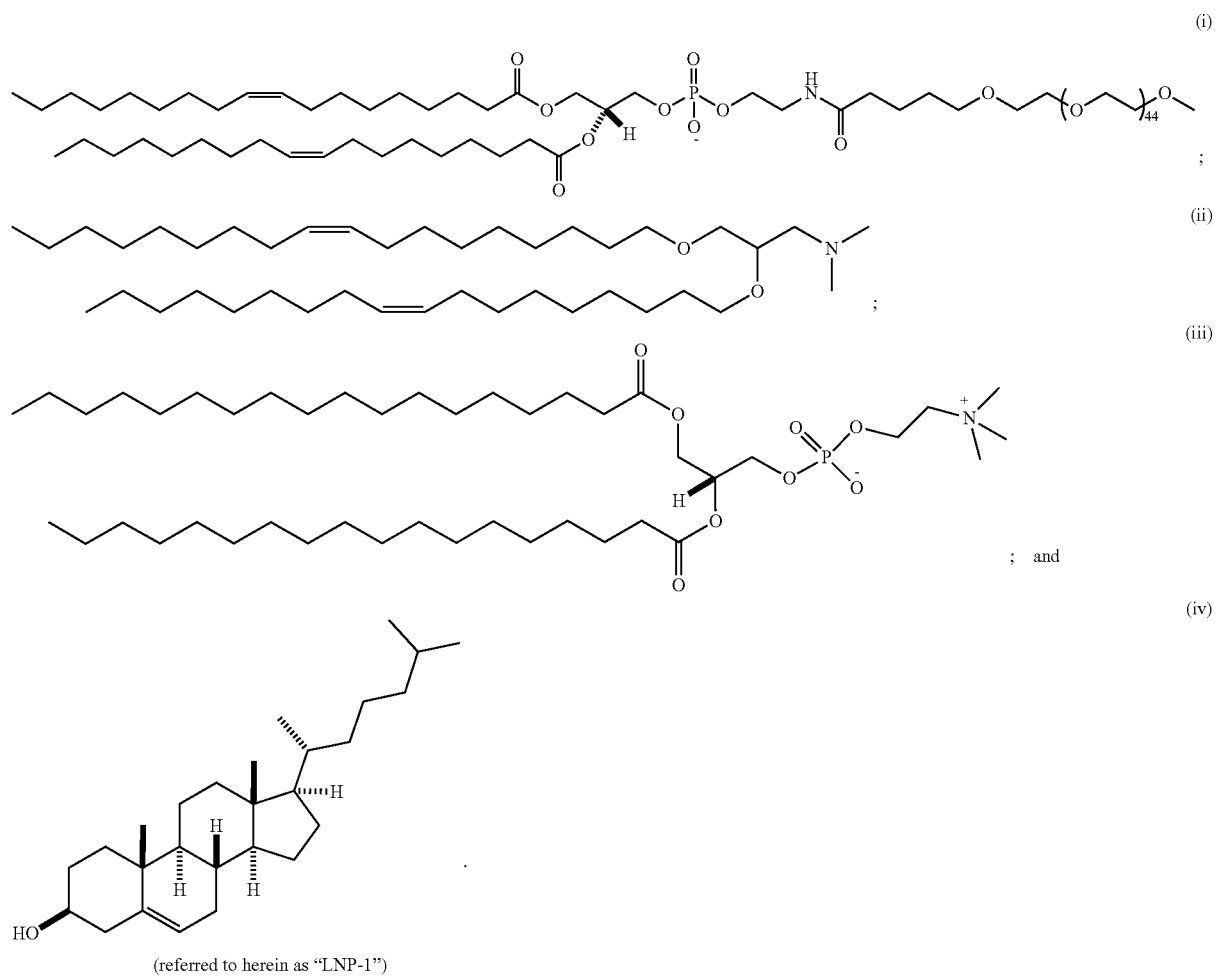
(referred to herein as "LNP-1")
In an embodiment, (i) is
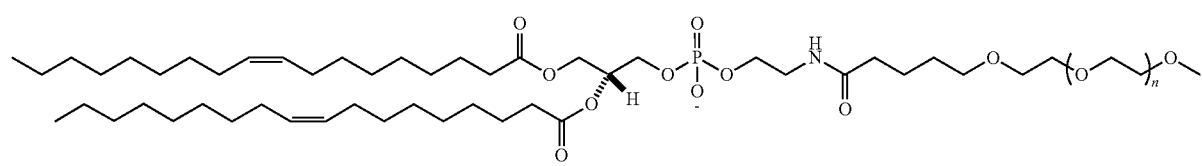
wherein n is an integer from 40 to 50.
In an embodiment, (i) is
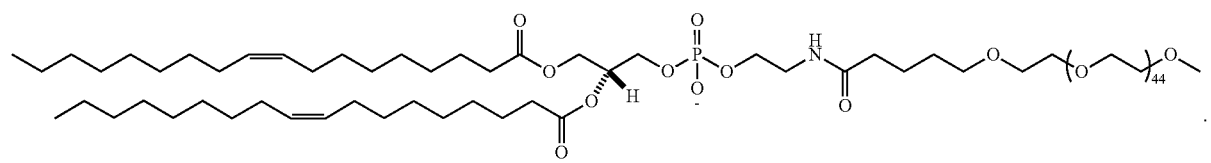

In another aspect, provided herein is a lipid nanoparticle comprising:
(i) a PEG-conjugated phospholipid (PEG-phospholipid) of Formula A:

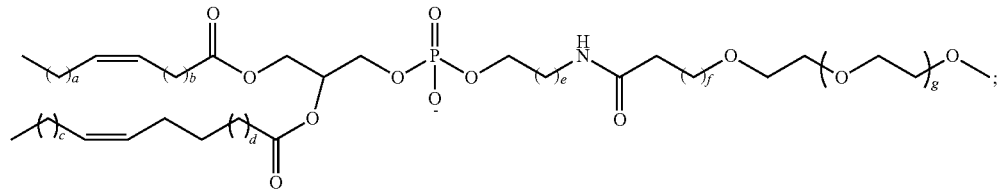

wherein
- a is an integer between 1 and 10;
- b is an integer between 1 and 10;
- c is an integer between 1 and 10;
- d is an integer between 1 and 10;
- e is an integer between 1 and 5;
- f is an integer between 1 and 5; and
- g is an integer between 10 and 50;

(ii) an ionizable lipid of Formula B:

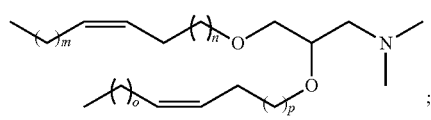

wherein
- m is an integer between 1 and 10;
- n is an integer between 1 and 10;
- is an integer between 1 and 10; and
- p is an integer between 1 and 10;

(iii) a non-cationic phospholipid of Formula C:

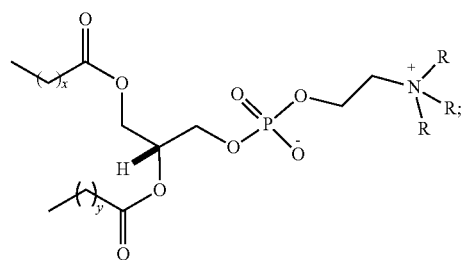

wherein
- x is an integer between 10 and 20;
- y is an integer between 10 and 20; and
- each R is independently $C_{1-6}$ alkyl; and (iv) a sterol of Formula D:

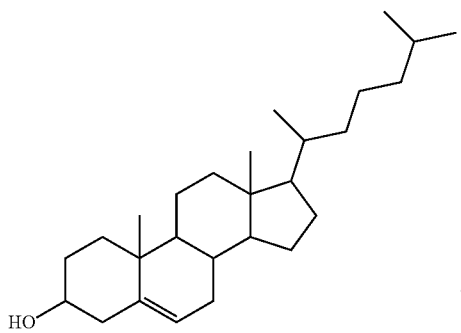

In an embodiment, in Formula A:
- a is an integer between 5 and 10;
- b is an integer between 5 and 10;
- c is an integer between 5 and 10;
- d is an integer between 1 and 5;
- e is an integer between 1 and 3;
- f is an integer between 1 and 5; and
- g is an integer between 30 and 50.

In another embodiment, Formula A is

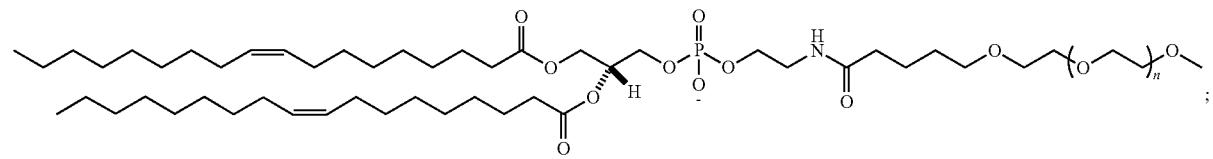

In an embodiment of Formula A, n is 40, 41, 42, 43, 44, 45, 46, 47, or 48. In another embodiment of Formula A, n is 44.

In yet another embodiment, in Formula B:
m is an integer between 5 and 10;
n is an integer between 5 and 10;
o is an integer between 5 and 10; and
p is an integer between 5 and 10.
In still another embodiment, Formula B is

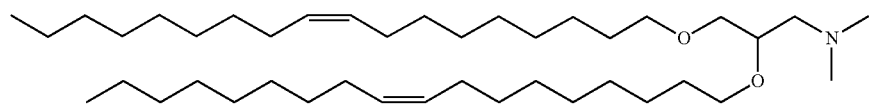 [SMILES: CCCCCCCC/C=C\CCCCCCCCOCC(CN(C)C)OCCCCCCCC/C=C\CCCCCCCC]

In an embodiment, in Formula C:
x is an integer between 15 and 20;
y is an integer between 15 and 20; and
each R is independently $C_{1-3}$ alkyl.
In another embodiment, Formula C is

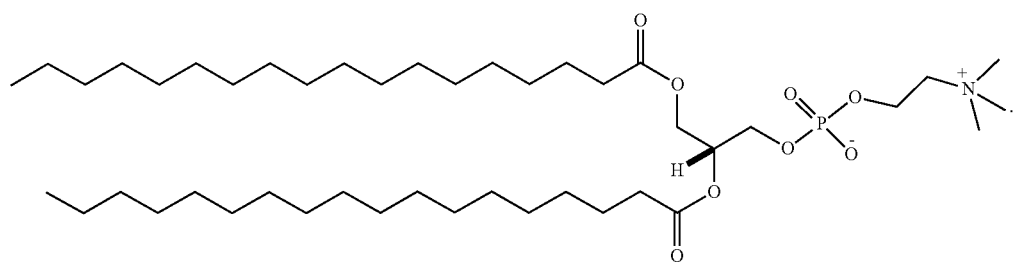

In yet another embodiment, Formula D is

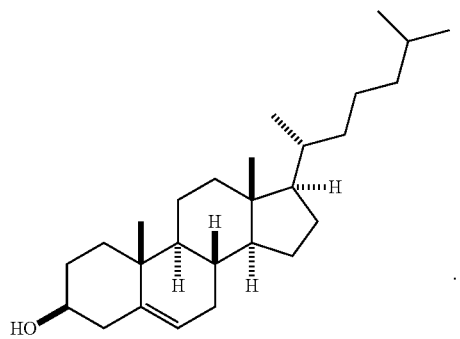

In an embodiment, provided herein is a pharmaceutical composition comprising the lipid nanoparticle and a pharmaceutically acceptable carrier.

In another embodiment, provided herein is a drug delivery system comprising the lipid nanoparticle and an active agent. In an embodiment, the drug delivery system is a nucleic acid delivery system comprising nucleic acids encapsulated by lipid nanoparticles.

Therapeutic Agents

The lipid nanoparticles provided herein are capable of carrying and delivering many different therapeutic agents. The therapeutic agents carried by lipid nanoparticles provided herein include, but are not limited to: nucleic acids (e.g., messenger RNA (mRNA)), small interfering RNA (siRNA), long non-coding RNA (lncRNA), antisense oligonucleotides, ribozymes, DNAzymes, plasmids, self-amplifying RNA (saRNA), DNA aptamers, gene therapy, microRNAs, RNA decoys, anti-miRs, immunostimulatory RNA (isRNA), and circular RNAs); proteins and peptides (e.g., cyclosporine A, immunoglobulin G, insulin, alpha-lactalbumin, bovine serum albumin, adamantyltripeptides, anti-ovalbumin antibodies, basic fibroblast growth factor, calcitonin, enkephalin, epidermal growth factor receptor, erythropoietin, gonadorelin, haptides, hemoglobin, horseradish peroxidase, human gamma-globulin, human recombinant EPG, *leishmania* antigen, leridistim, leuprolide, lysozime, nerve growth factor, octreotide, progenipoietin, recombinant malaria protein antigens, streptavidin, superoxide dismutase, TAT peptide, and thymopentin); and chemotherapeutic agents (cisplatin, docetaxel, doxorubicin, etoposide, gemcitabine, mitoxantrone, paclitaxel, retinoic acid, sorafenib, and zoledronate). The siRNA therapeutic agents include but are not limited to TTR siRNA, ALAS1 siRNA, HAO1 siRNA, ANGPTL3 siRNA, PCSK9 siRNA, and AGT siRNA. The mRNA therapeutic agents include but are not limited to mRNA-1273 (also known as Spikevax) and BNT162b2 (also known as Comirnaty), the coronavirus vaccines as well as CRISPR gene-editing therapies (wherein the guide RNA (gRNA) can be a single guide RNA (sgRNA) or gRNA plasmid and the Cas protein can be a Cas protein, Cas plasmid, or Cas mRNA).

In certain embodiments, the therapeutic agent carried by the lipid nanoparticle is an anionic drug agent. Examples of the anionic pharmacologically active substance useful in the present invention include bortezomib, methotrexate, olopatadine, tiotropium, ipratropium, glycopyrronium, aclidinium, umeclidinium, trospium, alendronic acid, ibandronic acid, incadronic acid, pamidronic acid, risedronic acid, zoledronic acid, etidronic acid, clodronic acid, tiludronic acid, olpadronic acid, neridronic acid, diclofenac, levocabastine, indomethacin, ibuprofene, flurbiprofen, fenoprofen, ketoprofen, naproxene, diclofenac, etodolac, sulindac, tolmetin, salicylic acid, difiunisal, oxaprozin, tiagabine, gabapentin, ciprofloxacin, levofloxacin, fusidic acid, aminolevulinic acid, aminocaproic acid, isopropamide iodide, trihexethyl chloride, cephalexin, aspirin, indoprofen, levodopa, methyldopa, zomepirac, cefamandole, alclofenac, mefenamic acid, flufenamic acid, lisinopril, enalapril, enalaprilat, captopril, ramipril, fosinopril, benazepril, quinapril, temocapril, cilazapril, valsartan, valproic acid, cromoglicic acid, tranilast, pantothenic acid, metiazinic acid, fentiazac, fenbufen, pranoprofen, loxoprofen, dexibuprofen, alminoprofen, tiaprofenic acid, aceclofenac, nalidixic acid, azelaic acid, mycophenolic acid, leucovorin, ethacrynic acid, tranexamic acid, ursodeoxycholic acid, folic acid, meclofenamic acid, carbenicillin, rebamipide, cetirizine, fexofenadine, letosteine, probenecid, hopantenic acid, baclofen, furosemide, piretanide, methyldopa, pravastatin, liothyronine, levothyroxine, minodronic acid, P-aminosalicylic acid, gluconic acid, biotin, liraglutide, exenatide, taspoglutide, albiglutide, lixisenatide, interferon alpha, interferon beta, interferon gamma, glucagon-like peptides, adrenocorticotropic hormone, insulin and insulin-like growth factors, parathyroid hormone and its fragments, darbepoetin alpha, epoetin alpha, epoetin beta, epoetin delta, infliximab, insulin, glucagon, glucagon-like peptides, thyrotropin hormone, thyroid stimulating hormone, parathyroid hormone, calcitonin, adrenocorticotropic hormone (ACTH), follicle stimulating hormone, chorionic gonadotropin, gonadotropin releasing hormone, somatropin, GRF, lypressin, luteinizing hormone, interleukin, growth hormone, prostaglandin, platelet-derived growth factors (PDGF), keratinocyte growth factors (KGF), fibroblast growth factors (FGF), epidermal growth factors (EGF), transforming growth factor-$\alpha$ (TGF-$\alpha$), transforming growth factor-$\beta$ (TGF-$\beta$), erythropoietin (EPO), insulin-like growth factor-I (IGF-I), insulin-like growth factor-II (IGF-II), tumor necrosis factor-$\alpha$ (TNF-$\alpha$), tumor necrosis factor-$\beta$ (TNF-$\beta$), colony stimulating factors (CSF), granulocyte colony stimulating factor (G-CSF), granulocyte macrophage colony stimulating factor (GM-CSF), vascular cell growth factor (VEGF), thrombopoietin (TPO), stromal cell-derived factors (SDF), placenta growth factor (PIGF), hepatocyte growth factor (HGF), glial-derived neurotropin factor (GDNF), ciliary neurotrophic factor (CNTF), bone growth factors, bone morphogenetic proteins (BMF), coagulation factors, human pancreas hormone releasing factor, analogues and derivative thereof, pharmaceutically acceptable salts thereof, and a combination thereof.

Preferably, the anionic pharmacologically active substance may be selected from the group consisting of bortezomib, methotrexate, olopatadine, liraglutide, exenatide, taspoglutide, albiglutide, lixisenatide, interferon alpha, interferon beta, interferon gamma, tiotropium, ipratropium, glycopyrronium, aclidinium, umeclidinium, trospium, alendronic acid, ibandronic acid, incadronic acid, pamidronic acid, risedronic acid, zoledronic acid, etidronic acid, clodronic acid, tiludronic acid, olpadronic acid, neridronic acid, glucagon-like peptides, adrenocorticotropic hormone, insulin and insulin-like growth factors, parathyroid hormone and its fragments, darbepoetin alpha, epoetin alpha, epoetin beta, epoetin delta, diclofenac, levocabastine, indomethacin, ibuprofene, flurbiprofen, fenoprofen, ketoprofen, naproxene, diclofenac, etodolac, sulindac, tolmetin, salicylic acid, difiunisal, oxaprozin, tiagabine, gabapentin, ciprofloxacin, levofloxacin, fusidic acid, aminolevulinic acid, a pharmaceutically acceptable salt thereof, and a combination thereof.

In certain embodiments, self-amplifying RNA (saRNA) may also be referred to as self-replicating RNA, replication-competent RNA, replicons or RepRNA. RepRNA, referred to as self-amplifying mRNA when derived from positive-strand viruses, is generated from a viral genome lacking at least one structural gene; it can translate and replicate (hence, "self-amplifying") without generating infectious progeny virus. In certain embodiments, the RepRNA technology may be used to insert a gene cassette encoding a desired antigen of interest. For example, the alphaviral genome is divided into two open reading frames (ORFs): the first ORF encodes proteins for the RNA dependent RNA polymerase (replicase), and the second ORF encodes structural proteins. In saRNA vaccine constructs, the ORF encoding viral structural proteins may be replaced with any antigen of choice, while the viral replicase remains an integral part of the vaccine and drives intracellular amplification of the RNA after immunization.

Methods of Delivering Therapeutic Agents

The present disclosure provides methods of delivering a therapeutic and/or prophylactic to a mammalian cell, tissue, or organ. Provided herein is a method of delivering a therapeutic and/or prophylactic to a cell by administering a nanoparticle composition including the therapeutic and/or prophylactic to a subject, where administration of the composition involves contacting the cell with the composition. For example, a protein, cytotoxic agent, radioactive ion, chemotherapeutic agent, nucleic acid (such as an RNA, e.g., mRNA), or gene editing system may be delivered to a cell or organ. In the instance that the therapeutic and/or prophylactic is a CRISPR system, the guide RNA can be a single guide RNA (sgRNA) or gRNA plasmid and the associated DNA modifying enzyme(s) can be delivered as a protein, plasmid, or mRNA). If the therapeutic and/or prophylactic is an mRNA, upon contacting a cell with the nanoparticle composition, a translatable mRNA may be translated in the cell to produce a polypeptide of interest. However, mRNAs that are substantially not translatable may also be delivered to cells. Substantially non-translatable mRNAs may be useful as vaccines and/or may sequester translational components of a cell to reduce expression of other species in the cell.

The compositions and methods of the present disclosure are used to treat a wide variety of cell types, in vivo and in vitro. Suitable cells include, but are not limited to, hematopoietic precursor (stem) cells, fibroblasts, keratinocytes, hepatocytes, endothelial cells, skeletal and smooth muscle cells, osteoblasts, osteoclasts, pancreatic endocrine cells (alpha cells, beta cells, PP cells, delta cells, and epsilon cells), pituitary endocrine cells, neurons, quiescent or activated lymphocytes, terminally differentiated cells, slow or noncycling primary cells, parenchymal cells, lymphoid cells, epithelial cells, bone cells, and the like. In one embodiment, an nucleic acid, such as one or more nucleic acid molecules (e.g., an interfering RNA (e.g., siRNA) or mRNA) is delivered to cancer cells such as, e.g., lung cancer cells, colon cancer cells, rectal cancer cells, anal cancer cells, bile duct cancer cells, small intestine cancer cells, stomach (gastric) cancer cells, esophageal cancer cells, gallbladder cancer cells, liver cancer cells, pancreatic cancer cells, appendix cancer cells, breast cancer cells, ovarian cancer cells, cervical cancer cells, prostate cancer cells, renal cancer cells, cancer cells of the central nervous system, glioblastoma tumor cells, skin cancer cells, lymphoma cells, choriocarcinoma tumor cells, head and neck cancer cells, osteogenic sarcoma tumor cells, and blood cancer cells.

In vivo delivery of lipid nanoparticles encapsulating one or more nucleic acid molecules (e.g., interfering RNA (e.g., siRNA) or mRNA) is suited for targeting cells of any cell type. The methods and compositions can be employed with cells of a wide variety of vertebrates, including mammals, such as, e.g., canines, felines, equines, bovines, ovines, caprines, rodents (e.g., mice, rats, and guinea pigs), lagomorphs, swine, and primates (e.g., monkeys, chimpanzees, and humans).

A nanoparticle composition including one or more therapeutic and/or prophylactic can be administered by any route.

In some embodiments, compositions, including prophylactic, diagnostic, or imaging compositions including one or more nanoparticle compositions described herein, are administered by one or more of a variety of routes, including oral, intravenous, intramuscular, intra-arterial, intramedullary, intrathecal, subcutaneous, intraventricular, trans- or intra-dermal, interdermal, rectal, intravaginal, intraperitoneal, intraocular, subretinal, intravitreal, topical (e.g., by powders, ointments, creams, gels, lotions, and/or drops), mucosal, nasal, buccal, enteral, vitreal, intratumoral, sublingual, intranasal; by intratracheal instillation, bronchial instillation, and/or inhalation; as an oral spray and/or powder, nasal spray, and/or aerosol, and/or through a portal vein catheter. In some embodiments, a composition may be administered intravenously, intramuscularly, intradermally, intra-arterially, intratumorally, subcutaneously, intraocularly, subretinally, intravitreally, or by inhalation. However, the present disclosure encompasses the delivery or administration of compositions described herein by any appropriate route taking into consideration likely advances in the sciences of drug delivery. In general, the most appropriate route of administration will depend upon a variety of factors including the nature of the nanoparticle composition including one or more therapeutic and/or prophylactic (e.g., its stability in various bodily environments such as the bloodstream and gastrointestinal tract), the condition of the patient (e.g., whether the patient is able to tolerate particular routes of administration), etc.

Treating Disease with Therapeutic Agents Delivered by Lipid Nanoparticles

The nanoparticle compositions provided herein can be useful for treating a disease, disorder, or condition. Such compositions can be useful in treating a disease, disorder, or condition characterized by missing or aberrant protein or polypeptide activity. Examples of such human diseases include X-linked severe combined immunodeficiency (X-SCID) and adrenoleukodystrophy (X-ALD). X-SCID is caused by one or more mutations in the gene encoding the common gamma chain protein that is a component of the receptors for several interleukins that are involved in the development and maturation of B and T cells within the immune system. X-ALD is caused by one or more mutations in a peroxisomal membrane transporter protein gene called ABCD1. Individuals afflicted with X-ALD have very high levels of long chain fatty acids in tissues throughout the body, which causes a variety of symptoms that may lead to mental impairment or death.

A nanoparticle composition comprising an mRNA encoding a missing or aberrant polypeptide may be administered or delivered to a cell. Subsequent translation of the mRNA may produce the polypeptide, thereby reducing or eliminating an issue caused by the absence of or aberrant activity caused by the polypeptide. Because translation may occur rapidly, the methods and compositions may be useful in the treatment of acute diseases, disorders, or conditions such as sepsis, stroke, and myocardial infarction. A therapeutic and/or prophylactic included in a nanoparticle composition may also be capable of altering the rate of transcription of a given species, thereby affecting gene expression.

Diseases, disorders, and/or conditions characterized by dysfunctional or aberrant protein or polypeptide activity for which a composition may be administered include, but are not limited to, rare diseases, infectious diseases (as both vaccines and therapeutics), cancer and proliferative diseases, genetic diseases (e.g., cystic fibrosis, Wilson's disease, hemophilia, phenylketonuria, and alpha-1-antitrypsin deficiency), autoimmune diseases, diabetes, neurodegenerative diseases, cardio- and reno-vascular diseases, and metabolic diseases. Multiple diseases, disorders, and/or conditions may be characterized by missing or substantially diminished protein activity. Such proteins may not be present, or they may be essentially non-functional. A specific example of a dysfunctional protein is the missense mutation variants of the cystic fibrosis transmembrane conductance regulator (CFTR) gene, which produce a dysfunctional protein variant of CFTR protein, which causes cystic fibrosis.

Proteins and mRNA can also be presented to treat or prevent endemic diseases, such as those caused by bacteria and viruses. For example, lipid nanoparticle carriers played an important role in delivering the coronavirus vaccines mRNA-1273 (also known as Spikevax) and BNT162b2 (also known as Comirnaty). Once each of these treatments was administered, the mRNA within the vaccine led to the production of the coronavirus spike protein. Thus, the treatment here did not replace a missing protein, rather it led to the production of a foreign protein which in turn triggered an adaptive immune response.

The present disclosure provides a method for treating such diseases, disorders, and/or conditions in a subject by administering a nanoparticle composition including an RNA and a lipid mixture including functional lipid components according to LNP-1, an ionizable lipid that is unsaturated and cationic at low pH, an optionally unsaturated phospholipid, a PEG lipid (such as L1A), and a structural lipid (such as sterol), wherein the RNA may be an mRNA encoding a polypeptide that antagonizes or otherwise overcomes an aberrant protein activity present in the cell of the subject.

The disclosure provides methods involving administering nanoparticle compositions including one or more therapeutic and/or prophylactic agents and pharmaceutical compositions including the same. The terms therapeutic and prophylactic can be used interchangeably herein with respect to features and embodiments of the present disclosure. Therapeutic compositions, or imaging, diagnostic, or prophylactic compositions thereof, may be administered to a subject using any reasonable amount and any route of administration effective for preventing, treating, diagnosing, or imaging a disease, disorder, and/or condition and/or any other purpose. The specific amount administered to a given subject may vary depending on the species, age, and general condition of the subject; the purpose of the administration; the particular composition; the mode of administration; and the like. Compositions in accordance with the present disclosure may be formulated in dosage unit form for ease of administration and uniformity of dosage. It will be understood, however, that the total daily usage of a composition of the present disclosure will be decided by an attending physician within the scope of sound medical judgment. The specific therapeutically effective, prophylactically effective, or otherwise appropriate dose level (e.g., for imaging) for any particular patient will depend upon a variety of factors including the severity and identify of a disorder being treated, if any; the one or more therapeutic and/or prophylactic employed; the specific composition employed; the age, body weight, general health, sex, and diet of the patient; the time of administration, route of administration, and rate of excretion of the specific pharmaceutical composition employed; the duration of the treatment; drugs used in combination or coincidental with the specific pharmaceutical composition employed; and like factors well known in the medical arts.

Nanoparticle compositions including one or more therapeutic and/or prophylactic may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. For example, one or more nanoparticle compositions including one or more different therapeutic and/or prophylactic may be administered in combination. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions, or imaging, diagnostic, or prophylactic compositions thereof in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination will be utilized at levels that do not exceed the levels at which they are utilized individually. In some embodiments, the levels utilized in combination may be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions).

A nanoparticle composition may be used in combination with an agent to increase the effectiveness and/or therapeutic window of the composition. Such an agent may be, for example, an anti-inflammatory compound, a steroid (e.g., a corticosteroid), a statin, an estradiol, a BTK inhibitor, an S1P1 agonist, a glucocorticoid receptor modulator (GRM), or an antihistamine. In some embodiments, a nanoparticle composition may be used in combination with dexamethasone, methotrexate, acetaminophen, an H1 receptor blocker, or an H2 receptor blocker. In some embodiments, a method of treating a subject in need thereof or of delivering a therapeutic and/or prophylactic to a subject (e.g., a mammal) may involve pre-treating the subject with one or more agents prior to administering a nanoparticle composition. For example, a subject may be pre-treated with a useful amount (e.g., 10 mg, 20 mg, 30 mg, 40 mg, 50 mg, 60 mg, 70 mg, 80 mg, 90 mg, 100 mg, or any other useful amount) of dexamethasone, methotrexate, acetaminophen, an H1 receptor blocker, or an H2 receptor blocker. Pre-treatment may occur 24 or fewer hours (e.g., 24 hours, 20 hours, 16 hours, 12 hours, 8 hours, 4 hours, 2 hours, 1 hour, 50 minutes, 40 minutes, 30 minutes, 20 minutes, or 10 minutes) before administration of the nanoparticle composition and may occur one, two, or more times in, for example, increasing dosage amounts.

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

Formulations

Formulations suitable for oral administration can consist of: (a) liquid solutions, such as an effective amount of a packaged therapeutic agent such as nucleic acid (e.g., interfering RNA, mRNA, or DNA) suspended in diluents such as water, saline, or PEG 400; (b) capsules, sachets, or tablets, each containing a predetermined amount of a therapeutic agent such as nucleic acid (e.g., interfering RNA, mRNA, or DNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic agent such as nucleic acid (e.g., interfering RNA, mRNA, or DNA) in a flavor, e.g., sucrose, as well as pastilles comprising the therapeutic agent in an inert base, such as gelatin and glycerin or sucrose and acacia emulsions, gels, and the like containing, in addition to the therapeutic agent, carriers known in the art.

In another example of their use, lipid nanoparticles can be incorporated into a broad range of topical dosage forms. For instance, a suspension containing nucleic acid-lipid nanoparticles can be formulated and administered as gels, oils, emulsions, topical creams, pastes, ointments, lotions, foams, mousses, and the like.

EXAMPLES

Exemplary Materials and Methods

Reagents: All chemicals, cell culture media, and commercial antibodies were purchased from Thermo Fisher Scientific (Waltham, MA), and cell culture consumables from CELLTREAT® Scientific Products (Shirley, MA) and Thermo Fisher Scientific, unless otherwise stated. All mRNAs and guide RNAs were synthesized by GenScript (Piscataway, NJ), except GFP mRNA from System Biosciences (Palo Alto, CA) and siRNA targeting mouse ApoB from Thermo Fisher Scientific. Phospholipids, polysorbates, and excipients were purchased from Avanti Polar Lipids Inc./CRODA (Alabaster, AL), Lysan Bio Inc. (Arab, AL), Cayman Chemical Company (Ann Arbor, MI), and NOF Corporation (White Plains, NY), unless otherwise specified. Sterol standard for clinical use was purchased from MP Biomedicals (Solon, OH).

L1A PEG-lipid synthesis: PEG-phospholipid L1A was synthesized at CodeBridgeBio Lab (Woburn, MA). Briefly, Starting Material 1 (SM1) (exemplary: 2-aminoethyl ((R)-2-3bis-(oleoyloxy) propyl) phosphate, DOPE) was dissolved in a solution of Starting Material 2 (SM2) (exemplary: mPEG-SVA Methoxy Poly (Ethylene Glycol) Succinimidyl Valerate, mPEG-SVA) in Chloroform at a mol ratio of 1.1:1, followed by the slow addition of Triethyl amine (10% mol, TEA). The resulting solution mixture was stirred gently overnight at 25° C. Thin-layer chromatography (TLC) with chloroform/methanol/water (100:10:2, v:v:v) was used to monitor the reaction. When the broad spot of the SM2 disappeared and subsequently a new polar well-defined spot appeared, the solvent was evaporated. Acetonitrile was added to dissolve the white-pale yellow powder, and the resulting solution mixture was kept at −20° C.

overnight (4° C. can be also used). After centrifugation at 14,000 rpm (>5000 rpm can be also used) for 30 minutes, the upper solution without insoluble SM1 was collected and lyophilized at −80° C. overnight. The lyophilized white powder was analyzed for identity, purity, and integrity by proton (1H) NMR, LC-MS (ESI) and HPLC with ELSD High resolution mass spectroscopy negative ion mode method.

LNP-1 lipid nanoparticle preparation: PEG-phospholipid (using L1A as an exemplary presentation) and together with the other three complementary lipid components were used for engineering the LNP-1 LNP Platform Technology (e.g., four lipid components [Ionizable Lipid:Cholesterol:DSPC:L1A=50:39.25:10:0.75 mol %]). In brief, LNPs were prepared by mixing an ethanol phase containing lipids with RNA in an aqueous phase in an Ignite NanoAssemblr microfluid mixing device (Precision Nanosystem Inc., Vancouver, British Columbia, Canada) following the manufacturer's instructions. The ethanol phase was prepared by solubilizing a mixture of ionizable lipid (e.g., DODMA, DODAP, DLin-DMA, DLin-MC3-DMA, ALC-0315, or SM-102), cholesterol, DSPC, and L1A at a predetermined molar ratio in ethanol. The aqueous phase was prepared in 25 mM citrate buffer (pH 3.75±0.25) with RNA. Syringe pumps were used to mix the aqueous and ethanol phases at a ratio of 3:1. The resulting RNA-LNPs were first diafiltrated in citrate buffer (pH 4.0) to remove ethanol and strength the lipo-complex binding and then dialyzed twice against PBS (pH 7.4) for ≥12 hours and 4 hours, respectively. The final RNA-LNPs drug product formulation buffer solution (pH 7.4±0.2, −18.7±0.8 mV at 25° C.) contains 10.14 mM Sodium Phosphate Dibasic, 1.76 mM Potassium Phosphate Monobasic, 2.7 mM Potassium Chloride, 137 mM Sodium Chloride, and Nuclease-free Water (not DEPC-treated).

Figure 5:
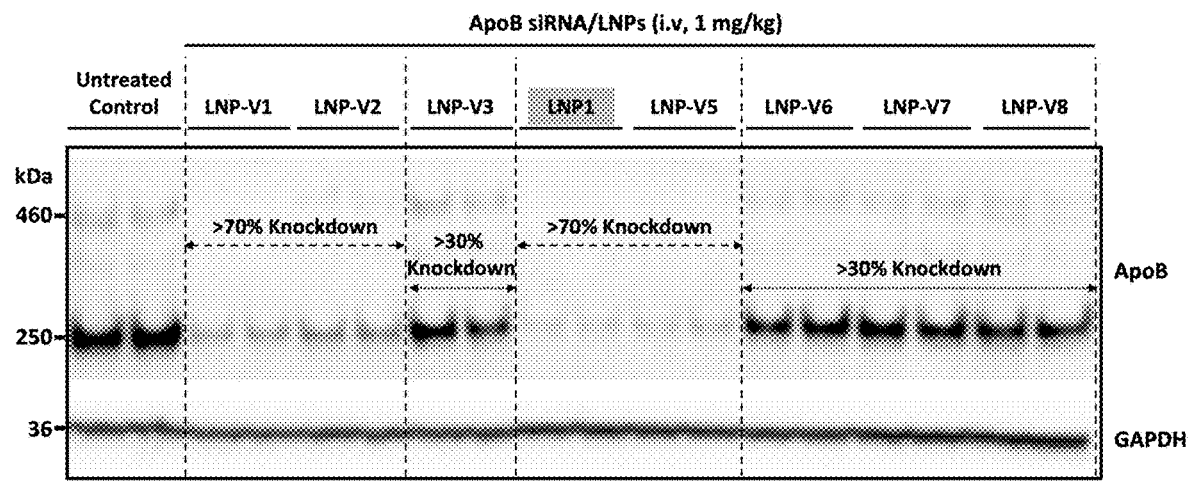
FIG. 5 shows LNP-1 platform's flexibility with molar ratios of four lipid components.

For FIG. 5: ApoB siRNA/LNPs were prepared as described above, except using varied molar ratios of four lipid components (DODMA:Cholesterol:DSPC:L1A).

Figure 6:
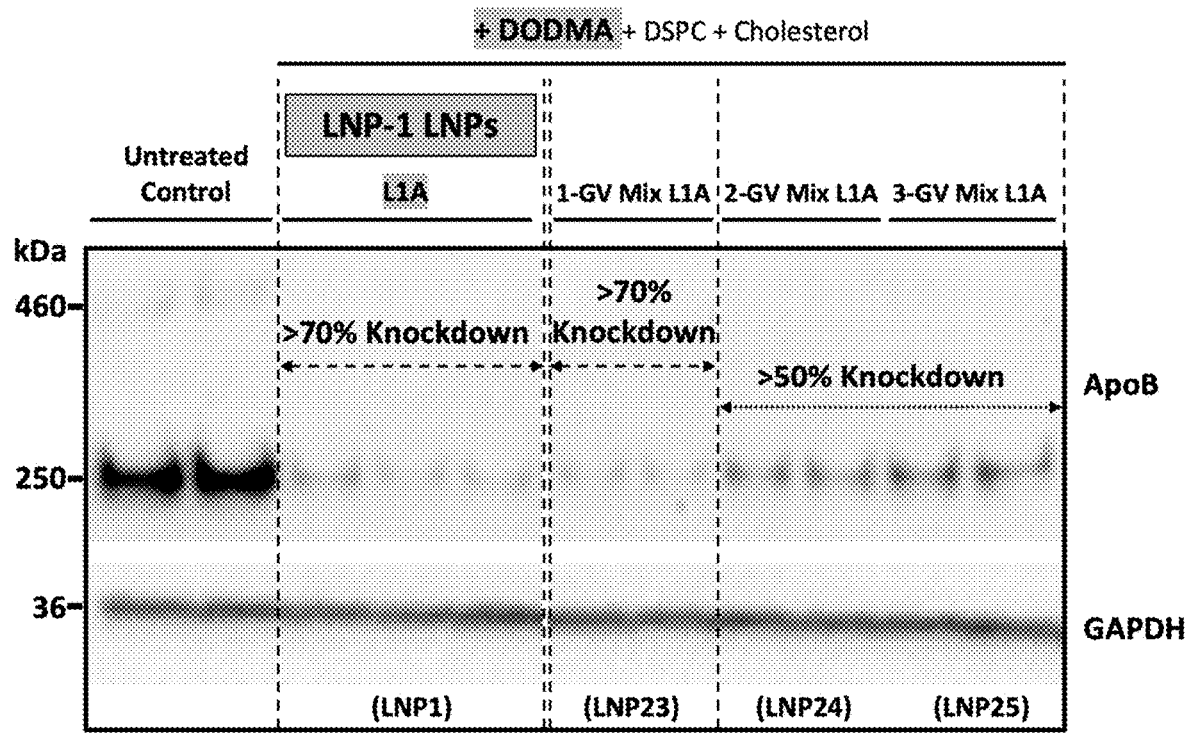
FIG. 6 shows LNP-1 platform's flexibility with microfluid buffer for LNPs preparation.

For FIG. 6: ApoB siRNA/LNPs were prepared as described above, except using different microfluid buffers (Exemplary: citrate buffer versus acetate buffer; and a fixed buffer at different concentrations (Exemplary: 25-100 mM) to evaluate the effect of ionic strength on the making of LNPs). The buffers used here are listed in the bottom.

Encapsulation efficiency quantification of RNAs/LNP-1 lipid nanoparticles: To quantify the RNAs loaded into LNP-1 LNPs and to determine the RNAs encapsulation efficiency, OD Nanodrop One spectroscopy for preparing stock solution at high concentration and the highly sensitive read-out Quant-iT RiboGreen RNA assay from Thermo Fisher Scientific were used according to the manufacturer's protocols. An exemplary RNA payload quantification method with technical details is shown in FIG. 7.

Physical characterization of RNAs/LNP-1 lipid nanoparticles formulations: Size distribution and Zeta potential of RNAs/LNP-1 LNPs formulations were determined by Dynamic Light Scattering (DLS) using a Malvern Nano Zetasizer Ultra Red (Malvern Panalytical Inc, Westborough, MA). For size measurements, RNAs/LNP-1 LNPs were diluted 1:15 in PBS (pH 7.20). For Zeta potential (Charge) measurements, RNAs/LNP-1 LNPs were diluted 1:50 in Nuclease-Free Water (not DEPC-Treated).

Chemical characterization of RNAs/LNP-1 lipid nanoparticles formulations: Lipid composition of RNAs/LNP-1 LNPs formulations was determined by HPLC-ELSD/CAD; PEG-phospholipid L1A's identity was confirmed by 1D proton NMR spectrum and LC-MS (ESI), L1A's integrity was confirmed by HRMS negative ion mode method HPLC-ELSD, and L1A's purity was confirmed by HPLC-ELSD; all through external CRO services provided by Pace Analytical Life Sciences (Woburn, MA).

Morphology and lamellarity characterization of RNAs/LNP-1 lipid nanoparticles formulations: This was analyzed using Cryo Transmission Electron Microscopy (Cryo-TEM) imaging through external CRO services provided by Nanolmaging Services Inc. (San Diego, CA).

Cell culture: Jurkat human T leukemia cells, THP-1 human monocytic leukemia cells and HCC1739BL human lymphoma cells were cultured in RPMI-1640 and HepG2 human liver cancer cells in EMEM, supplemented with 10% FBS, 1% penicillin-streptomycin, and were maintained in culture flasks at 37° C. in a 5% $CO_2$ atmosphere at 100% humidity (cell culture incubator). For eGFP mRNA/LNP-1 LNPs studies, cells were seeded in a 96-well plate and then incubated with eGFP mRNA/LNP-1 LNPs in a cell culture incubator. At the end of the study, intracellular GFP expression signal was evaluated by flow cytometry (for Jurkat, THP-1 and HCC1739BL cells) or by fluorescence microscopy (for HepG2 cells). Cells without LNPs treatment served as untreated controls.

Ex vivo CAR-T generation: T cells purified from human PBMCs were activated for 7 days in a cell culture incubator. On day 8, cells were transfected with CAR (eGFP) mRNA loaded LNP-1 LNPs for 48 hours, then CAR expression was examined as intracellular GFP signal by flow cytometry, in parallel with CAR-T cell viability assay.

In vivo CAR-T generation: NSG mice were reconstituted with 20*106 of human PBMCs, followed by intravenous (i.v) administration of CAR (eGFP) mRNA loaded LNP-1 LNPs (3 mg/kg) on day 7 post engraftment. Mouse blood was collected on days 2 and 4 post transfection and analyzed by flow cytometry for in vivo CAR expression (intracellular GFP signal) in human CD45+ cell populations.

Hematopoietic stem cells differentiation to erythroblast cells: C57BL6 mouse bone marrow cells were cultured in the presence of erythrocyte differentiation media including cytokines (mIL-3/mEPO/mCSF) in a cell culture incubator for 7 days. Cells were then incubated with eGFP mRNA loaded LNP-1 LNPs for 48 hours, followed by flow cytometry analysis of intracellular GFP expression.

In vitro immune cell activation: Freshly purified mouse PBMCs incubated with 100 ng (=1 μg/ml) of eGFP mRNA loaded LNP-1 LNPs in the presence of cytokines (mM-CSF/mGM-CSF/mIL-4) in a cell culture incubator for 48 hours, then gene delivery potency was examined as intracellular GFP expression detected by flow cytometry.

Tail vein injection of RNAs/LNP-1 lipid nanoparticles and tissue processing: Eight to 12 weeks old C57BL/6 mice were intravenously (i.v) administrated with a single dose of LNP-1 LNPs loaded with RNA payloads such as ApoB siRNA or eGFP mRNA at 10 μL/gram body weight with dosages ranging from 0.1 mg/kg to 10 mg/kg. RNAs/LNP-1 LNPs were slowly injected through the mouse tail vein over 30 seconds using a 28 G needle. 48 hours later, potential target organs such as liver, spleen, kidneys, femur (for bone marrow), and blood were harvested for subsequent analyses.

Assessment of ApoB siRNA/LNP-1 LNPs in vivo knockdown efficiency: Tissue lysates were prepared from frozen livers as described above and then subjected for Western Blotting of mouse ApoB proteins. Na/K ATPase, eRF1 or GAPDH served as the internal loading control. Knockdown (KD) efficiency is calculated as the percentage (%) decrease of ApoB protein levels in treated livers in contrast to untreated livers.

Visualization of GFP mRNA expression in LNP-1 LNPs target organs: Freshly harvested bone marrow was made into single-cell suspensions and then dropped onto glass slides, covered with coverslips, and examined under a fluorescence microscope. Frozen sections of liver and spleen were examined for in situ intracellular GFP expression by fluorescence microscopy.

Spike mRNA/LNP-1 COVID-19 vaccine production: COVID-19 coronavirus Spike mRNA (benchmark Moderna mRNA-1273)/LNP-1 LNPs (5 µg in 50 µL PBS) were intramuscularly (IM) or subcutaneously (SC) injected into C57BL/6 or BALB/c mice on days 0 (the prime dose) and 21 (the boost dose). On days 14 (Prime), 28 (Boost-d7) and 44 (Boost-d23) for C57BL/6 mice or on days 28 (Post-Boost 1w), 35 (Post-Boost 2w) and 49 (Post-Boost 4w) for BALB/c mice, mouse blood were collected and examined for anti-Spike protein-RBD titres by ELISA. Mice received 50 µL PBS served as the negative control (labeled as PBS Ctrl or NC).

Example 1: An exemplary composition of the herein described lipid nanoparticle gene delivery platform technology known as LNP-1 (FIG. 1). In this embodiment, LNP-1 structural lipids include L1A (a PEG-phospholipid having two C18 aliphatic chains with one unsaturation bond in the fatty acid chain), DODMA (an ionizable lipid having two C18 aliphatic chains with one unsaturated site and a head group that protonates to a cationic moiety having a pKa of 5-7), DSPC (a non-cationic helper phospholipid having two saturated C18 aliphatic chains and a head group that remains as a zwitterion or anion across a pH range of 6 to 8), and cholesterol (a cell membrane stabilizer helper sterol lipid). An exemplary formulation buffer solution for RNA-LNPs drug product is also shown.

Example 2: A working example of the lipid composition and identity of the LNP-1 platform (FIG. 2). The lipid composition of LNP-1 formulations loaded with eGFP/mRNA was successfully confirmed at the expected values—the assay mmol % of each lipid component is comparable to the nominal value of their masses. Separation of four lipid components of LNP-1 formulations is obtained by UPLC-ELSD method.

Example 3: Confirmation of PEG-phospholipid L1A's synthesis, identity, purity and integrity (FIG. 3). PEGylated L1A was successfully synthesized-TLC Plate indicates that the Rxn of SM1 and SM2 took place and the PEGylated L1A spot was identified. PEGylated L1A was successfully identified at the expected mass from proton (1H) NMR spectra, and integrity confirmed with no impurity detected. RT shifts are predictable with sequential L1A PEGylation. L1A's PEGylation states (32 to 44 PEGs) was also confirmed.

Figure 4:
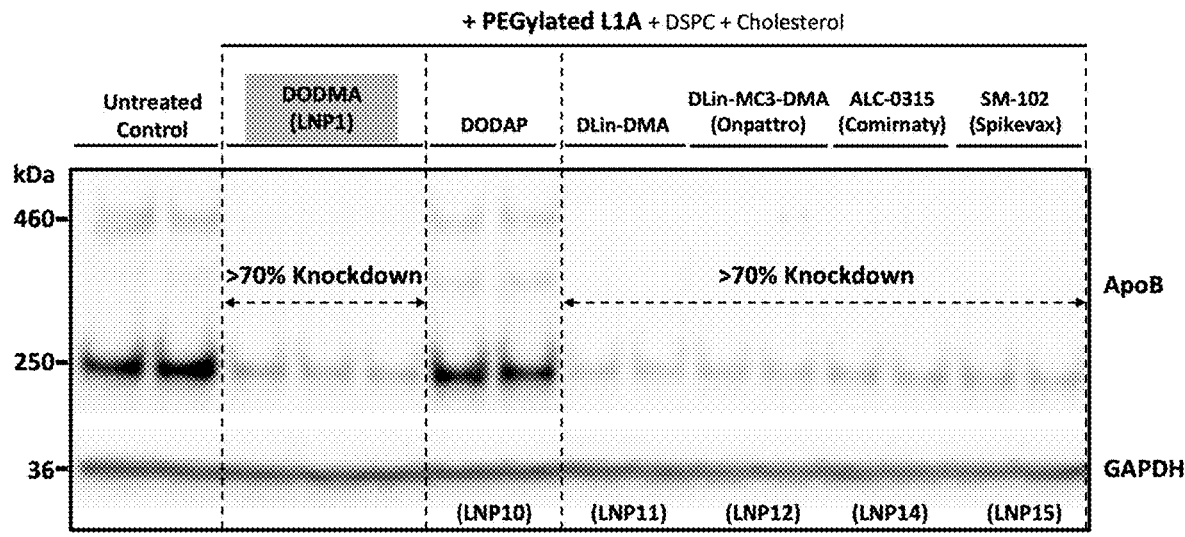
FIG. 4 shows LNP-1 platform's high compatibility of PEG-conjugated phospholipid and flexibility with structural ionizable lipid component.

Example 4: Working examples of LNP-1 platform's high compatibility of PEG-conjugated phospholipid and flexibility with structural ionizable lipid (IL) component (FIG. 4). In vivo gene silencing potency of the exemplary LNP-1 formulation-[DODMA:Cholesterol:DSPC:L1A=50:39.25:10:0.75 mol %] was compared to that of several other IL components clinical and commercially available with L1A, using ApoB siRNA as the payload. After 4 months storage at 2-8° C., all LNP formulations were intravenously (i.v) administrated (1 mg/kg) into C57BL/6 mice. 48 hours later, ApoB protein knockdown efficiency was evaluated by Western Blotting of liver tissue lysates. Livers from untreated mice served as controls for knockdown efficiency calculation-percentage (%) decrease of ApoB protein levels (including both monomeric and dimeric forms) in treated livers in contrast to untreated livers. GAPDH protein was used as the loading control. PEGylated L1A is highly compatible with DLin-DMA, DLin-MC3-DMA (Onpattro/Alnylam's IL component), ALC-0315 (Comirnaty/Pfizer-BioNTech's IL component), and SM-102 (Spikevax/Moderna's IL component)—all these new L1A LNP formulations achieved potent >70% knockdown efficiency similar to LNP1 (the exemplary LNP-1 formulation). The detailed lipid structures and formula as well as size and Zeta Potential measurements of all L1A LNP formulations are also shown.

Example 5: Working examples of LNP-1 platform's flexibility with molar ratios of four lipid components (FIG. 5). The in vivo gene silencing potency of the LNP-1 delivery platform was tested using varied molar ratios of four lipid components for LNP preparation (e.g., using ApoB siRNA as the payload and liver as the target organ). In vivo ApoB protein knockdown efficiency was examined as described in Example 4. In the liver, new LNP formulations V1, V2 and V5 achieved >70% knockdown efficiency similar to LNP1 (the exemplary LNP-1 formulation); and V3, V6, V7 and V8 also achieved >30% knockdown efficiency. The exact molar ratios of four lipid components as well as size and Zeta Potential measurements for all LNP formulations are also listed.

Example 6: Working examples of LNP-1 platform's flexibility with microfluid bufffer (FIG. 6). In vivo gene silencing potency of the LNP-1 delivery platform was tested using different microfluid buffers as well as a fixed buffer at different concentrations to evaluate the effect of ionic strength on the making of LNP (e.g., using ApoB siRNA as the payload and liver as the target organ). In vivo ApoB protein knockdown efficiency was examined as described in Example 4. The microfluid buffers used for all LNP formulations are listed in the bottom. 1-GV Mix L1A (LNP23) achieved >70% knockdown efficiency similar to LNP1 (the exemplary LNP-1 formulation); 2-GV Mix L1A (LNP24) and 3-GV Mix L1A (LNP25) achieved >50% knockdown efficiency.

Example 7: Working examples of RNA payload assay for LNP-1 LNPs (FIG. 7). The fluorescent Quanti-iT RNA RiboGreen Quantification method was used. OD measurements by NanoDrop One, Standard Curve formatting, and detailed technical procedures are shown.

Figure 8:
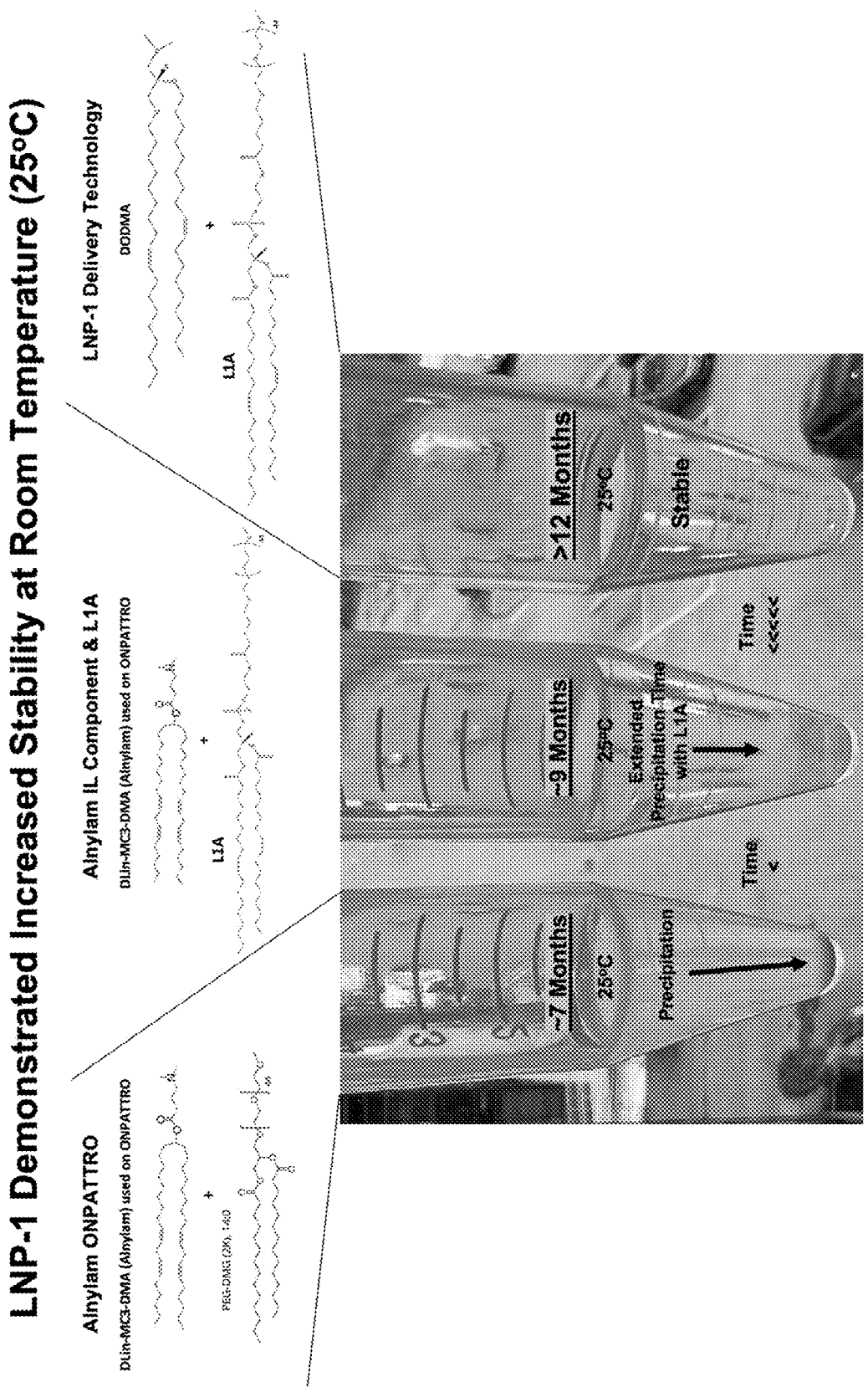
FIG. 8 shows that LNP-1 formulations demonstrated increased stability at room temperature (25° C.) when compared with other lipid nanoparticle formulations.

Example 8: LNP-1 formulations demonstrated increased stability at room temperature (25° C.) (FIG. 8). The stability of the LNP-1 delivery formulation was compared to that of Alnylam's IL component with L1A and Alnylam's ONPATTRO at room temperature (25° C.). Both combinations using Alnylam components precipitated out of solution, with Alnylam's ONPATTRO crashing out more quickly (~7 months) than the combination Alnylam IL component with L1A (~9 months). The LNP-1 formulation was able to remain in solution for an extended period of time (>12 months) indicating that it is more stable than the other two formulations.

Figure 9:
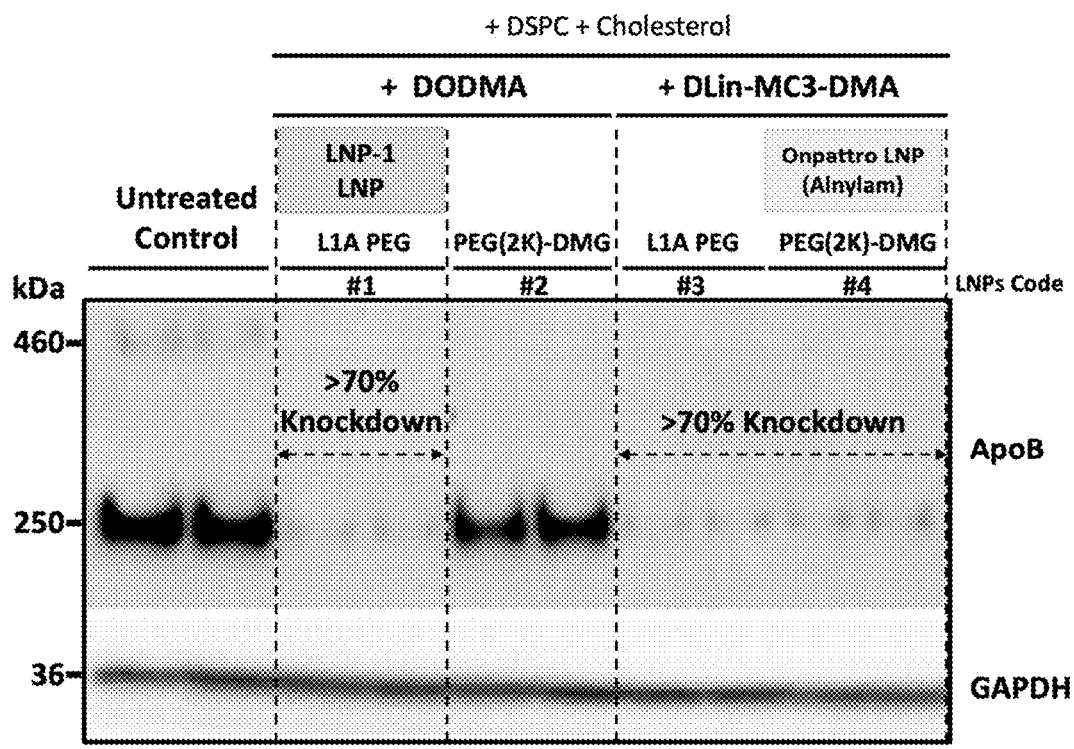
FIG. 9 shows that structural and functional stable PEGylated L1A is compatible with other ionizable lipids and PEGylated L1A LNPs have smaller sizes.
Figure 9:
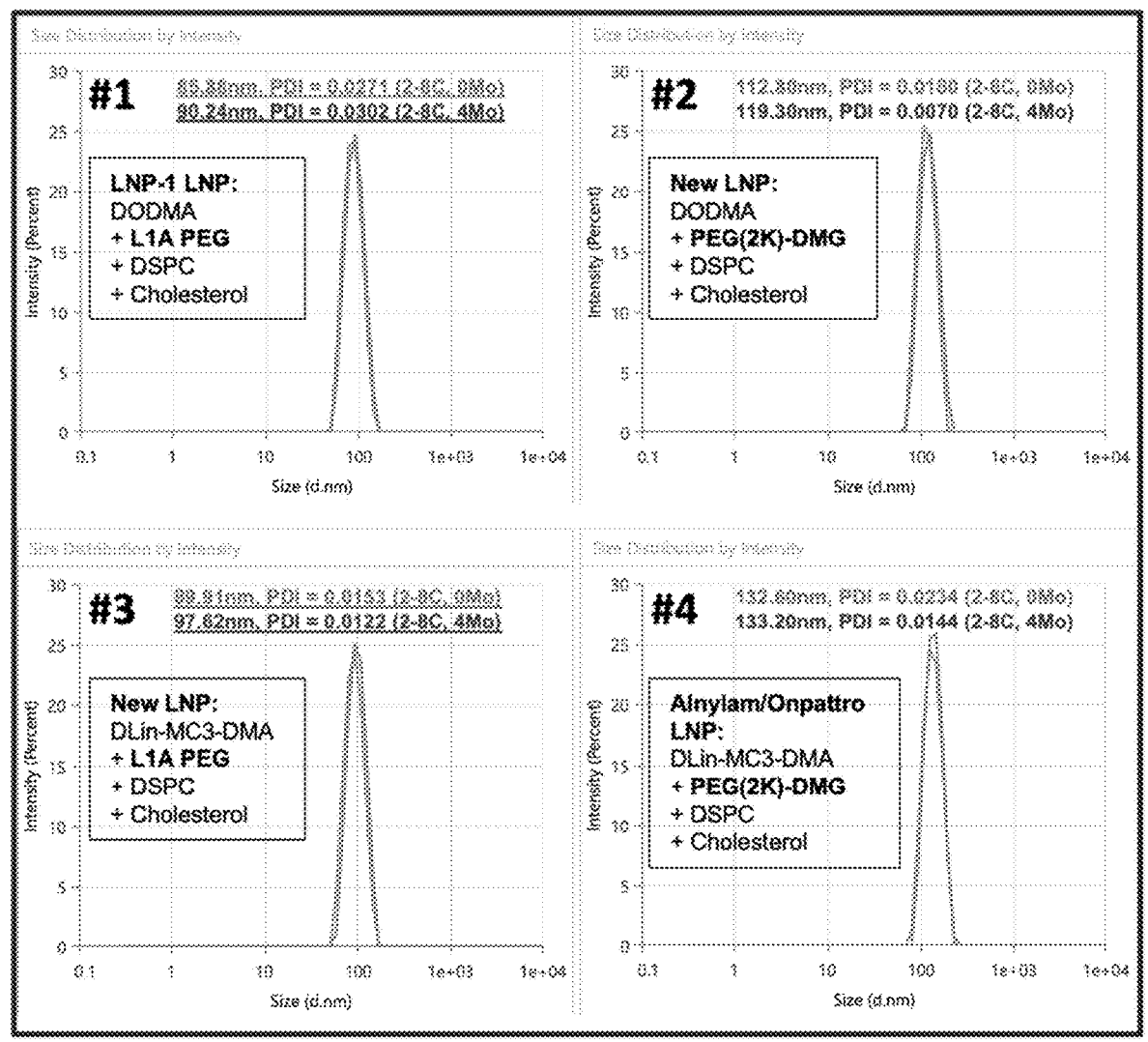
Figure 9:
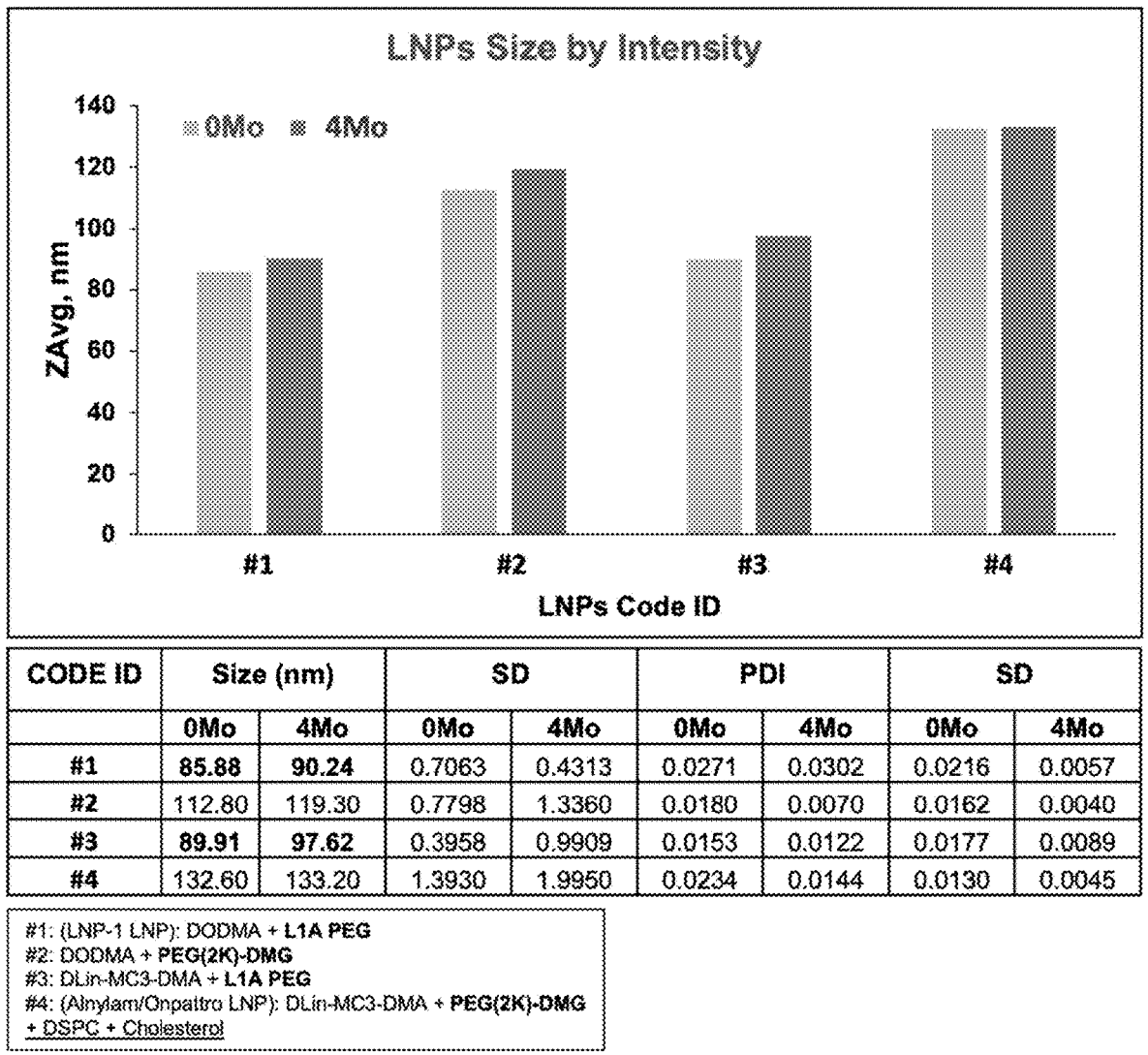

Example 9 shows that LNP-1 platform's PEGylated L1A is compatible with other ionizable lipids, e.g., DLin-MC3-DMA in Alnylam's Onpattro LNP formulations (FIG. 9). PEGylated L1A LNPs have smaller sizes and are both structurally and functionally stable. Whereas in contrast, the new LNPs combining Alnylam/Onpattro's PEG (2K)-DMG with DODMA have no function and are only structurally stable.

Example 10: A working example of LNP-1's long-term structural lipids stability and quantification (FIG. 10). eGFP mRNA/LNP-1s are stable for long-term storage at 2-8° C.—the lipid composition and total lipid content of 9 months old formulations are comparable to that of freshly-formulated.

Figure 11:
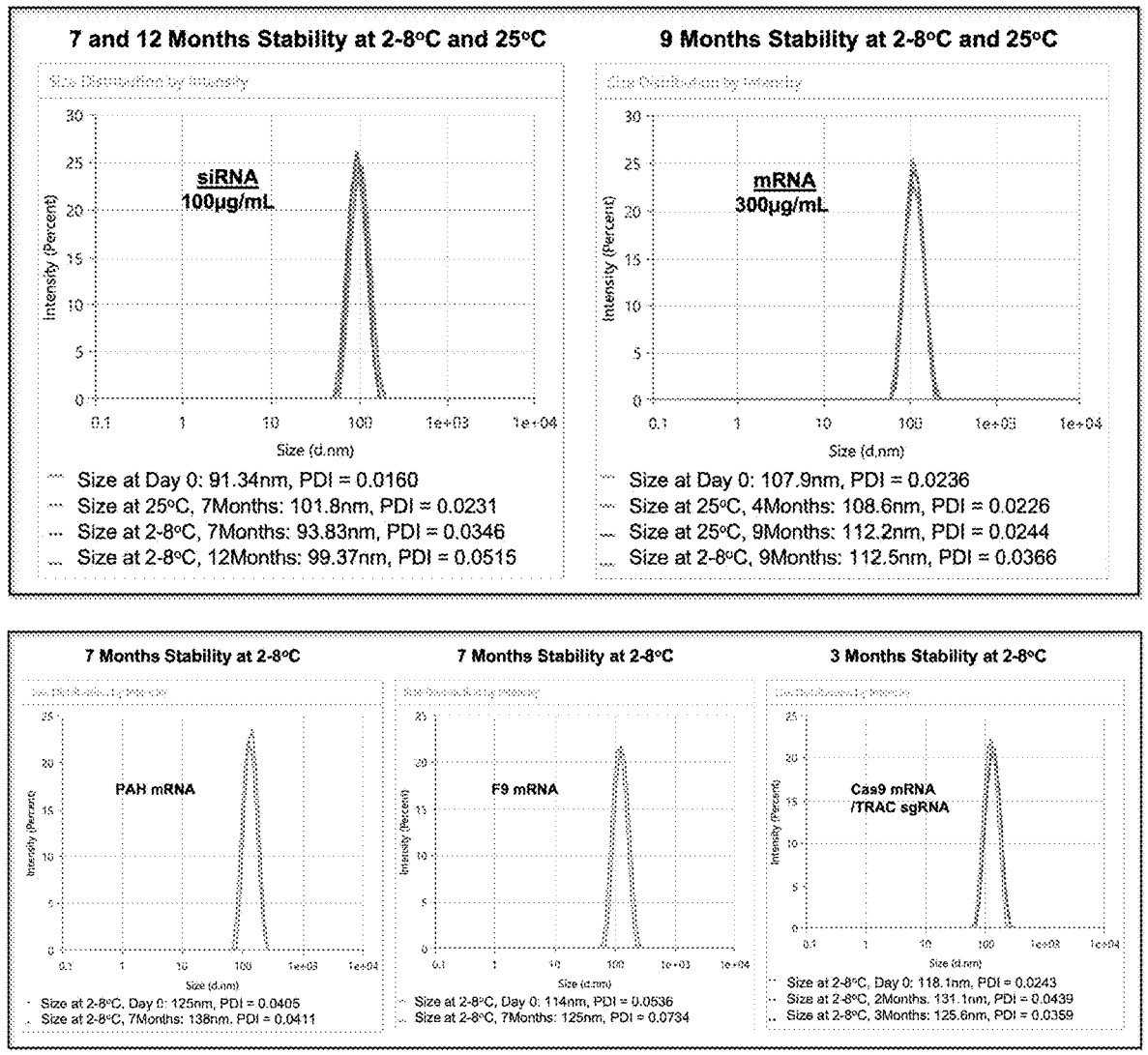
FIG. 11 shows that, when loaded with different RNA payloads, LNP-1 formulations are stable for long-term storage at different temperatures (2-8° C. or 25° C.).

Example 11: Working examples of LNP-1's long-term physicochemical stability (FIG. 11). When loaded with different RNA payloads, LNP-1 formulations are stable for long-term storage at different temperatures (2-8° C. or 25° C.), as indicated by size distribution and dispersity assessments by Z-Avg size spectra using the Zetasizer Dynamic Light Scattering (DLS) system from Malvern Panalytical. LNP-1 platform's PDI (polydispersity index, a leading indicator of shelf-life stability as well as in vivo stability and efficacy of nucleic acid delivery) typically goes 0.01-0.07 (PDI<0.1). For other lipid nanoparticles clinical and commercially available PDI goes 0.1-0.3 (PDI>0.1).

Figure 12:
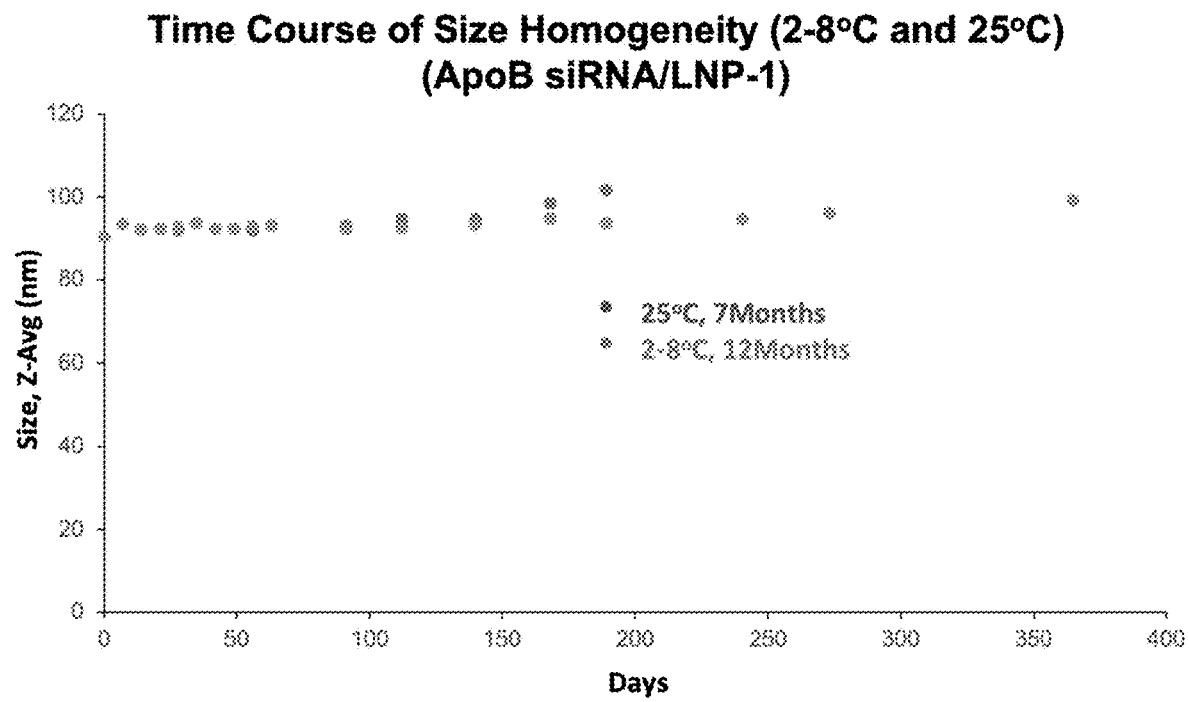
FIG. 12 shows that ApoB siRNA/LNP-1s are stable for long-term storage at different temperatures (2-8° C. or 25° C.).

Example 12: A working example of LNP-1's long-term physicochemical stability (FIG. 12). ApoB siRNA/LNP-1s are stable for long-term storage at different temperatures (2-8° C. or 25° C.), as indicated by the size homogeneity during the course of long-term stability study.

Figure 13:
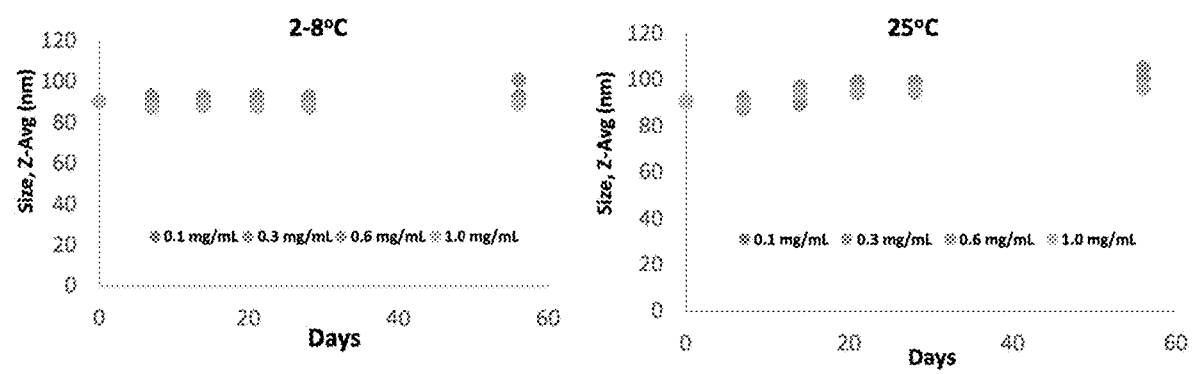
FIG. 13 shows that different stock concentrations of ApoB siRNA/LNP-1s are stable for long-term storage at different temperatures (2-8° C. or 25° C.).

Example 13: Different stock concentrations of ApoB siRNA/LNP-1s are stable for long-term storage at different temperatures (FIG. 13). ApoB siRNA/LNP-1 formulations were prepared at four stock concentrations-0.1, 0.3, 0.6 and 1.0 mg/mL and then stored at 2-8° C. or 25° C. for long-term stability study. In vivo potency was first confirmed by Western Blotting of livers from C57BL/6 mice received different dosages of ApoB siRNA/LNP-1s (a single i.v injection; 1, 3, 6 or 10 mg/kg). These four LNPs stocks were also sampled at various time points for size distribution and dispersity assessments by Z-Avg size spectra. Data are shown as time course of size homogeneity at 2-8° C. or 25° C.

Example 14: A working example of LNP-1's long-term physicochemical stability (FIG. 14). ApoB siRNA/LNP-1s are stable for long-term storage at 40° C., as indicated by the size homogeneity and distribution.

Figure 15:
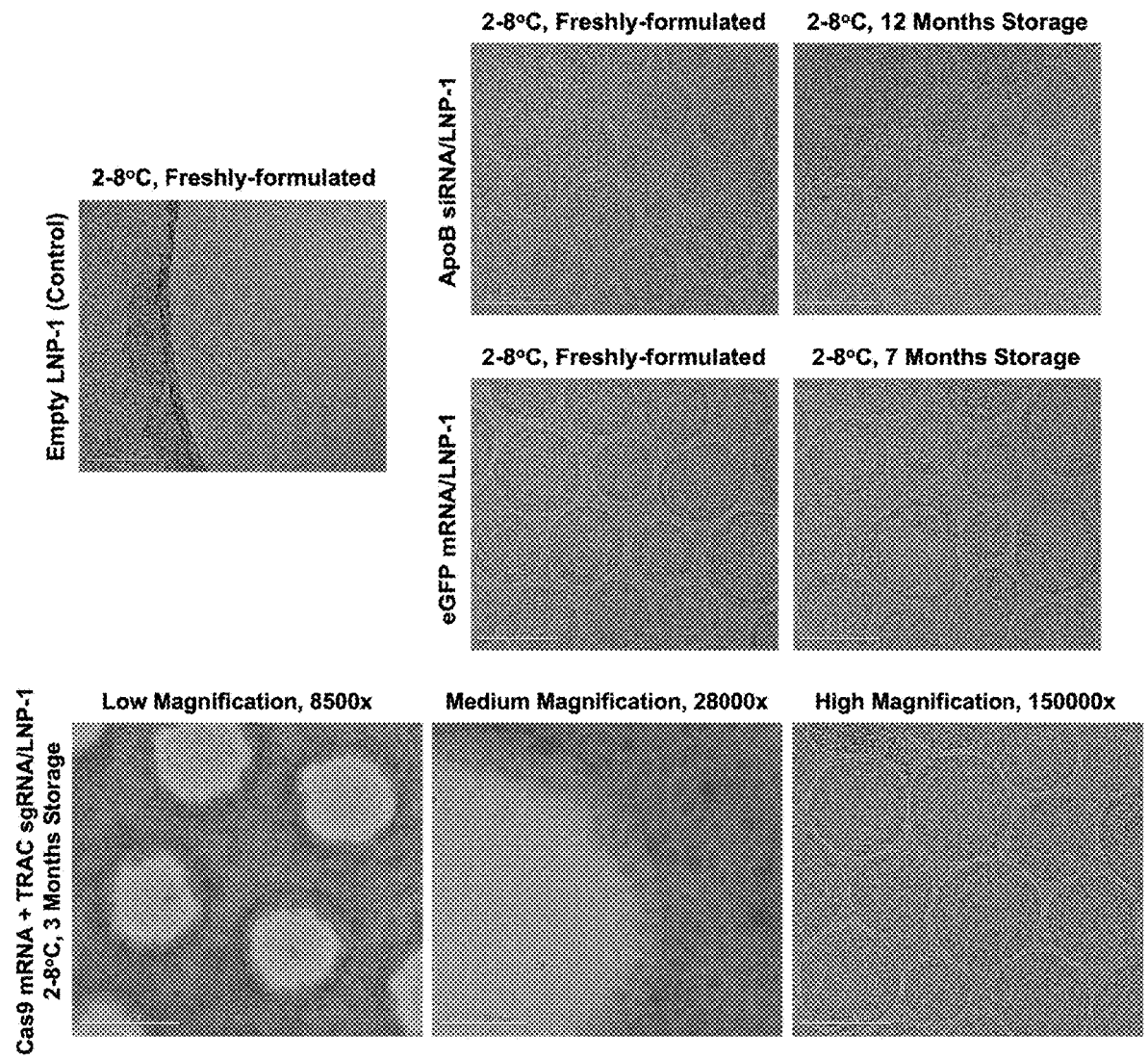
FIG. 15 shows that, when loaded with different RNA payloads, LNP-1 formulations morphology and topology remain stable for long-term storage at 2-8° C.

Example 15: Working examples of LNP-1's long-term morphology stability (FIG. 15). When loaded with different RNA payloads, LNP-1 formulations morphology remains stable for long-term storage at 2-8° C., as indicated by the Cryo-TEM images.

Example 16: Summary of payloads versatility and long-term stability of the LNP-1 technology platform (FIG. 16). LNP-1 formulations can encapsulate varied types and sizes of nucleic acids payloads and remain stable for long-term storage at 2-8° C.

Figure 17:
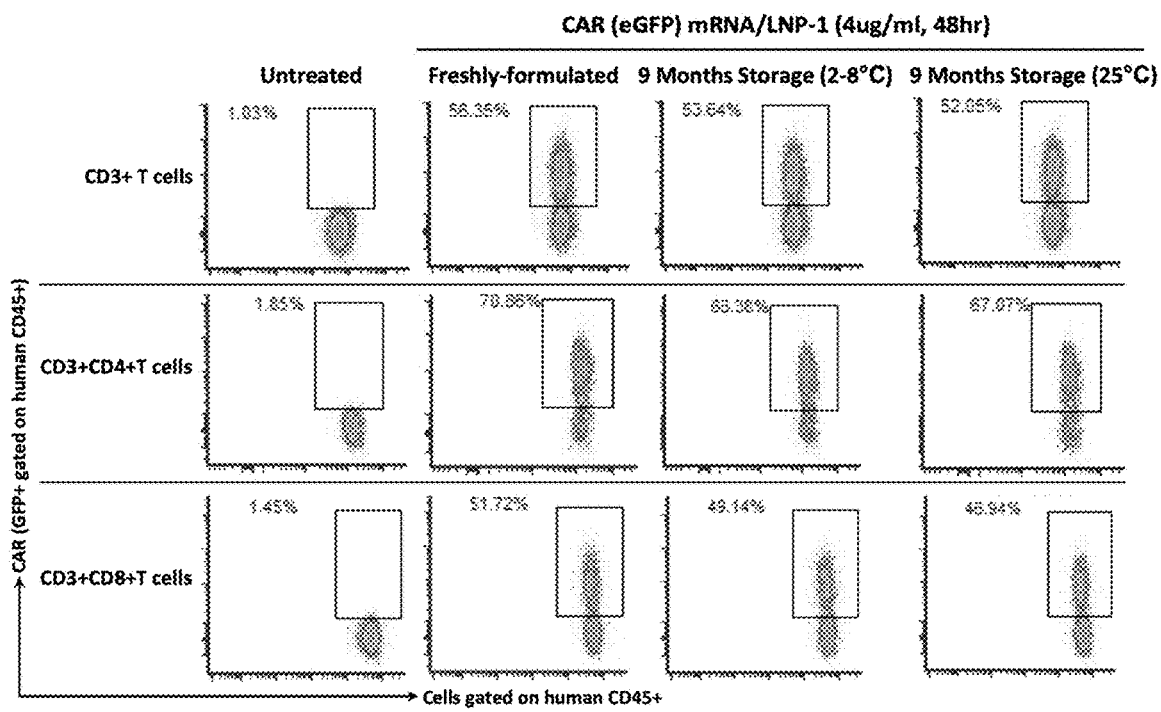
FIG. 17 shows that eGFP mRNA/LNP-1s are functionally stable for long-term storage at different temperatures (2-8° C. or 25° C.)—the CAR-T generation potency of 9 months old formulations is comparable to that of freshly-formulated.

Example 17: A working example of LNP-1's long-term function stability (FIG. 17). eGFP mRNA/LNP-1s are functionally stable for long-term storage at different temperatures (2-8° C. or 25° C.)—the CAR-T generation potency of 9 months old formulations is comparable to that of freshly-formulated.

Figure 18:
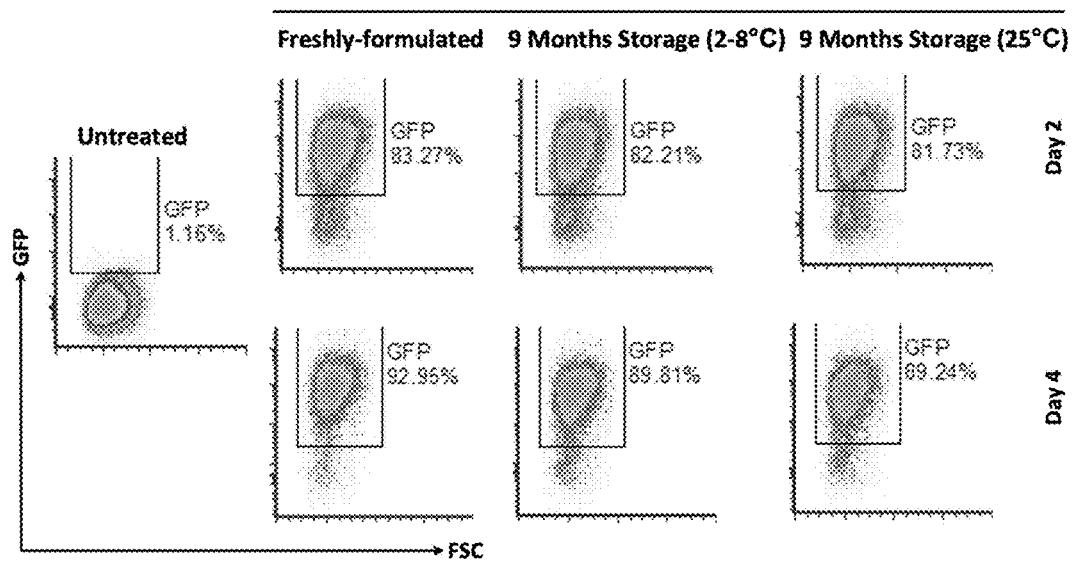
FIG. 18 shows that eGFP mRNA/LNP-1s are functionally stable for long-term storage at different temperatures (2-8° C. or 25° C.)—the gene delivery potency of 9 months old formulations is comparable to that of freshly-formulated.

Example 18: A working example of LNP-1's long-term function stability (FIG. 18). eGFP mRNA/LNP-1s are functionally stable for long-term storage at different temperatures (2-8° C. or 25° C.)—the gene delivery potency of 9 months old formulations is comparable to that of freshly-formulated.

Figure 19:
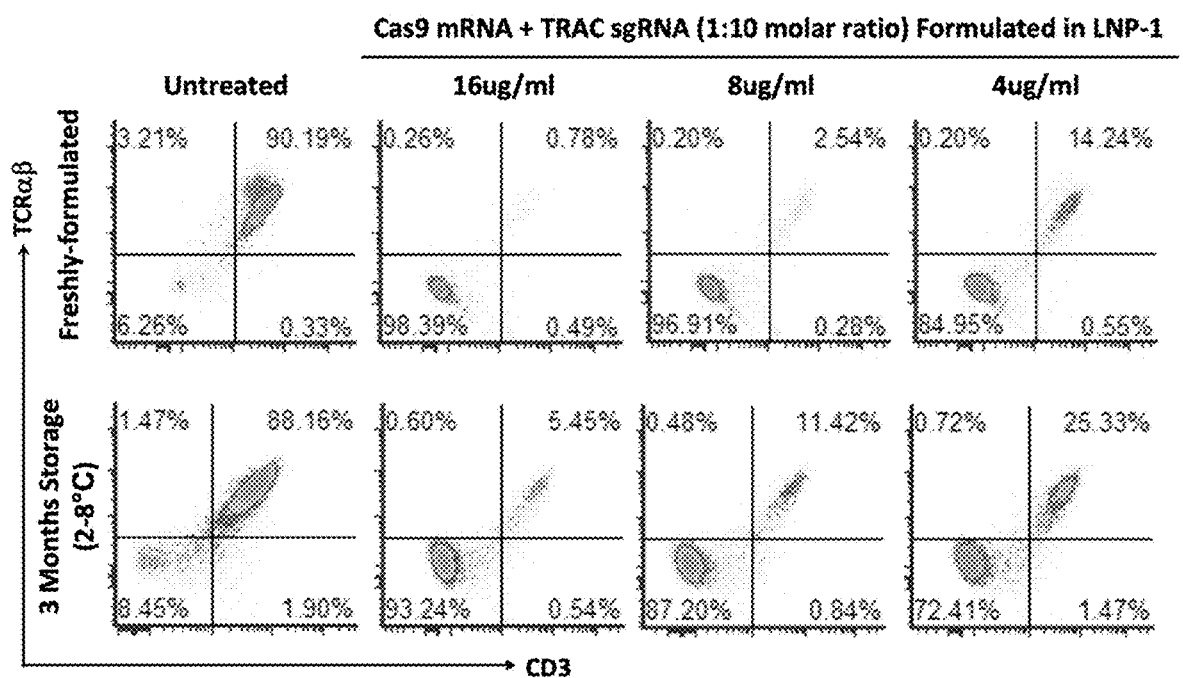
FIG. 19 shows that Cas9 mRNA+TRAC sgRNA/LNP-1s are functionally stable for long-term storage at 2-8° C.—the knockout potency of 3 months old formulations is comparable to that of freshly-formulated.

Example 19: A working example of LNP-1's long-term function stability (FIG. 19). LNP-1's gene editing potency using CRISPR-Cas9-mediated knockout of TCRa receptor in Jurkat T cells was examined by flow cytometry. Cas9 mRNA+TRAC sgRNA/LNP-1s are functionally stable for long-term storage at 2-8° C.—the knockout potency of 3 months old formulations is comparable to that of freshly-formulated.

Figure 20:
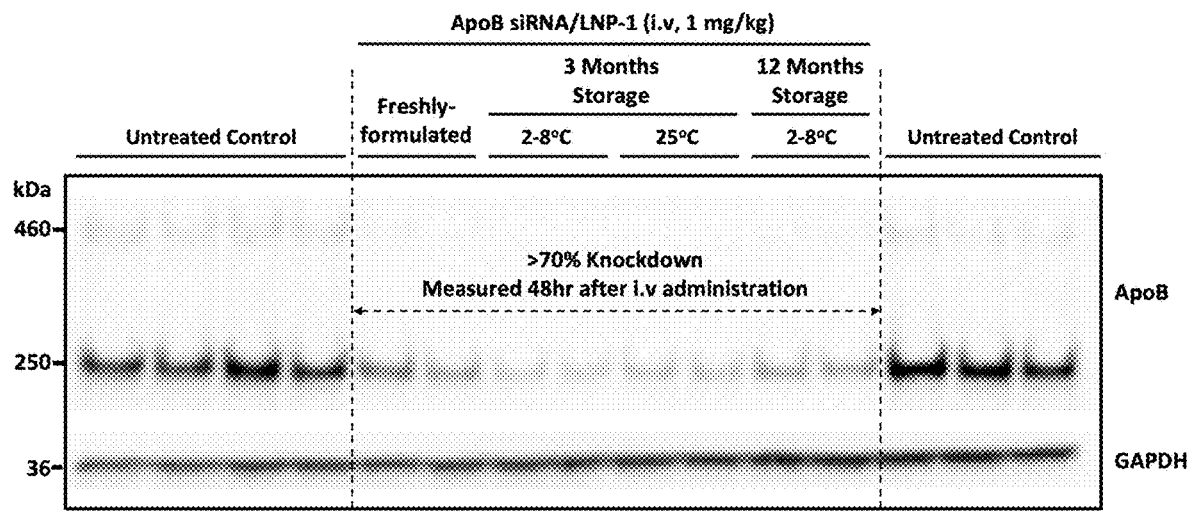
FIG. 20 shows that ApoB siRNA/LNP-1s are functionally stable for long-term storage at different temperatures (2-8° C. or 25° C.)—the gene silencing potency of aged formulations is comparable to that of freshly-formulated (all had >70% knockdown efficiency).

Example 20: A working example of LNP-1's long-term function stability (FIG. 20). ApoB siRNA/LNP-1's in vivo gene silencing potency during long-term storage was evaluated by Western Blotting of liver ApoB protein levels. ApoB siRNA/LNP-1s are functionally stable for long-term storage at different temperatures (2-8° C. or 25° C.)—the gene silencing potency of aged formulations is comparable to that of freshly-formulated (all achieved >70% knockdown efficiency).

Example 21: Working examples of LNP-1's versatile therapeutic applications-gene silencing (FIG. 21). Marked in vivo ApoB protein knockdown efficiency was achieved in the liver tissues from C57BL/6 mice i.v administrated with a single dose of ApoB siRNA/LNP-1s (1, 3, 6, or 10 mg/kg). Mock siRNA/LNP-1s (1 mg/kg) served as the negative control. Na/K ATPase or eRF1 protein was used as the loading control.

Figure 22:
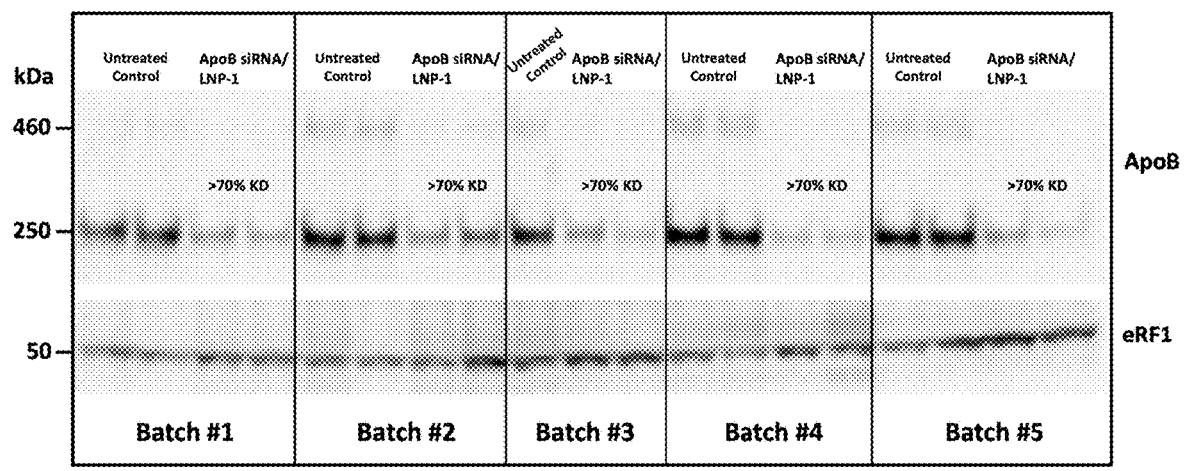
FIG. 22 shows batch consistency of stable ApoB siRNA/LNP-1 formulations.

Example 22: In vivo potency of different batches of stable ApoB siRNA/LNP-1 formulations are consistent (FIG. 22). Five different batches of ApoB siRNA/LNP-1s were prepared and i.v administrated into C57BL/6 mice (1 mg/kg). 48 hours later, mouse livers were harvested, and knockdown (KD) efficiency was evaluated as detailed in Example 4. eRF1 protein was used as the loading control. All five batches of ApoB siRNA/LNP-1 achieved ≥70% KD efficiency.

Figure 23:
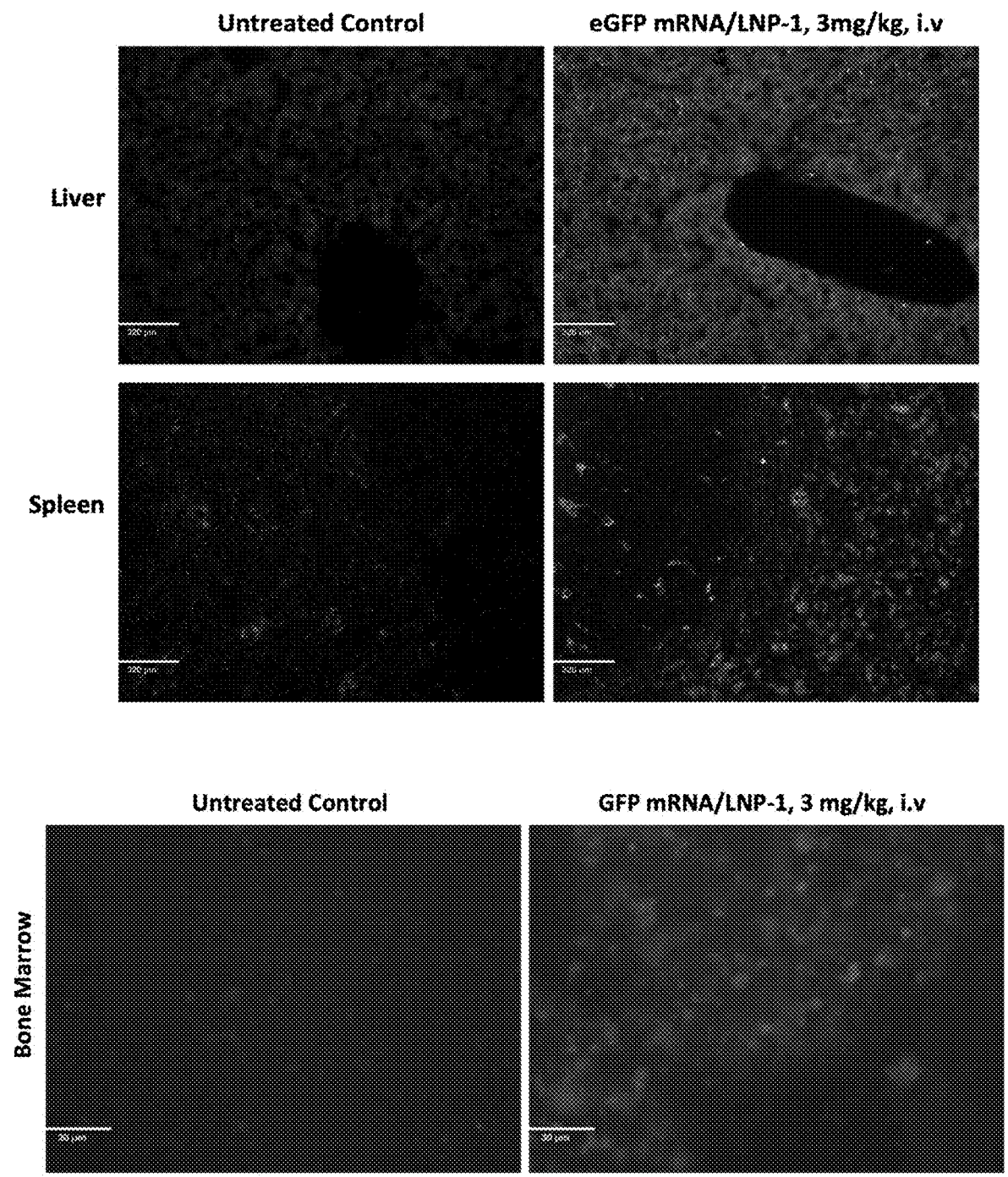
FIG. 23 shows LNP-1's potency delivering eGFP mRNA to the liver, spleen and bone marrow.

Example 23: A working example of LNP-1's versatile therapeutic applications-mRNA therapy and target organs (e.g., the liver, spleen and bone marrow) (FIG. 23). C57BL/6 mice received a single i.v injection of 3 mg/kg GFP mRNA/LNP-1s. 48 hours later, GFP expression in different tissues were visualized by fluorescence microscopy. Tissues from untreated mice served as negative controls. The liver, spleen and bone marrow showed strong GFP signals. Specifically, strong GFP signal is seen in the liver parenchyma and areas around geminal center in the spleen. Also notably, typical evaluations of in vivo mRNA delivery potency by other LNP technologies are often using luciferase luminescence in vivo imaging, which is more sensitive than GFP fluorescent signal.

Figure 24:
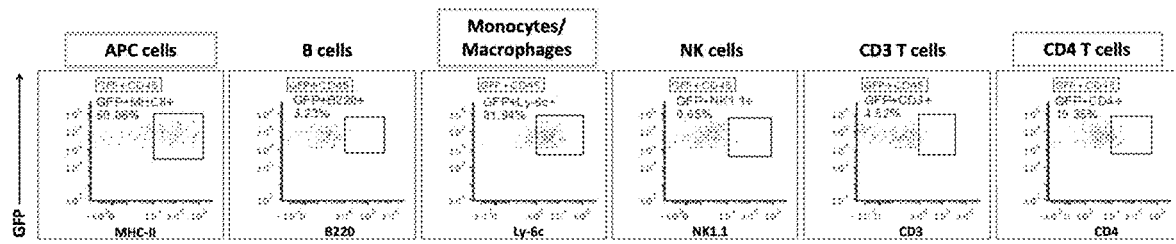
FIG. 24 shows LNP-1's potency delivering CAR (eGFP) mRNA to activated immune cells (e.g., antigen presenting cells (APC), monocytes/macrophages, and CD4 T cells).

Example 24: A working example of LNP-1's versatile therapeutic applications-immune cell engineering (e.g., chimeric antigen receptor (CAR) expression) (FIG. 24). LNP-1's potency delivering CAR (eGFP) mRNA to activated immune cells is demonstrated-48 hours after treatment with 1 μg/ml of CAR (eGFP) mRNA/LNP-1s, intracellular GFP signal is chiefly seen in antigen presenting cells (APC), monocytes/macrophages, and CD4 T cells.

Figure 25:
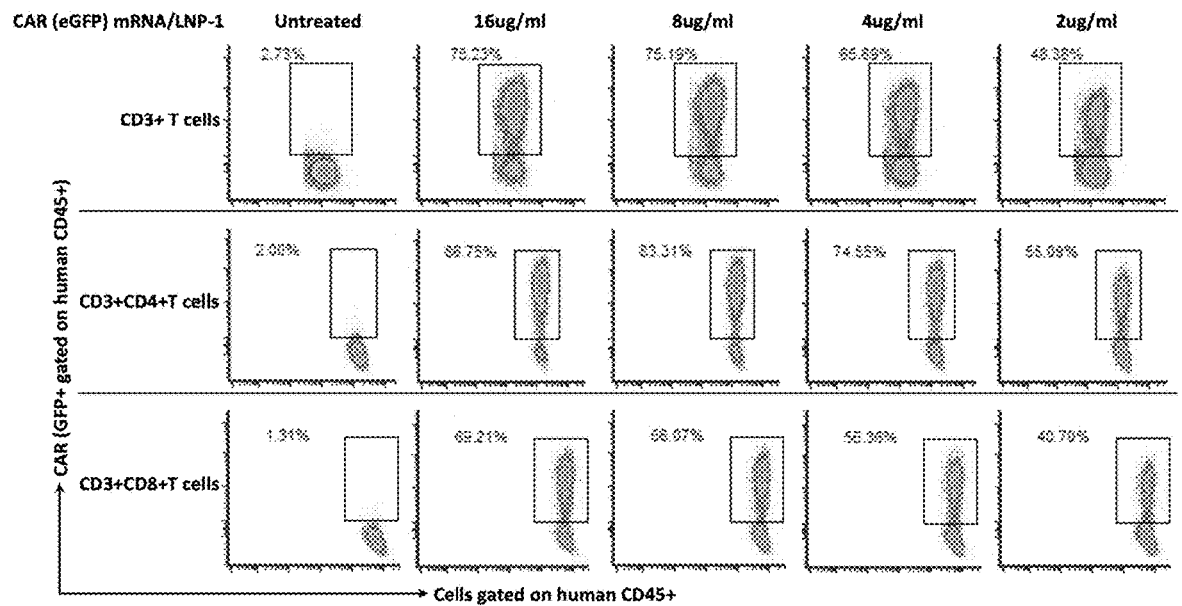
FIG. 25 shows LNP-1's CAR-T generation potency (ex vivo).

Example 25: A working example of LNP-1's versatile therapeutic applications-ex vivo CAR-T cell engineering (FIG. 25). High-quality transient CAR-T cells are ex vivo generated by CAR (eGFP) mRNA/LNP-1s-80-90% transfection efficiency achieved in the 4-16 μg/ml dose groups with over 80% CAR-T cell viability in all groups.

Figure 26:
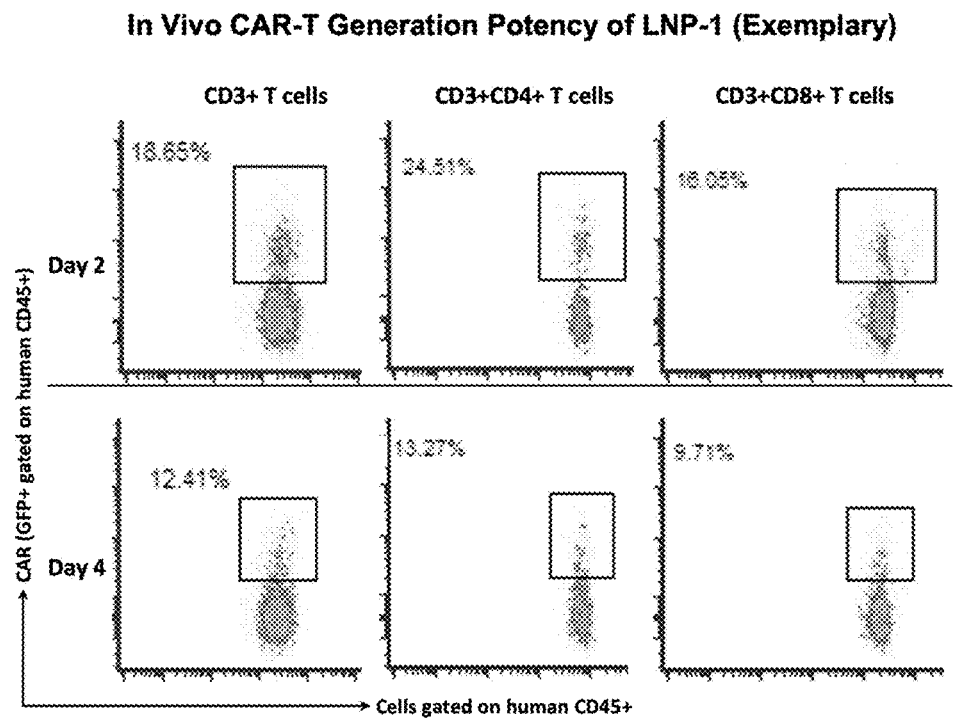
FIG. 26 shows LNP-1's CAR-T generation potency (in vivo).

Example 26: A working example of LNP-1's versatile therapeutic applications—in vivo CAR-T cell engineering (FIG. 26). Potent in vivo CAR-T cell generation is achieved by CAR (eGFP) mRNA/LNP-1s. Approximately 16-25% transfection efficiency is seen herein (whereas it's generally <15% in the literature); and persistent in vivo CAR expression is noted at day 4 post transfection.

Figure 27:
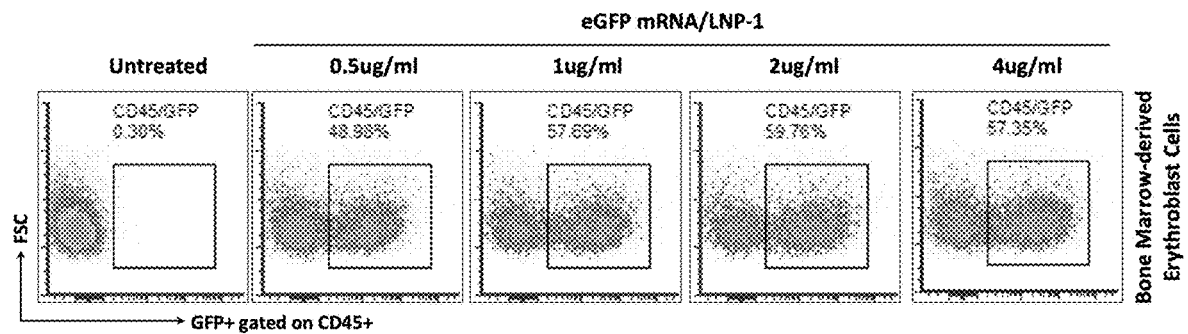
FIG. 27 shows LNP-1's potency delivering eGFP mRNA to hematopoietic stem cells, e.g., bone marrow-derived erythroblast cells.

Example 27: A working example of LNP-1's versatile therapeutic applications-stem cell engineering (e.g., hematopoietic stem cells) (FIG. 27). eGFP mRNA is effectively and functionally delivered to bone marrow-derived erythroblast cells by LNP-1 formulations. 50-60% transfection efficiency is seen even in the lower dose ranges (i.e., 0.5-1 μg/ml), while cell viability remains >95% in all groups.

Figure 28:
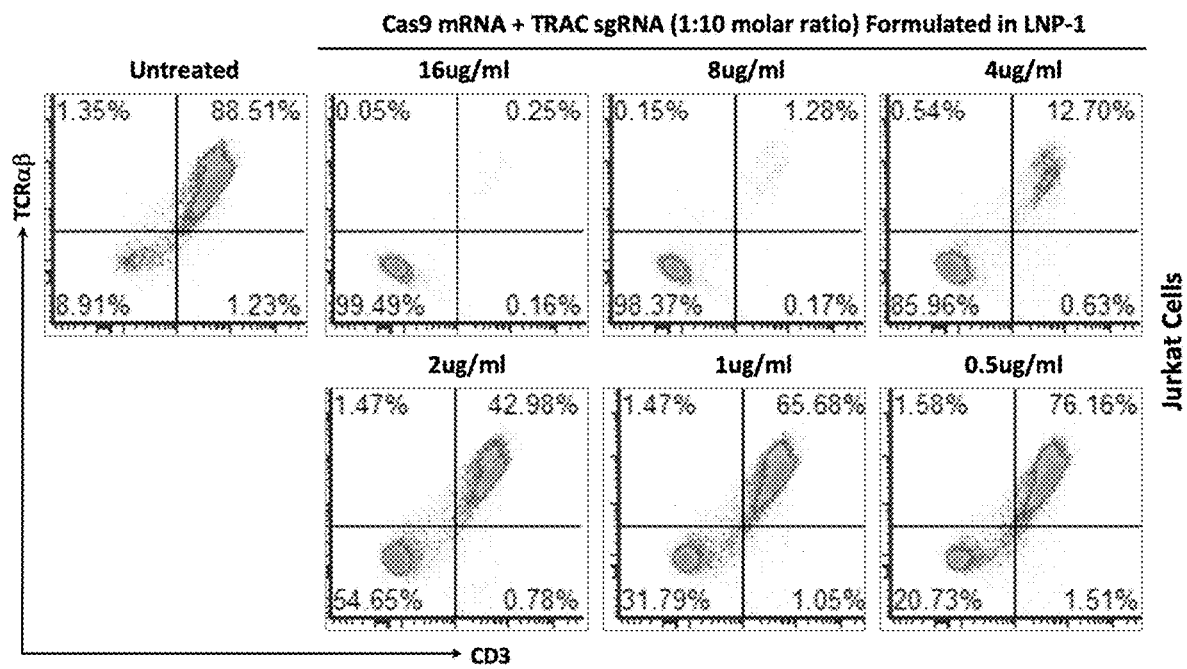
FIG. 28 shows LNP-1's CRISPR gene editing potency.

Example 28: A working example of LNP-1's versatile therapeutic applications-gene editing (FIG. 28). >85%

TCRα knockout efficiency is achieved within the dose ranges of 4-16 μg/ml 4 days after Cas9 mRNA+TRAC sgRNA/LNP-1 transfection, while cell viability remains >95% in all groups. Such TCRα knockout efficiency is persistently maintained at the end of the study (day 14).

Example 29: A working example of LNP-1's versatile therapeutic applications-gene therapy for malignant cells (e.g., human leukemia cells) (FIG. 29). eGFP mRNA is effectively and functionally delivered to human Jurkat T leukemia cells and human THP-1 monocytic leukemia cells. In Jurkat cells, even the lowest dose 12.5 ng (=0.125 μg/ml) eGFP mRNA/LNP-1s achieve 100% and strong delivery potency. 100 ng (=1 μg/ml) produce GFP signal beyond the highest detection range. Such GFP expression is persistent up to 10 days. Also notably, current evaluations of in vitro mRNA delivery potency by other LNP technologies are often using 100-200 ng or higher doses.

Example 30: A working example of LNP-1's versatile therapeutic applications-gene therapy for malignant cells (e.g., human lymphoma cells) (FIG. 30). eGFP mRNA is effectively and functionally delivered to HCC1739BL human lymphoma cells by LNP-1 formulations.

Example 31: A working example of LNP-1's versatile therapeutic applications-gene therapy for cancer cells (e.g., human liver cancer cells) (FIG. 31). eGFP mRNA is effectively and functionally delivered to HepG2 human liver cancer cells by LNP-1 formulations and such GFP expression is persistent up to the study termination (day 7).

Example 32: Working examples of LNP-1's versatile therapeutic applications-vaccines (FIG. 32). Spike mRNA-1273 loaded LNP-1s (5 μg in 50 μL PBS) were intramuscularly (IM) or subcutaneously (SC) administered into C57BL6 or BALB/c mice on days 0 (the prime dose) and 21 (the boost dose). On days 14 (Prime), 28 (Boost-d7) and 44 (Boost-d23) for C57BL6 mice or on days 28 (Post-Boost 1w), 35 (Post-Boost 2w) and 49 (Post-Boost 4w) for BALB/c mice, mouse blood were collected and evaluated for Spike protein RBD-specific IgG titres by ELISA. Mice received 50 μL PBS served as the negative control (PBS Ctrl or NC). LNP-1's potency as COVID-19 mRNA vaccines is demonstrated-all mice injected with Spike mRNA-1273/LNP-1s produced persistent high Spike RBD-specific IgG titres.

Example 33: Working examples of LNP-1's good safety profile (FIG. 33). 48 hours after i.v administration of ApoB siRNA/LNP-1s (1, 3 or 6 mg/kg) into C57BL6 mice, blood chemistry analyses of liver enzymes (ALP, AST and ALT), kidney function (BUN and creatine kinase) and proteins levels (total protein, albumin and globulin) as well as liver tissue histology were conducted. Within the therapeutic window (e.g. 0.1-3 mg/kg), there is no in vivo toxicity observed with LNP-1 formulations.

Figure 34:
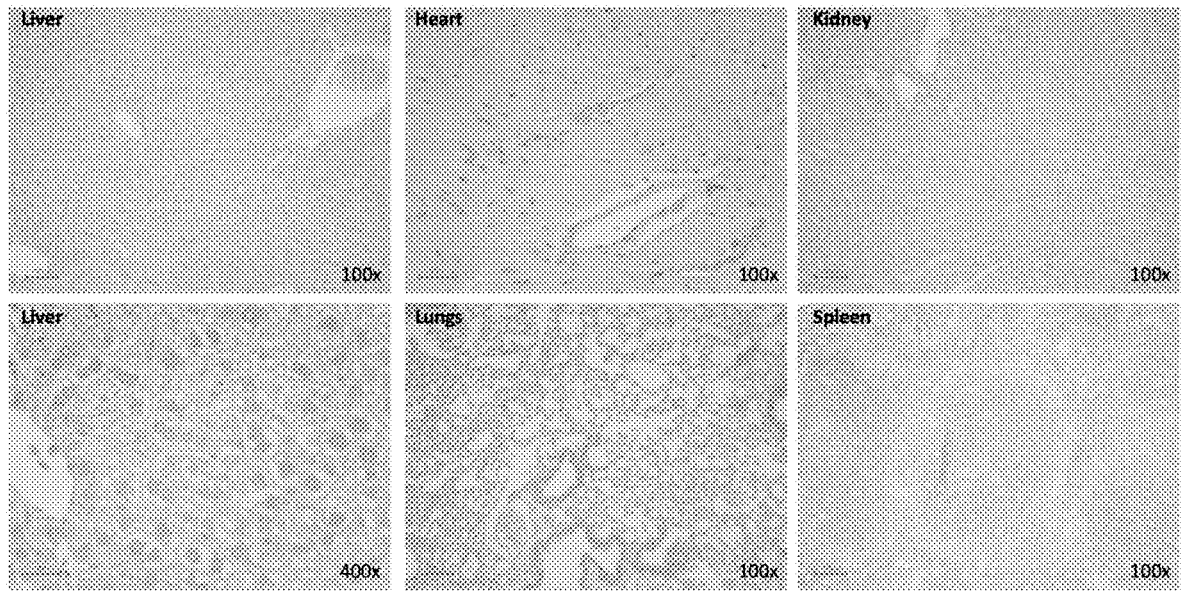
FIG. 34 shows that LNP-1 formulations do not cause tissue toxicity in all major organs examined post i.v administration.

Example 34: A working example of LNP-1's good safety profile (FIG. 34). 48 hours after i.v administration of 3 mg/kg ApoB siRNA/LNP-1s into C57BL6 mice, major internal organs including liver, heart, kidney, lungs, and spleen were harvested and subjected to tissue histology assessment. LNP-1 formulations do not cause tissue toxicity in all organs examined.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

The invention claimed is:

1. A lipid nanoparticle formulation, wherein the lipid nanoparticles comprise four components:
   (i) a PEG-conjugated phospholipid having the structure

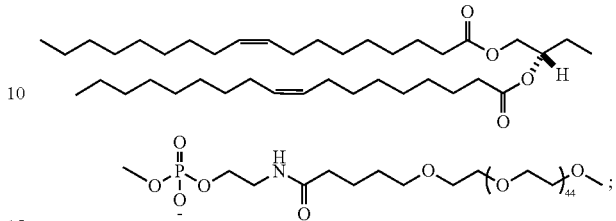

(ii) an ionizable lipid having the structure

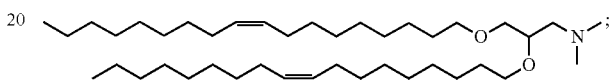

(iii) a non-cationic phospholipid having the structure

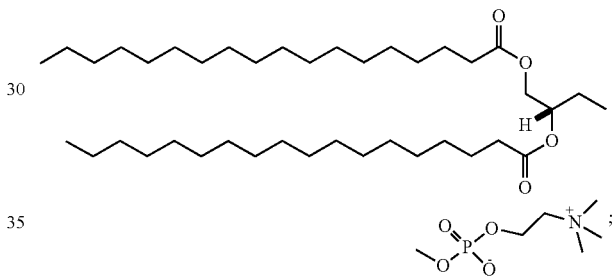

and
   (iv) cholesterol.

2. The formulation of claim 1, wherein the PEG-conjugated phospholipid is present in the lipid nanoparticle in an average amount of 0.25 to 10 mol % of the four components.

3. The formulation of claim 2, wherein the ionizable lipid is present in the lipid nanoparticle in a relative amount of 5 to 60 mol %, the non-cationic phospholipid is present in the lipid nanoparticle in a relative amount of 5 to 55 mol %, and the cholesterol is present in the lipid nanoparticle in a relative amount of 30 to 60 mol %, with the proviso that the mol % of the four components totals 100 mol %.

4. The formulation of claim 1, wherein the lipid nanoparticles have a relative ratio of 50:10:39.25:0.75 for the ionizable lipid, the non-cationic phospholipid, cholesterol and the PEG-conjugated phospholipid.

5. The formulation of claim 1, wherein the lipid nanoparticles are stable at 2-8° C. for at least 180 days.

6. The formulation of claim 4, wherein the lipid nanoparticles are stable at 2-8° C. for at least 180 days after initial preparation of the formulation.

7. The formulation of claim 1, wherein the lipid nanoparticles encapsulate nucleic acids.

8. The formulation of claim 7, wherein the nucleic acids comprise RNA.

9. The formulation of claim 8, wherein the RNA is selected from the group consisting of small interfering RNA, asymmetrical interfering RNA, microRNA, a CRISPR guide RNA, Dicer-substrate RNA, small hairpin RNA, mRNA, circular RNA, self-amplifying RNA, long non-coding RNA and antisense RNA.

10. The formulation of claim 5, wherein after storage for at least 180 days 2-8° C. the lipid nanoparticles maintain a polydispersity within 10% of polydispersity measured at initial preparation of the formulation.

11. The formulation of claim 7, wherein after storage for at least 180 days 2-8° C. the lipid nanoparticles maintain a polydispersity within 10% of polydispersity measured at initial preparation of the formulation.

12. The lipid nanoparticle formulation of claim 1, wherein (iv) is

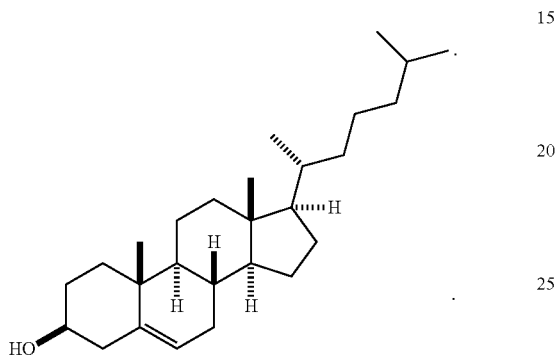

13. The formulation of claim 8, wherein the RNA is mRNA.

* * * * *